(12) United States Patent  
Chappie et al.

(10) Patent No.: US 9,120,788 B2  
(45) Date of Patent: Sep. 1, 2015

(54) AZABENZIMIDAZOLE COMPOUNDS

(71) Applicant: Pfizer Inc., Groton, CT (US)

(72) Inventors: Thomas Allen Chappie, Carlisle, MA (US); Patrick Robert Verhoest, Newton, MA (US); Nandini Chaturbhai Patel, Waltham, MA (US); Matthew Merrill Hayward, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/180,463

(22) Filed: Feb. 14, 2014

(65) Prior Publication Data

US 2014/0235612 A1    Aug. 21, 2014

Related U.S. Application Data

(60) Provisional application No. 61/766,268, filed on Feb. 19, 2013.

(51) Int. Cl.
| C07D 401/14 | (2006.01) |
| A61K 31/437 | (2006.01) |
| C07D 471/04 | (2006.01) |

(52) U.S. Cl.  
CPC .................................... *C07D 471/04* (2013.01)

(58) Field of Classification Search  
CPC ............................ C07D 401/14; A61K 31/437  
USPC .......................................... 546/118; 514/303  
See application file for complete search history.

(56) References Cited

U.S. PATENT DOCUMENTS

| 5,814,651 | A  | 9/1998  | Duplantier et al. |
| 6,924,287 | B1 | 8/2005  | Janssens et al. |
| 7,544,684 | B2 | 6/2009  | Eggenweiler et al. |
| 7,605,168 | B2 | 10/2009 | Ibrahim et al. |
| 7,709,518 | B2 | 5/2010  | Chen et al. |
| 7,723,323 | B2 | 5/2010  | Andersen et al. |
| 7,985,753 | B2 | 7/2011  | Danysz et al. |
| 2003/0064031 | A1 | 4/2003 | Humphrey et al. |
| 2003/0064374 | A1 | 4/2003 | Ait Ikhlef et al. |
| 2003/0069260 | A1 | 4/2003 | Guadilliere et al. |
| 2003/0092706 | A1 | 5/2003 | Barsig |
| 2003/0153595 | A1 | 8/2003 | Walker et al. |
| 2003/0176450 | A1 | 9/2003 | Atkinson et al. |
| 2003/0187257 | A1 | 10/2003 | Gaudilliere |
| 2003/0187261 | A1 | 10/2003 | Havlicek et al. |
| 2003/0191086 | A1 | 10/2003 | Hanus et al. |
| 2004/0087588 | A1 | 5/2004 | Beaton et al. |
| 2004/0157933 | A1 | 8/2004 | Akiyama et al. |
| 2004/0162314 | A1 | 8/2004 | Dube et al. |
| 2004/0176252 | A1 | 9/2004 | Eggenweiler et al. |
| 2004/0176419 | A1 | 9/2004 | Knowles et al. |
| 2004/0180918 | A1 | 9/2004 | Knowles et al. |
| 2004/0235845 | A1 | 11/2004 | Eggenweiler et al. |
| 2004/0242597 | A1 | 12/2004 | Klein et al. |
| 2004/0254212 | A1 | 12/2004 | Denholm et al. |
| 2004/0259863 | A1 | 12/2004 | Eggenweiler et al. |
| 2005/0009829 | A1 | 1/2005 | Nazare et al. |
| 2005/0014762 | A1 | 1/2005 | Beume et al. |
| 2005/0020587 | A1 | 1/2005 | Bailey et al. |
| 2005/0020593 | A1 | 1/2005 | Mailliet et al. |
| 2005/0049263 | A1 | 3/2005 | Kasibhatla et al. |
| 2005/0070514 | A1 | 3/2005 | Rapeport |
| 2005/0070569 | A1 | 3/2005 | Guay et al. |
| 2005/0101000 | A1 | 5/2005 | Bennett et al. |
| 2005/0137234 | A1 | 6/2005 | Bressi et al. |
| 2005/0272803 | A1 | 12/2005 | Ruiping et al. |
| 2005/0289660 | A2 | 12/2005 | Wang et al. |
| 2006/0025426 | A1 | 2/2006 | Fraley |
| 2006/0041006 | A1 | 2/2006 | Ibrahim et al. |
| 2006/0148805 | A1 | 7/2006 | Chen et al. |
| 2006/0183909 | A1 | 8/2006 | Schmitt et al. |
| 2007/0010521 | A1 | 1/2007 | Ukita et al. |
| 2007/0191426 | A1 | 8/2007 | Edlin et al. |
| 2007/0275984 | A1 | 11/2007 | Imogai et al. |
| 2008/0096884 | A1 | 4/2008 | Edlin et al. |
| 2008/0096903 | A1 | 4/2008 | Chen et al. |
| 2008/0102475 | A1 | 5/2008 | Kan et al. |
| 2009/0029938 | A1 | 1/2009 | Renzi et al. |

(Continued)

FOREIGN PATENT DOCUMENTS

| IN | 55MUM2009 | 9/2010 |
| JP | 08295667 | 11/1996 |

(Continued)

OTHER PUBLICATIONS

Yutilov et al., Khimiya Geterotsiklicheskikh Soedinenii (1975), (10), 1389-93.*
Dorange et al., Bioorganic & Medicinal Chemistry Letters (2012), 22(22), 6888-6895.*
Deninno, Michael R, "Future Directions in Phosphodiesterase Drug Discovery", Bioorganic and Medicinal Chemistry Letters, Nov. 15, 2012, pp. 6794-6800, 22(22).
Papp, K., et al., "Efficacy of apremilast in the treatment of moderate to severe psoriasis: a randomized controlled trial", Lancet, Aug. 25-31, 2012, pp. 738-746, 380(9843).
Donnell, A. F., et al., "Identification of pyridazio[4,5-b]indolizines as selective PDE4B Inhibitors", Bioorganic & Medicinal Chemistry Letters, Apr. 1, 2010, pp. 2163-2167, 20(7).
Naganuma, K., et al., "Discovery of selective PDE4B inhibitors", Bioorganic & Medicinal Chemistry Letters, Jul. 15, 2009, pp. 3174-3176, 19(12).

(Continued)

*Primary Examiner* — Niloofar Rahmani  
(74) *Attorney, Agent, or Firm* — Richard V. Zanzalari

(57) ABSTRACT

The present invention is directed to compounds of formula I:

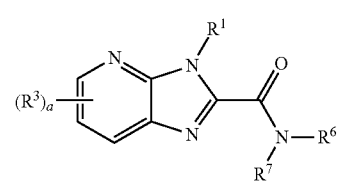

or a pharmaceutically acceptable salt thereof, wherein the substituents are as defined herein.

33 Claims, No Drawings

(56) References Cited

U.S. PATENT DOCUMENTS

| | | |
|---|---|---|
| 2009/0176778 A1 | 7/2009 | Schmitz et al. |
| 2009/0275586 A1 | 11/2009 | Govek et al. |
| 2010/0105729 A1 | 4/2010 | Govek et al. |
| 2010/0130737 A1 | 5/2010 | Itoh et al. |
| 2010/0204265 A1 | 8/2010 | Baskaran et al. |
| 2010/0267714 A1 | 10/2010 | Jorgensen et al. |
| 2011/0003820 A1 | 1/2011 | Henrich et al. |
| 2011/0173726 A1 | 7/2011 | Grob et al. |
| 2011/0275622 A1 | 11/2011 | Baker et al. |
| 2011/0275623 A1 | 11/2011 | Baker et al. |
| 2012/0041045 A1 | 2/2012 | Harvey et al. |
| 2012/0283274 A1 | 11/2012 | Plitt et al. |
| 2012/0289474 A1 | 11/2012 | Flockerzi et al. |

FOREIGN PATENT DOCUMENTS

| | | |
|---|---|---|
| WO | 0183481 | 11/2001 |
| WO | 03000697 | 1/2003 |
| WO | 03008373 | 1/2003 |
| WO | 03008396 | 1/2003 |
| WO | 03015789 | 2/2003 |
| WO | 03035650 | 5/2003 |
| WO | 2004042390 | 5/2004 |
| WO | 2004089471 | 10/2004 |
| WO | 2006034312 | 3/2006 |
| WO | 2006050976 | 5/2006 |
| WO | 2006089689 | 8/2006 |
| WO | 2007107499 | 9/2007 |
| WO | 2008004117 | 1/2008 |
| WO | 2008006050 | 1/2008 |
| WO | 2008006051 | 1/2008 |
| WO | 2008006052 | 1/2008 |
| WO | 2008033739 | 3/2008 |
| WO | 2008056176 | 5/2008 |
| WO | 2009023623 | 2/2009 |
| WO | 2009108551 | 9/2009 |
| WO | 2010004306 | 1/2010 |
| WO | 2010059836 | 5/2010 |
| WO | 2011093924 | 8/2011 |
| WO | 2011119465 | 9/2011 |

OTHER PUBLICATIONS

Robichaud, A., et al., "Deletion of phosphodiesterase 4D in mice shortens α2-adrenoreceptor-mediated anesthesia, a behavioral correlate of emesis", Journal of Clinical Investigation, Oct. 1, 2002, pp. 1045-1052, 110(7).

Siuciak, J. A., et al., "Antipsychotic profile of rolipram: efficacy in rats and reduced sensitivity in mice deficient in the phosphodiesterase-4B (PDE4B) enzyme", Psychopharmacology, Jun. 2007, pp. 415-425, 192(3).

Millar, J. K., et al., "Disrupted in schizophrenia 1 and phosphodiesterase 4B: towards an understanding of psychiatric illness", Journal of Physiology, Oct. 2007, pp. 401-405, 584(2).

Wang, C., et al., "The phosphodiesterase-4 inhibitor rolipram reverses Aβ-induced cognitive impairment and neuroinflammatory and apoptotic responses in rats", International Journal of Neuropsychopharmacology, Jul. 2012, pp. 749-766, 15(6).

Fujita, M., et al., "Downregulation of Brain Phosphodiesterase Type IV Measured with 11C-(R)-Rolipram Positron Emission Tomography in Major Depressive Disorder", Biological Psychiatry, Oct. 1, 2012, pp. 548-554, 72(7).

Sun, X., et al., "Rolipram promotes remyelination possibly via MEK-ERK signal pathway in cuprizone-induced demyelination mouse", Experimental Neurology, 2012, pp. 304-311, 237(2).

Hess, A., et al., "Blockade of TNF-α rapidly inhibits pain responses in the central nervous system", Proceedings of the National Academy of Sciences of the United States of American, Mar. 1, 2011, pp. 3731-3736, 108(9).

Schafer, Peter, et al., "Apremilast mechanism of action and application to psoriasis and psoriatic arthritis", Biochemical Pharmacology, Jun. 15, 2012, pp. 1583-1590, 83(12).

Schmidt, A., et al., "BDNF and PDE4, but not the GRPR, Regulate Viability of Human Medulloblastoma Cells", Journal of Molecular Neuroscience, Mar. 2010, pp. 303-310, 40(3).

Marquette, A., et al., "ERK and PDE4 cooperate to induce RAF isoform switching in melanoma", Nature Structural & Molecular Biology, May 2011, pp. 584-591, 18(5).

Kim, D. H., et al., "Type 4 Cyclic Adenosine Monophosphate Phosphodiesterase as a Therapeutic Target in Chronic Lymphocytic Leukemia", Blood Journal of the American Society of Hematology, Oct. 1, 1998, pp. 2484-2494, 92 (7).

Vollert, S., et al., "The glucose-lowering effects of the PDE4 inhibitors roflumilast and roflumilast-N-oxide in db/db mice", Diabetologia, Oct. 2012, pp. 2779-2788, 55(10).

Venable, J., et al., "Preparation and Biological Evaluation of Indole, Benzimidazole, and Thienopyrrole Piperazine Carboxamides: Potent Human Histamine H4 Antagonists", Journal of Medicinal Chemistry, 2005, pp. 8289-8298, vol. 48.

Patriciu, Oana-Irian, et al., "Smiles Rearrangement as a Tool for the Preparation of Dihydrodipyridopyrazines", Organic Letter, 2009, pp. 5502-5505, vol. 11.

Seeger, T. F., et al., "Immunohistochemical localization of PDE10A in the rat brain", Brain Research, Sep. 26, 2003, pp. 113-126, 985(2).

Burgin, A.B., et al., "Design of phosphodiesterase 4D (PDE4D) allosteric modulators for enhancing cognition with improved safety", Nature Biotechnology Advance Online Publication, 2010, pp. 63-72, vol. 28.

Schett, G., et al., "Apremilast: A novel PDE4 inhibitor in the treatment of autoimmune and inflammatory diseases", Therapeutic Advances Musculoskeletal Diseases, Aug. 16, 2010, pp. 271-278, 2(5).

Wouters, E.F., et al., "Effect of the Phosphodiesterase 4 Inhibitor Roflumilast on Glucose Metabolism in Patients with Treatment-Naïve, Newly Diagnosed Type 2 Diabetes Mellitus", Journal of Clinical Endocrinology and Metabolism, Sep. 2012, pp. 1720-1725, vol. 97, Abstract Only.

Patan, E., et al., "Efficacy and safety of apremilast, an oral phosphodiesterase 4 inhibitor, in ankylosing spondylitis", Annals of Rheumatic Diseases, Sep. 1, 2013, pp. 1475-1480, 72(9), Abstract Only.

PCT/IB2014/058840, filed Feb. 6, 2014, International Search Report and Written Opinion, mailed Mar. 25, 2014, 13 pages.

Dorange, Ismet, et al., "Discovery of novel pyrrolopyridazine scaffolds as transient receptor potential vanilloid (TRPV1) antagonists", Bioorganic & Medicinal Chemistry Letters, 2012, pp. 6888-6895, vol. 22.

English Translation of Japanese Patent Application Publication No. 8-295667, published Nov. 12, 1996.

* cited by examiner

AZABENZIMIDAZOLE COMPOUNDS

This application is a Non-Provisional application which claims the benefit under 35 U.S.C. 119(e) of U.S. Provisional Patent Application No. 61/766,268, filed on Feb. 19, 2013, the disclosure of which is hereby incorporated by reference in its entirety.

FIELD OF THE INVENTION

The present invention relates to azabenzimidazole compounds of formula I, which are inhibitors of PDE4 isozymes, especially with a binding affinity for the PDE4B isoform, and to the use of such compounds in methods for treating certain central nervous system (CNS), metabolic, autoimmune and inflammatory diseases or disorders.

BACKGROUND OF THE INVENTION

Phosphodiesterases (PDEs) are a class of intracellular enzymes involved in the hydrolysis of the nucleotide cyclic adenosine monophosphate (cAMP) into adenosine 5'-monophosphate (AMP). The cyclic nucleotide cAMP is synthesized by adenylyl cyclase, and serves as a secondary messenger in various cellular pathways.

cAMP functions as a second messenger regulating many intracellular processes within the body. An example is in the neurons of the central nervous system, where the activation of cAMP-dependent kinases and the subsequent phosphorylation of proteins is involved in acute regulation of synaptic transmission as well as neuronal differentiation and survival. The complexity of cyclic nucleotide signaling is indicated by the molecular diversity of the enzymes involved in the synthesis and degradation of cAMP. There are at least ten families of adenylyl cyclases, and eleven families of phosphodiesterases. Furthermore, different types of neurons are known to express multiple isozymes of each of these classes, and there is good evidence for compartmentalization and specificity of function for different isozymes within a given neuron.

A principal mechanism for regulating cyclic nucleotide signaling is via phosphodiesterase-catalyzed cyclic nucleotide catabolism. The 11 known families of PDEs are encoded by 21 different genes; each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE isozymes may offer particular therapeutic effects, fewer side effects, or both (Deninno, M., *Future Directions in Phosphodiesterase Drug Discovery*. Bioorganic and Medicinal Chemistry Letters 2012, 22, 6794-6800).

The present invention relates to compounds having a binding affinity for the fourth family of PDEs (i.e., PDE4A, PDE4B, PDE4C, and PDE4D), and, in particular, a binding affinity for the PDE4B isoform. In addition to affinity for the PDE4B isoform, the compounds of the present invention also have affinity for the PDE4A and PDE4C isoforms.

The PDE4 isozymes are characterized by selective, high-affinity hydrolytic degradation of the second messenger cyclic adenosine 3',5'-monophosphate (cAMP), and by sensitivity to inhibition by Rolipram™ (Schering AG); beneficial pharmacological effects resulting from that inhibition have been shown in a variety of disease models. A number of other PDE4 inhibitors have been discovered in recent years. For example, Roflumilast (Daliresp®), marketed by Forest Pharmaceuticals, Inc., is approved for severe chronic obstructive pulmonary disease (COPD) to decrease the number of flare-ups or the worsening of COPD symptoms (exacerbations). Apremilast (Celgene Corp.) is in Phase III development and clinical trials have shown apremilast to be effective for the treatment of psoriasis (Papp, K. et al., *Efficacy of apremilast in the treatment of moderate to severe psoriasis: a randomized controlled trial*. Lancet 2012; 380(9843):738-46).

While beneficial pharmacological activity of PDE4 inhibitors has been shown, a common side-effect of these treatments has been the induction of gastrointestinal side effects such as nausea, emesis, and diarrhea, which is currently believed to be associated with inhibition of the PDE4D isoform. Attempts were made to develop compounds with an affinity for the PDE4B isoform over the PDE4D isoform (See: Donnell, A. F. et al., *Identification of pyridazino[4,5-b]indolizines as selective PDE4B inhibitors*. Bioorganic & Medicinal Chemistry Letters 2010; 20:2163-7; and Naganuma, K. et al., *Discovery of selective PDE4B inhibitors*. Bioorganic & Medicinal Chemistry Letters 2009; 19:3174-6). However, there remains a need to develop PDE4 inhibitors, especially those having an affinity for the PDE4B isoform. In particular, there remains a need to develop compounds that have enhanced binding affinity for the PDE4B isoform over the PDE4D isoform for the treatment of various diseases and disorders of the central nervous system (CNS). The discovery of selected compounds of the present invention addresses this continued need, and provides additional therapies for the treatment of various diseases and disorders of the central nervous system (CNS), as well as metabolic, autoimmune and inflammatory diseases or disorders. Such diseases and disorders include, but are not limited to, neurodegenerative or psychiatric disorders, including psychosis, impaired cognition, schizophrenia, anxiety, depression (e.g., major depressive disorder), dementia, Alzheimer's disease, Huntington's disease, multiple sclerosis, muscular dystrophy, sickle cell disease and diabetes.

Treatment with the PDE4B inhibitors of the present invention may also lead to a decrease in gastrointestinal side effects (e.g., nausea, emesis and diarrhea) believed to be associated with inhibition of the PDE4D isoform (Robichaud, A. et al., *Deletion of Phosphodiesterase 4D in Mice Shortens α2-Adrenoreceptor-Mediated Anesthesia, A Behavioral Correlate of Emesis*. Journal of Clinical Investigation 2002, Vol. 110, 1045-1052).

In addition to the development of compounds having affinity for the PDE4B isoform, there remains a need to develop compounds having an affinity for the PDE4A and PDE4C isoforms. The discovery of selected compounds of the present invention having affinity for the PDE4A and PDE4C isoforms also provides for the treatment of various diseases and disorders of the central nervous system (CNS), as well as treatment for various metabolic, autoimmune and inflammatory diseases or disorders.

SUMMARY OF THE INVENTION

The present invention is directed to compounds of formula I:

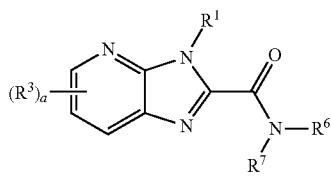

or a pharmaceutically acceptable salt thereof, wherein:

$R^1$ is represented by a substituent selected from the group consisting of $(C_3-C_{10})$cycloalkyl, a (4- to 10-membered)heterocycloalkyl, $(C_6-C_{10})$aryl, and a (5- to 10-membered) heteroaryl; wherein said $(C_3-C_{10})$cycloalkyl, $(C_6-C_{10})$aryl and (5- to 10-membered)heteroaryl are optionally substituted with $(R^2)_b$; and said (4- to 10-membered)heterocycloalkyl is optionally substituted at one to five carbon atoms with a substituent independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, —C(O)NR$^4$R$^5$, hydroxy, and cyano, and optionally substituted at each available nitrogen with $(C_1-C_6)$alkyl;

$R^2$ is represented by a substituent independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, —C(O)NR$^4$R$^5$, hydroxy, and cyano;

$R^3$, if present, at each occurrence is represented by a substituent independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, —C(O)NR$^4$R$^5$, hydroxy, and cyano;

$R^4$ and $R^5$ are each represented by a substituent independently selected from the group consisting of hydrogen, $(C_1-C_6)$alkyl, and $(C_3-C_6)$cycloalkyl;

$R^6$ and $R^7$ are each represented by a substituent independently selected from the group consisting of hydrogen, $(C_1-C_6)$alkyl, —(CH$_2$)$_m$—(C$_3$-C$_{10}$)cycloalkyl, —(CH$_2$)$_m$-(4- to 10-membered) heterocycloalkyl, —(CH$_2$)$_m$—(C$_6$-C$_{10}$)aryl, and —(CH$_2$)$_m$-(5- to 10-membered)heteroaryl; wherein said $(C_1-C_6)$alkyl, $(C_3-C_{10})$cycloalkyl, $(C_6-C_{10})$aryl, and (5- to 10-membered)heteroaryl are optionally substituted with one to five substituents independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, —C(O)NR$^4$R$^5$, hydroxy, and cyano; and said (4- to 10-membered) heterocycloalkyl is optionally substituted at one to five carbon atoms with a substituent independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, —C(O)NR$^4$R$^5$, hydroxy, and cyano, and optionally substituted at each available nitrogen with $(C_1-C_6)$alkyl; or $R^6$ and $R^7$ taken together with the nitrogen to which they are attached form a (4- to 10-membered)heterocycloalkyl, wherein said (4- to 10-membered)heterocycloalkyl is optionally substituted at one to five carbon atoms with a substituent independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, —C(O)NR$^4$R$^5$, hydroxy, and cyano;

a is represented by an integer selected from 0, 1, 2 or 3;

b is represented by an integer selected from 0, 1, 2, 3, 4 or 5; and m is represented by an integer selected from 0, 1, 2, or 3.

Compounds of the invention include Examples 1-92 or a pharmaceutically acceptable salt thereof as described herein.

The compounds of formula I are inhibitors of the PDE4B isoform.

In addition, the compounds of formula I are inhibitors of the PDE4A and PDE4C isoforms.

The compounds of formula I are useful for treating or preventing neurodegenerative or psychiatric disorders, including, but not limited to, cognitive dysfunction, psychosis, schizophrenia, depression, dementia, anxiety, bipolar affective disorder, Parkinson's disease, Alzheimer's disease (AD), Huntington's disease (HD), multiple sclerosis (MS), and neuroinflammatory disorders as well as a host of other diseases or disorders in a mammal associated with PDE4B isoform activity. Additional diseases and disorders include, but are not limited to, pain, cancer, immunodeficiency diseases (e.g., psoriasis and arthritis), inflammation, asthma, chronic obstructive pulmonary disease (COPD), diabetes, muscular dystrophy, sickle cell disease, cardiovascular diseases, cerebral vascular disease, stroke and allergic conjunctivitis.

The present invention is also directed to the use of a compound of the present invention, or a pharmaceutically acceptable salt thereof, in the preparation of a medicament for the treatment or prevention of a condition amenable to modulation of the PDE4B gene family (i.e., PDE4B enzymes) which consists of various splice variants such as PDE4B1, B2, B3, PDE4B4, and B5 protein. Examples of conditions include, but are not limited to, cognitive dysfunction, psychosis, schizophrenia, depression, dementia, anxiety, bipolar affective disorder, Parkinson's disease, Alzheimer's disease (AD), Huntington's disease (HD), multiple sclerosis (MS), and neuroinflammatory disorders as well as a host of other diseases or disorders in a mammal associated with PDE4B isoform activity, such as, but not limited to, pain, cancer, immunodeficiency diseases (e.g., psoriasis and arthritis), inflammation, asthma, chronic obstructive pulmonary disease (COPD), diabetes, muscular dystrophy, sickle cell disease, cardiovascular diseases, cerebral vascular disease, stroke and allergic conjunctivitis.

The present invention is also directed to pharmaceutically acceptable formulations containing an admixture of a compound(s) of the present invention and at least one excipient formulated into a pharmaceutical dosage form. Examples of such dosage forms include tablets, capsules, solutions/suspensions for injection, aerosols for inhalation and solutions/suspensions for oral ingestion.

DETAILED DESCRIPTION OF THE INVENTION

The headings within this document are only being utilized to expedite its review by the reader. They should not be construed as limiting the invention or claims in any manner.

Definitions and Exemplifications

As used throughout this application, including the claims, the following terms have the meanings defined below, unless specifically indicated otherwise. The plural and singular should be treated as interchangeable, other than the indication of number:

"$(C_1-C_6)$alkyl" as used herein, refers to a branched- or straight-chain alkyl group containing from 1 to 6 carbon atoms, such as, but not limited to, methyl, ethyl, n-propyl, isopropyl, n-butyl, sec-butyl, isobutyl, tert-butyl, n-pentyl, isopentyl, neopentyl, and n-hexyl.

"halo" or "halogen" as used herein, refers to a chlorine, fluorine, bromine, or iodine atom.

"halo($C_1$-$C_6$)alkyl" as used herein, refers to a ($C_1$-$C_6$)alkyl group, as defined above, wherein at least one hydrogen atom is replaced with a halogen, as defined above. Representative examples of a halo($C_1$-$C_6$)alkyl include, but are not limited to, chloromethyl, 2-fluoroethyl, trifluoromethyl, pentafluoroethyl, and 2-chloro-3-fluoropentyl.

"($C_1$-$C_6$)alkoxy" as used herein, refers to a ($C_1$-$C_6$)alkyl group, as defined above, attached to the parent molecular moiety through an oxygen atom. Representative examples of a ($C_1$-$C_6$)alkoxy include, but are not limited to, methoxy, ethoxy, propoxy, 2-propoxy, butoxy, tert-butoxy, pentyloxy, and hexyloxy.

"halo($C_1$-$C_6$)alkoxy" as used herein, refers to a ($C_1$-$C_6$)alkoxy group, as defined above, wherein at least one hydrogen atom is replaced with a halogen, as defined above. Representative examples of a halo($C_1$-$C_6$)alkoxy include, but are not limited to, chloromethoxy, 2-fluoroethoxy, trifluoromethoxy, and pentafluoroethoxy.

"thio" as used herein, means —S (sulfur).

"($C_1$-$C_6$)alkylthio" as used herein, means a ($C_1$-$C_6$)alkyl group, as defined herein, attached to the parent molecular moiety through a sulfur atom. Representative examples of a ($C_1$-$C_6$)alkylthio include, but are not limited to, methylthio, ethylthio, propylthio, and butylthio.

"($C_3$-$C_{10}$)cycloalkyl" as used herein, refers to a saturated or partially saturated monocyclic, bicyclic, bridged bicyclic or tricyclic alkyl radical wherein the cyclic framework has 3 to 10 carbons. Examples of monocyclics include cyclopropyl, cyclobutyl, cyclopentyl, cyclohexyl, cycloheptyl, cyclooctyl, cyclononyl and cyclodecyl. Alternatively, a cycloalkyl may be a bicyclic ring such as a bicycloalkyl. The bicycloalkyl may be a fused system, such as bicyclo[1.1.0]butane, bicyclo[2.1.0]pentane, bicyclo[2.2.0]hexane, bicyclo[3.1.0]hexane, bicyclo[3.2.0]heptane, and bicyclo[3.3.0]octane. The term "bicycloalkyl" also includes bridged bicycloalkyl systems such as, but not limited to, bicyclo[2.2.1]heptane and bicyclo[1.1.1]pentane. The cycloalkyl may also be a bicyclic ring such that a monocyclic ring is fused to an aryl or heteroaryl ring. In this case, a group having such a fused cycloalkyl group as a substituent is bound to a carbon atom of the saturated or partially saturated ring. For example, a cycloalkyl moiety may include, but is not limited to, 2,3-dihydro-1H-inden-2-yl.

"heterocycloalkyl," as used herein, refers to a substituent obtained by removing a hydrogen from a saturated or partially saturated ring structure, wherein at least one of the ring atoms is a heteroatom selected from oxygen, nitrogen or sulfur. For example, as used herein, the term "(4- to 6-membered)heterocycloalkyl" means the substituent contains a total of 4 to 6 ring atoms. A "(4- to 10-membered)heterocycloalkyl" means the substituent contains a total of 4 to 10 ring atoms. A heterocycloalkyl may be a single ring with up to 10 total members. Alternatively, a heterocycloalkyl as defined above may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is attached to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "heterocycloalkyl" also includes substituents that are fused to a $C_6$-$C_{10}$ aromatic ring or a (5- to 10-membered) heteroaromatic ring, wherein a group having such a fused heterocycloalkyl group as a substituent is bound to a heteroatom of the heterocycloalkyl group or to a carbon atom of the heterocycloalkyl group. When such a fused heterocycloalkyl group is substituted with one or more substituents, the one or more substituents, unless otherwise specified, are each bound to a heteroatom of the heterocycloalkyl group or to a carbon atom of the heterocycloalkyl group. The fused $C_6$-$C_{10}$ aromatic ring or a (5- to 10-membered)heteroaromatic ring may be optionally substituted with halogen, ($C_1$-$C_6$)alkyl, ($C_3$-$C_{10}$)cycloalkyl, ($C_1$-$C_6$)alkoxy or =O. Examples of heterocycloalkyl substituents include, but are not limited to, tetrahydroquinolyl, dihydrobenzofuryl and the like. Other heterocycloalkyl rings include: azetidinyl, dihydrofuranyl, tetrahydropyranyl, dihydrothiophenyl, pyrrolidinyl, tetrahydrofuranyl, tetrahydrothiophenyl, piperidinyl, piperazinyl, azepane, azocane, morpholinyl, isochromyl, tetrahydrotriazine, tetrahydropyrazole, dihydro-1H-isoindole, tetrahydrooxazolyl, tetrahydro-oxazinyl, thiomorpholinyl, tetrahydropyrimidinyl, octahydrobenzofuranyl, octahydrobenzimidazolyl, and octahydrobenzothiazolyl.

"($C_6$-$C_{10}$)aryl" refers to an aromatic substituent containing from 6 to 10 carbon atoms, including one ring or two fused rings such as phenyl, or naphthyl. The term "aryl" also includes substituents such as phenyl and naphthyl that are fused to a ($C_4$-$C_6$)cycloalkyl or ($C_4$-$C_{10}$)heterocycloalkyl, wherein a group having such a fused aryl group as a substituent is bound to an aromatic carbon of the aryl group. When such an aryl group is substituted with one or more substituents, the one or more substituents, unless otherwise specified, are each bound to an aromatic carbon of the fused aryl group. The fused ($C_3$-$C_6$)cycloalkyl or ($C_4$-$C_{10}$)heterocycloalkyl ring may be optionally substituted with halogen, ($C_1$-$C_6$)alkyl, ($C_3$-$C_{10}$)cycloalkyl, or =O. Examples of aryl groups include, but are not limited to, phenyl, naphthyl, indanyl (e.g., 2,3-dihydro-1H-inden-5-yl), indenyl and dihydrobenzofuranyl (e.g., 1,3-dihydro-2-benzofuran-5-yl).

"(5- to 10-membered)heteroaryl" refers to an aromatic ring having from 5 to 10 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. In a group that has a heteroaryl substituent, the ring atom of the heteroaryl substituent that is bound to the group may be the at least one heteroarom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroarom, or it may be bound to a ring carbon atom, where the ring carbon atom may be in the same ring as the at least one heteroatom, or where the ring carbon atom may be in a different ring from the at least one heteroatom.

The term "heteroaryl" also includes substituents such as pyridyl and triazolyl that are fused to a ($C_4$-$C_{10}$)cycloalkyl group, or to a (4- to 10-membered)heterocycloalkyl group, wherein a group having such a fused heteroaryl group as a substituent is bound to an aromatic carbon of the heteroaryl group or to a heteroatom of the heteroaryl group. When such a fused heteroaryl group is substituted with one or more substituents, the one or more substituents, unless otherwise specified, are each bound to an aromatic carbon of the heteroaryl group or to a heteroatom of the heteroaryl group. The fused ($C_4$-$C_{10}$)cycloalkyl group or (4- to 10-membered)heterocycloalkyl group may be optionally substituted with halogen, ($C_1$-$C_6$)alkyl, ($C_3$-$C_{10}$)cycloalkyl, or =O. Examples of heteroaryls include, but are not limited to, 6-membered ring substituents such as pyridyl, pyrazyl, pyrimidinyl and pyridazinyl; 5-membered heteroaryls such as triazolyl, imidazolyl, furanyl, isoxazolyl, isothiazolyl, 1,2,3-, 1,2,4-, 1,2, 5-, or 1,3,4-oxadiazolyl, oxazolyl, thiophenyl, thiazolyl, and pyrazolyl. Representative examples of bicyclic heteroaryls include, but are not limited to, benzimidazolyl, benzofuranyl, benzothienyl, benzoxadiazolyl, benzothiazolyl (e.g., 1,3-benzothiazol-6-yl and 2-methyl-1,3-benzothiazol-6-yl), benzothiofuranyl, isobenzothiofuranyl, benzisoxazolyl, benzoxazolyl, 1,4-benzoxazinyl, cinnolinyl, furopyridinyl, indazolyl, indolyl, isoquinolinyl, naphthyridinyl, purinyl, quinolinyl, quinazolinyl, 5,6,7,8-tetrahydroquinolinyl, thienopyridinyl, and triazolopyridinyl (e.g., 5,6,7,8-tetrahydro[1,2,4]triazolo[1,5-a]pyridin-2-yl).

"hydroxy" or "hydroxyl" as used herein, means an —OH group.

"cyano" as used herein, means a —CN group, which also may be depicted:

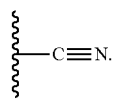

"optionally substituted" as used herein, means that substitution is optional and therefore includes both unsubstituted and substituted atoms and moieties. A "substituted" atom or moiety indicates that any hydrogen on the designated atom or moiety can be replaced with a selection from the indicated substituent group (up to and including that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., $CH_3$) is optionally substituted, then up to 3 hydrogen atoms on the carbon atom can be replaced with substituent groups.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable (i.e., bonded to one or more hydrogen atoms). For example, as shown in formula Ia below, $R^2$ may be bonded to any ring-forming atom that is substitutable (i.e., bonded to one or more hydrogen atoms).

"Therapeutically effective amount" refers to that amount of the compound being administered which will relieve to some extent one or more of the symptoms of the disorder being treated.

"Patient" refers to warm blooded animals such as, for example, pigs, cows, chickens, horses, guinea pigs, mice, rats, gerbils, cats, rabbits, dogs, monkeys, chimpanzees, and humans.

"Treating" or "treat", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Pharmaceutically acceptable" indicates that the substance or composition must be compatible, chemically and/or toxicologically, with the other ingredients comprising a formulation, and/or the mammal being treated therewith.

"Isoform" means any of several different forms of the same protein.

"Isozyme" or "isoenzyme" means a closely related variant of an enzyme that differs in amino acid sequence but catalyzes the same chemical reaction.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

This specification uses the terms "substituent," "radical," and "group" interchangeably.

If substituents are described as being "independently selected" from a group, each instance of a substituent is selected independent of the other. Each substituent therefore may be identical to or different from the other substituent(s).

As used herein the terms "formula I" and "formula Ia" may be hereinafter referred to as a "compound(s) of the invention." Such terms are also defined to include all forms of the compound of formulas I, and Ia, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (-), a solid wedge ( ▬ ) or a dotted wedge ( ·····||||| ) The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry are marked with (+/−). For example, unless stated otherwise, it is intended that the compounds of the invention can exist as stereoisomers, which include cis and trans isomers, optical isomers such as R and S enantiomers, diastereomers, geometric isomers, rotational isomers, conformational isomers, atropoisomers, and mixtures thereof (such as racemates and diastereomeric pairs). The compounds of the invention may exhibit more than one type of isomerism. Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the present invention with an acid whose anion, or a base whose cation, is generally considered suitable for human consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as, but not limited to, hydrochloric, hydrobromic, hydrofluoric, boric, fluoroboric, phosphoric, meta-phosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylamino-ulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalene-sulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanol-amine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulphate and hemicalcium salts.

Certain compounds of the invention may exist as geometric isomers. The compounds of the invention may possess one or more asymmetric centers, thus existing as two, or more, stereoisomeric forms. The present invention includes all the individual stereoisomers and geometric isomers of the compounds of the invention and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e., polymorphs, or they may exist as amorphous solids. All such forms are encompassed by the claims.

Also within the scope of the present invention are so-called "prodrugs" of the compound of the invention. Thus, certain derivatives of the compound of the invention that may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and W. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of the present invention with certain moieties known to those skilled in the art as "promoieties" as described, for example, in "Design of Prodrugs" by H. Bundgaard (Elsevier, 1985).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes all pharmaceutically acceptable isotopically-labeled compounds, which are identical to those recited in formulas I and Ia, wherein one or more atoms are replaced by an atom having the same atomic number, but an atomic mass or mass number different from the atomic mass or mass number which predominates in nature. Examples of isotopes suitable for inclusion in the compounds of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically-labeled compounds of the present invention, for example, those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron emitting isotopes, such as $^{11}$C, $^{15}$F, $^{15}$O and $^{13}$N, can be useful in positron emission tomography (PET) studies for examining substrate receptor occupancy. Isotopically-labeled compounds of the present invention can generally be prepared by conventional techniques known to those skilled in the art or by processes analogous to those described in the accompanying Schemes and/or in the Examples and Preparations using an appropriate isotopically-labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$. Compounds of formula I and formula Ia, as well as the compounds exemplified in Examples 1-92 described below, include isotopically-labeled versions of these compounds, such as, but not limited to, the deuterated and tritiated isotopes and all other isotopes discussed above.

Compounds

The present invention is directed to azabenzimidazole compounds of formula I as described above. In certain embodiments, the pyridine ring of the imidazopyridine core does not contain any substitutions on the ring. In these instances the "a" of the $(R^3)_a$ substituent is represented by the integer 0.

To further elucidate the compounds of the present invention, the following subgenus is described below.

Formula Ia depicted below is a subset of formula I as depicted, wherein $R^1$ is represented by a phenyl optionally substituted with $(R^2)_b$; and a is represented by the integer 0. In formula Ia, b is represented by an integer selected from 0, 1, 2, or 3; each $R^2$, if present, is represented by a substituent independently selected from the group consisting of fluoro, chloro, cyano, methyl, trifluoromethyl, methylthio, methoxy, and trifluoromethoxy; $R^6$ and $R^7$ are each independently selected from the group consisting of hydrogen, ($C_1$-$C_6$)alkyl, —$(CH_2)_m$—($C_3$-$C_{10}$)cycloalkyl, and —$(CH_2)_m$-(5- to 10-membered)heteroaryl, wherein said ($C_1$-$C_6$)alkyl, ($C_3$-$C_{10}$)cycloalkyl, and (5 to 10-membered)heteroaryl are optionally substituted with one to three substituents independently selected from the group consisting of halogen, ($C_1$-$C_6$) alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy, and cyano; or $R^6$ and $R^7$ taken together with the nitrogen to which they are attached form a (4- to 6-membered)heterocycloalkyl, wherein said heterocycloalkyl is optionally substituted at one to three carbon atoms with a substituent independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy, and cyano; wherein $R^4$ and $R^5$ are each independently selected from the group consisting of hydrogen and ($C_1$-$C_6$)alkyl; and m is represented by an integer 0, 1, or 2:

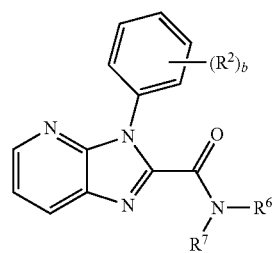

Ia

In certain embodiments of the invention, in formula Ia as depicted above, b is represented by an integer selected from 0, 1, 2, or 3; each $R^2$, if present, is represented by a substituent independently selected from the group consisting of chloro, fluoro, methyl and cyano; one of $R^6$ and $R^7$ is represented by hydrogen, and the other is represented by a substituent selected from the group consisting of ($C_1$-$C_6$)alkyl, —$(CH_2)_m$—($C_3$-$C_{10}$)cycloalkyl, and —$(CH_2)_m$-(5- to 10-membered)heteroaryl, wherein said ($C_1$-$C_6$)alkyl, ($C_3$-$C_{10}$)cycloalkyl, and (5 to 10-membered)heteroaryl are optionally substituted with one to three substituents independently selected from the group consisting of halogen, ($C_1$-$C_6$) alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy, and cyano.

In certain embodiments of the invention, in formula Ia as depicted above, b is an integer selected from 0, 1, 2, or 3; each $R^2$, if present, is represented by a substituent independently selected from the group consisting of chloro, fluoro, methyl, and cyano; one of $R^6$ and $R^7$ is represented by hydrogen, and the other is represented by ($C_1$-$C_6$)alkyl optionally substituted with one to three substituents independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, hydroxy, and cyano. In certain embodiments, one of $R^6$ and $R^7$ is represented by hydrogen, and the other is represented by a substituent selected from the group consisting of ethyl and propyl. In certain embodiments, one of $R^6$ and $R^7$ is represented by hydrogen, and the other is represented by propyl.

In certain other embodiments of the invention, in formula Ia as depicted above, b is represented by an integer selected from 0, 1, 2, or 3; each $R^2$, if present, is represented by a substituent independently selected from the group consisting of chloro, fluoro, methyl, and cyano; one of $R^6$ and $R^7$ is represented by hydrogen, and the other is represented by —$(CH_2)_m$—($C_3$-$C_{10}$)cycloalkyl optionally substituted with one to three substituents independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, hydroxy, and cyano; and m is represented by an integer selected from 0, 1, or 2. In certain embodiments, one of $R^6$ and $R^7$ is represented by hydrogen, and the other is represented by cyclopropyl.

In certain other embodiments of the invention, in formula Ia as depicted above, b is represented by an integer selected from 0, 1, 2, or 3; each $R^2$, if present, is represented by a substituent independently selected from the group consisting of chloro, fluoro, methyl, and cyano; one of $R^6$ and $R^7$ is represented by hydrogen, and the other is represented by —$(CH_2)_m$-(5- to 10-membered)heteroaryl optionally substituted with one to three substituents independently selected from the group consisting of halogen, $(C_1$-$C_6)$alkyl, halo$(C_1$-$C_6)$alkyl, $(C_1$-$C_6)$alkoxy, halo$(C_1$-$C_6)$alkoxy, $(C_1$-$C_6)$alkylthio, hydroxy, and cyano, wherein m is represented by an integer selected from 0, 1, or 2. In certain embodiments, one of $R^6$ and $R^7$ is represented by hydrogen, and the other is represented by pyrazolyl optionally substituted by a $(C_1$-$C_6)$ alkyl. In certain embodiments, one of $R^6$ and $R^7$ is represented by hydrogen, and the other is represented by N-methylpyrazolyl (e.g., N-methylpyrazol-3-yl).

In certain embodiments of the invention, in formula Ia, b is represented by an integer selected from 0, 1, 2, or 3; each $R^2$, if present, is represented by a substituent independently selected from the group consisting of fluoro, chloro, cyano, methyl, trifluoromethyl, methylthio, methoxy, and trifluoromethoxy; $R^6$ and $R^7$ taken together with the nitrogen to which they are attached form a (4- to 6-membered)heterocycloalkyl optionally substituted at one to three carbon atoms with a substituent independently selected from the group consisting of halogen, $(C_1$-$C_6)$alkyl, halo$(C_1$-$C_6)$alkyl, $(C_1$-$C_6)$alkoxy, halo$(C_1$-$C_6)$alkoxy, $(C_1$-$C_6)$alkylthio, —C(O)$NR^4R^5$, hydroxy, and cyano, wherein $R^4$ and $R^5$ are each independently selected from the group consisting of hydrogen and $(C_1$-$C_6)$alkyl.

In certain other embodiments of the invention, in formula Ia as depicted above, b is represented by an integer selected from 0, 1, 2, or 3; each $R^2$, if present, is represented by a substituent independently selected from the group consisting of chloro, fluoro, methyl and cyano; and $R^6$ and $R^7$ taken together with the nitrogen to which they are attached form an azetidine ring optionally substituted with one to three halogen. In certain embodiments $R^6$ and $R^7$ taken together with the nitrogen to which they are attached form 3-fluoro-azetidin-1-yl.

In another embodiment, selected compounds of the present invention may be useful for treating a PDE4B-mediated disorder, comprising administering to a mammal (preferably a human) in need thereof a therapeutically effective amount of a compound of the invention effective in inhibiting PDE4B activity; more preferably, administering an amount of a compound of the invention having improved binding affinity for PDE4B while at the same time possessing less inhibitory activity toward PDE4D.

In another embodiment, selected compounds of the present invention may be useful for treating a PDE4A-mediated disorder, comprising administering to a mammal (preferably a human) in need thereof a therapeutically effective amount of a compound of the invention effective in inhibiting PDE4A activity.

In yet another embodiment, selected compounds of the present invention may be useful for treating a PDE4C-mediated disorder, comprising administering to a mammal (preferably a human) in need thereof a therapeutically effective amount of a compound of the invention effective in inhibiting PDE4C activity.

In certain other embodiments, selected compounds of the present invention may exhibit a binding affinity for the PDE4A, PDE4B and PDE4C isoforms or combinations thereof.

In certain embodiments, the compounds of the present invention have an enhanced binding affinity for the PDE4B isoform over the PDE4D isoform such that the compounds display about a 2-fold to about a 120-fold binding affinity for the PDE4B isoform over the PDE4D isoform. In certain other embodiments, the compounds of the present invention display about a 35-fold to about a 75-fold binding affinity for the PDE4B isoform over the PDE4D isoform. In certain embodiments, the compounds of the present invention display at least about a 2-fold binding affinity for the PDE4B isoform over the PDE4D isoform. In certain embodiments, the compounds of the present invention display at least about a 5-fold binding affinity for the PDE4B isoform over the PDE4D isoform. In certain embodiments, the compounds of the present invention display at least about a 10-fold binding affinity for the PDE4B isoform over the PDE4D isoform. In certain embodiments, the compounds of the present invention display at least about a 20-fold binding affinity for the PDE4B isoform over the PDE4D isoform. In certain other embodiments, the compounds of the present invention display at least about a 40-fold binding affinity for the PDE4B isoform over the PDE4D isoform. In certain other embodiments, the compounds of the present invention display at least about a 50-fold binding affinity for the PDE4B isoform over the PDE4D isoform. The binding affinities of the compounds of the present invention for the PDE4B and PDE4D isoforms are shown in Table 4 of the Experimental Section below.

In another embodiment, the present invention provides a pharmaceutical composition comprising a compound of the present invention, or a pharmaceutically acceptable salt thereof, in admixture with at least one pharmaceutically acceptable excipient.

In yet another embodiment, administration of the compounds of the present invention to a patient in need thereof may also lead to a decrease in gastrointestinal discomfort such as emesis, diarrhea, and nausea, which is currently believed to be associated with administration of compounds having binding affinity for other PDE4 isoforms, especially the PDE4D isoform, resulting in an increase in patient compliance as well as overall treatment outcome.

In another embodiment, the present invention provides a method of treating central nervous system (CNS), metabolic, autoimmune and inflammatory diseases or disorders. Comprising administering to the mammal, particularly a human, in need of such treatment a therapeutically effect amount of a compound of the present invention, or a pharmaceutically acceptable salt thereof.

In another embodiment, the present invention provides the use of a compound of the present invention, or a pharmaceutically acceptable salt thereof, in the manufacture of a medicament for treating central nervous system (CNS), autoimmune and inflammatory diseases or disorders.

Pharmacology

Phosphodiesterases (PDEs) of the PDE4 family are characterized by selective, high-affinity hydrolytic degradation of the second messenger cyclic nucleotide, adenosine 3',5'-cyclic monophosphate (cAMP). The PDE4A, PDE4B and PDE4D subtypes are known to be widely expressed throughout the brain, with regional and intracellular distribution for the PDE4A, PDE4B and PDE4D subtypes being distinct, whereas the PDE4C subtype is expressed at lower levels throughout the central nervous system (See; Siuciak, J. A. et al., *Antipsychotic profile of rolipram: efficacy in rats and* reduced sensitivity in mice deficient in the phosphodiesterase-4B (PDE4B) enzyme, Psychopharmacology (2007) 192:415-424). The location of the PDE4 subtypes makes them an interesting target for exploring new treatments for central nervous system diseases and disorders. For example, PDE4B has been identified as a genetic susceptibility factor for schizophrenia (See: Millar, J. K. et al., *Disrupted in schizophrenia 1 and phosphodiesterase 4B: towards an understanding of psychiatric illness*, J. Physiol. 584 (2007) pp. 401-405).

The PDE4 inhibitor rolipram has been shown to be useful in treating or reversing Aβ-induced memory deficits via the attenuation of neuronal inflammation and apoptosis-mediated cAMP/CREB signaling, and is a potential target for treatment of cognitive deficits associated with AD. (See: Wang, C. et al., *The phosphodiesterase-4 inhibitor rolipram reverses Aβ-induced cognitive impairment and neuroinflammatory and apoptotic responses in rats*, International Journal of Neuropsychopharmacology (2012), 15, 749-766).

PDE4 inhibitors have also been shown to possess antidepressant effects by decreasing brain levels of PDE4 in individuals with major depressive disorder (MDD) (See: Fujita, M. et al., *C—(R-)-Rolipram Positron Emission Tomography in Major Depressive Disorder*, Biological Psychiatry, 71, 2012, 548-554).

Furthermore, PDE4 inhibitors have been shown to possess therapeutic activity with implications for the treatment of multiple sclerosis (See: Sun, X. et al., *Rolipram promotes remyelination possibly via MEK-ERK signal pathway in cuprizone-induced demyelination mouse*, Experimental Neurology 2012; 237:304-311).

In view of the above, in certain embodiments, the compounds of the present invention have a wide range of therapeutic applications for the treatment of conditions or diseases of the central nervous system including, but not limited to, Niemann-Pick type C; Batten Disease; neurological disorders (such as headache, migraine; epilepsy; Alzheimer's disease; Parkinson's disease; brain injury (TBI); stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorders (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, premenstrual syndrome (PMS) premenstrual dysphoric disorder (PDD), and postpartum depression); psychomotor disorders; psychotic disorders (including schizophrenia, schizoaffective disorder, schizophreniform, and delusional disorder); drug dependence and abuse (including narcotic dependence, alcoholism, amphetamine and methamphetamine dependence, opioid dependence, cocaine addiction, nicotine dependence, and drug withdrawal syndrome, and relapse prevention); eating disorders (including anorexia, bulimia, binge eating disorder, hyperphagia, obesity, compulsive eating disorders and pagophagia); sexual dysfunction disorders, urinary incontinence (e.g., bladder overactivity); neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of the present invention or a pharmaceutically acceptable salt thereof.

In certain embodiments, the present invention is directed to methods for the treatment of schizophrenia by administration of a therapeutically effective amount of an azabenzimidazole compound of the present invention to a patient in need thereof.

In certain other embodiments, the invention is further directed to a method for the treatment of cognitive impairment associated with schizophrenia by administration of a therapeutically effective amount of an azabenzimidazole compounds of the present invention to a patient in need thereof.

In addition to the central nervous system disorders mentioned above, there is extensive literature in the art describing the effects of PDE inhibitors on various inflammatory cell responses, which in addition to cAMP increase, include inhibition of superoxide production, degranulation, chemotaxis and tumor necrosis factor (TNF) release in eosinophils, neutrophils and monocytes. Therefore, the azabenzimidazole compounds of the present invention may be useful for treating autoimmune and Inflammatory diseases. (See: Schett, G. et al., *Apremilast: A novel PDE4 Inhibitor in the Treatment of Autoimmune and Inflammatory Diseases*, Ther. Adv. Musculoskeletal Dis. 2010; 2(5):271-278). For example, the compounds of the present invention may be useful for treatment of oral ulcers associated with Behçet's disease (Id.). The compounds of the present invention may also be useful for the treatment of pain associated with arthritis (See: Hess, A. et al., *Blockade of TNF-α rapidly inhibits pain responses in the central nervous system*, PNAS, vol. 108, no. 9, 3731-3736 (2011) or for the treatment of psoriasis or psoriatic arthritis (See: Schafer, P., *Apremilast mechanism of action and application to psoriasis and psoriatic arthritis*, Biochem. Pharmacol. (2012), 15; 83(12):1583-90). Accordingly, the azabenzimidazole compounds of the present invention may also be useful for treatment of ankylosing spondylitis [see: Patan, E. et al., *Efficacy and safety of apremilast, an oral phosphodiesterase 4 inhibitor, in ankylosing spondylitis*, Ann. Rheum. Dis. (Sep. 14, 2102)]. Other conditions treatable by administration of the compounds of the present invention include, but are not limited to, multiple sclerosis, burns, sepsis, asthma, chronic or acute bronchoconstriction, chronic bronchitis, bronchiectasis, small airways obstruction, emphysema, obstructive or inflammatory airways diseases, pneumoconiosis, seasonal allergic rhinitis or perennial allergic rhinitis or sinusitis, allergic conjunctivitis, acute respiratory distress syndrome (ARDS), acute lung injury (ALI), arthritis (e.g., rheumatoid arthritis and osteoarthritis) gout, and fever and pain associated with inflammation, eosinophil-related disorders, dermatitis or eczema, urticaria, conjunctivitis, uveitis, psoriasis, inflammatory bowel disease, Crohn's disease, septic shock, liver injury, pulmonary hypertension, bone loss disease, neuropathy, and infection.

In yet another embodiment, the compounds of the present invention may be useful for treating cancer and tumors. For example, the compounds of the present invention may be useful for treatment of brain cancer (e.g., medulloblastoma) (See: Schmidt, A. L., *BDNF and PDE4, but not GRPR, Regulate Viability of Human Medulloblastoma Cells*, J. Mol. Neuroscience. (2010) 40:303-310). The compounds of the present invention may also be useful for treating melanoma (See: Marquette, A. et al., *ERK and PDE4 cooperate to induce RAF isoform switching in melanoma*, Nature Structural & Molecular Biology, vol. 18, no. 5, 584-91, 2011). In certain embodiments, the compounds of the present invention may be useful for treating leukemia, e.g., chronic lymphocytic leukemia, (See: Kim, D. H. et al., *Type 4 Cyclic Adenosine Monophosphate Phosphodiesterase as a Therapeutic Target in Chronic Lymphocytic Leulemia*, Blood Journal of The American Society of Hematology, Oct. 1, 1998, vol. 92, no. 7 2484-2494).

In certain other embodiments, the compounds of the present invention may be useful for treating diabetes or conditions associated with diabetes (See: Vollert, S. et al., *The glucose-lowering effects of the PDE4 inhibitors roflumilast and roflumilast-N-Oxide in db/db mice*, Diabetologia (2012) 55:2779-2788. Wouters, E. F. M. et al., *Effect of the Phosphodiesterase 4 Inhibitor Roflumilast on Glucose Metabolism in Patients with Treatment-Näive, Newly Diagnosed Type 2 Diabetes Mellitus*, Journal of Clinical Endocrinology and Metabolism 2012, 97, 1720-1725). In certain embodiments, the compounds of the present invention may be useful for treating diabetic macular edema (DME) and diabetic neuropathy (DN).

FORMULATIONS

The compounds of the invention may be administered orally. Oral administration may involve swallowing, so that the compound enters the gastrointestinal tract, or buccal or sublingual administration may be employed by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be formulated such that administration topically to the skin or mucosa (i.e., dermally or transdermally) leads to systemic absorption of the compound. In another embodiment, the compounds of the invention can also be formulated such that administration intranasally or by inhalation leads to systemic absorption of the compound. In another embodiment, the compounds of the invention may be formulated such that administration rectally or vaginally leads to systemic absorption of the compound.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of the present invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions) may be formulated according to the known art using suitable dispersing, wetting, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a PDE4 inhibitor compound of the present invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-β (or fragments thereof), such as $A\beta_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W (3,5-bis (4-nitrophenoxy)benzoic acid), NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenyloin sodium (PHENYTEK), fosphenyloin (CEREBYX, PRODILANTIN), divalproex sodium (DEPAKOTE), gabapentin (NEURONTIN), pregabalin (LYRICA), topiramate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxpine, resperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-3-fluoro-3-(3-fluoro-4-pyrrolidin-1-yl-methyl-phenyl)-cyclobutane carboxylic acid ethylamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-benzyloxy-5-((5-undecyl-2H-pyrrol-2-ylidene)methyl)-2,2'-bi-1H-pyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lanticemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (1-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, viluzole 2,3,4,9-tetrahydro-1H-carbazol-3-one oxime, desmoteplase, anatibant, astaxanthin, neuropeptide NAP (e.g., AL-108 and AL-208; both Alton Therapeutics), neurostrol, perampanel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-β-hydroxyepiandrosterone; Newron Pharmaceuticals), HF-0420 (also known as oligotropin), pyridoxal 5'-phosphate (also known as MC-1), microplasmin, 5-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitor such as 2-[4-(1-Methyl-4-pyridin-4-yl-1H-pyrazol-3-yl)phenoxymethyl] quinoline (PF-2545920), and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, Ac-rER($N^2$-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, ELAN-Z, 4-chloro-N-[2-ethyl-1(S)-(hydroxymethyl)butyl]benzenesulfonamide;

(xxxiii) serotonin (5-hydroxytryptamine) 1A ($5-HT_{1A}$) receptor antagonists, such as spiperone, levo-pindolol, BMY 7378, NAD-299, S(−)-UH-301, NAN 190, lecozotan;

(xxxiv) serotonin (5-hydroxytryptamine) 2C (5-HT2c) receptor agonists, such as vabicaserin, and zicronapine;

(xxxv) serotonin (5-hydroxytryptamine) 4 ($5-HT_4$) receptor agonists, such as PRX-03140 (Epix);

(xxxvi) serotonin (5-hydroxytryptamine) 6 ($5-HT_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3S,4S)-4-[4-(5-cyanothiophen-2-yl)phenoxy]tetrahydrofuran-3-yl}propane-2-sulfonamide, and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

The compounds of the invention, or their pharmaceutically acceptable salts, may be prepared by a variety of methods that are analogously known in the art. The reaction schemes described below, together with synthetic methods known in the art of organic chemistry, or modifications and derivatizations that are familiar to those of ordinary skill in the art, illustrate six (6) methods for preparing the compounds. Others, including modifications thereof, will be readily apparent to one skilled in the art.

The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of the present invention or their pharmaceutically acceptable salts of said compounds or tautomers and radioisotopes, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in some cases, the compounds in Schemes 1 through 6 will be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1 below illustrates one synthesis sequence for the preparation of compounds of formula I. The initial step in the synthesis, as depicted, utilizes 2-chloro-3-nitropyridine of formula 1 as an initial starting material. The 2-chloro-3-nitropyridine 1 undergoes $S_NAr$ reactions with amine nucleophiles of formula 2 such as anilines, in the presence of base as a proton scavenger, at temperatures from room temperature to 200° C., to give aminonitropyridines of formula II. During the initial $S_NAr$ reaction step the $R^1$ substituent on the amine nucleophiles of formula 2 should be represented by the same moiety as is desired in the final product, or a protected variation thereof. For example, the final product of Example 1 (N-cyclopropyl-3-(3-fluoro-4-methylphenyl)-3H-imidazo[4,5-b]pyridine-2-carboxamide) can be prepared utilizing reaction scheme 1, wherein $R^1$ of the amine nucleophile of formula 2 is represented by 3-fluoro-4-methylphenyl.

The next step of the reaction is the reduction of the nitro group of formula II to the amine to give the diaminopyridine compounds of formula III. This step can be effected through palladium or nickel reduction in the presence of a hydrogen source or through stoichiometric metal reductions, such as iron and zinc in the presence of mild acid.

In the next step, the half ester oxalamides of formula IV can be generated from amines of formula 3' (i.e., $HNR^6R^7$) displacement on a half ester of oxalyl chloride of formula 3. During the amine displacement step, the $R^6$ and $R^7$ substituents on the amines of formula 3' should be represented by the same moiety as is desired in the final product, or a protected variation thereof. For example, for the final product of Example 1 mentioned above, one of $R^6$ and $R^7$ of the amines of formula 3' is represented by hydrogen and the other is represented by cyclopropyl.

Following the amine displacement step, the compounds of formula V can be prepared by condensation of the diaminopyridines of formula III and the compounds of formula IV under thermal conditions, with reaction rates being increased under basic conditions.

In the final step of scheme 1, conversion of the compounds of formula V to the compounds of formula I can be accomplished under dehydrating conditions such as heat, treatment with a Lewis acid, or amide coupling conditions.

Scheme 1

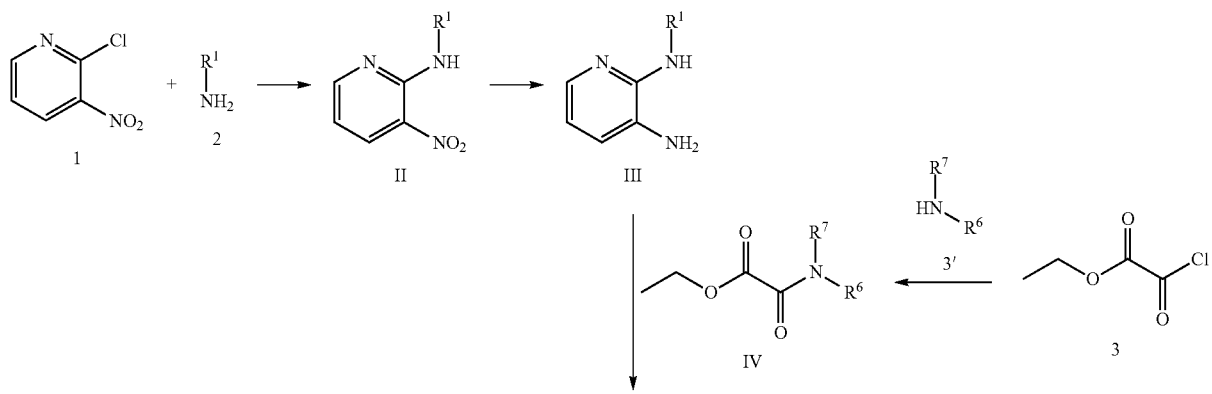

-continued

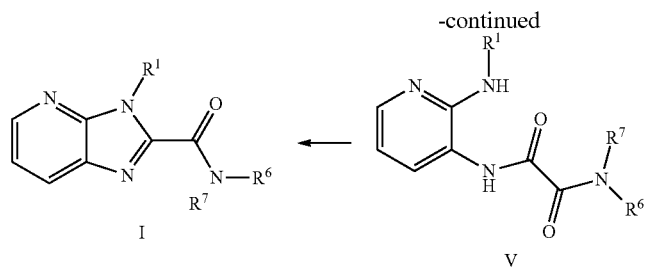

Scheme 2 below describes an alternative synthetic sequence for the preparation of compounds of formula I. Oxalic acids of formula VI can be generated in two steps from the treatment of half esters of oxalyl chloride of formula 3 with an amine of formula 3' in the presence of base, usually at room temperature or below. The resultant half ester oxalamides of formula IV can be hydrolyzed to the oxalic acids of formula VI by treatment under acidic or basic aqueous conditions at temperatures from 0° C. to 150° C.

Next, the diaminopyridines of formula III can be mixed with the oxalic acids of formula VI in the presence of amide coupling/dehydrating reagents, such as 2,4,6-tripropyl-1,3,5, 2,4,6-trioxatriphosphinane 2,4,6-trioxide (T3P), O-(7-azabenzotriazol-1-yl)-N,N,N',N' tetramethyluronium hexafluorophosphate (HATU), dicyclohexylcarbodiimide (DCC), etc., at temperatures ranging from −20° C. to 100° C.; subsequent heating up to 200° C. generates compounds of formula I.

oxalate of formula 4 (wherein x is represented by chloride, alkoxy, succinimide, etc.) to generate the aminopyridine aminooxoacetate compounds of formula VII.

In the next step the compounds of formula VII can be cyclized under dehydrating conditions such as heat, treatment with a Lewis acid, or amide coupling conditions such as 2,4,6-tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), dicyclohexylcarbodiimide (DCC), etc., to generate the imidazopyridine esters of formula VIII.

Next, the conversion of imidazopyridine esters of formula VIII to amides of formula I may be carried out via addition of an amine of formula 3' to imidazopyridine esters of formula VIII at temperatures from 20° C. to 200° C. in the presence or absence of solvent. Additionally, this transformation can be

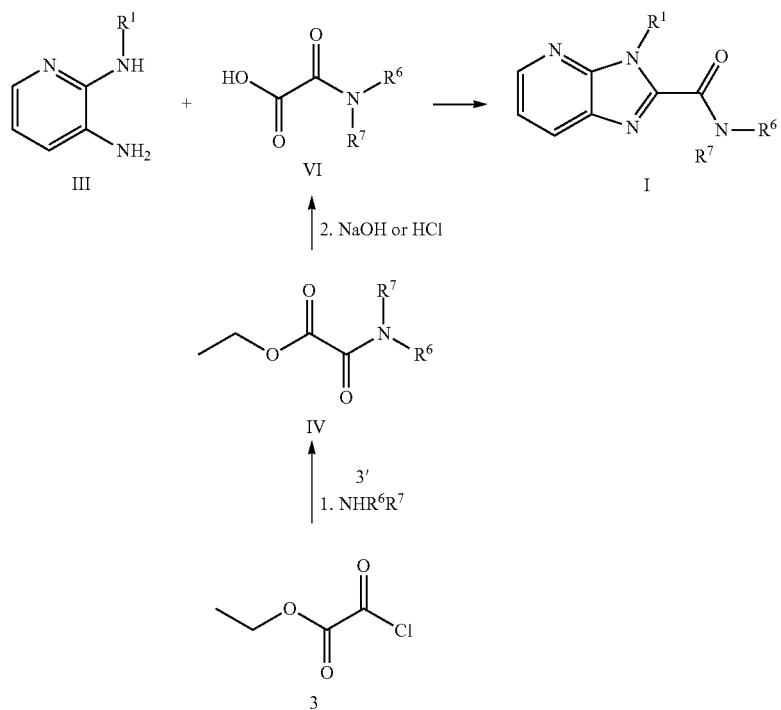

Scheme 3 below illustrates an alternative synthetic sequence for the preparation of compounds of formula I. Diaminopyridines of formula III can be acylated by the nucleophilic displacement of a leaving group on an ester-accomplished through the addition of a base or Lewis acid to the mixture of amine and imidazopyridine esters of formula VIII at temperatures ranging from 20° C. to 200° C. or under microwave irradiation at applicable temperatures.

Scheme 3

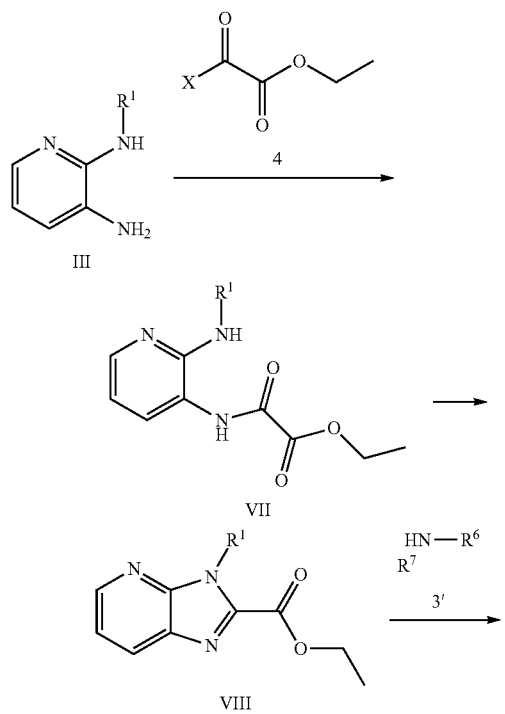

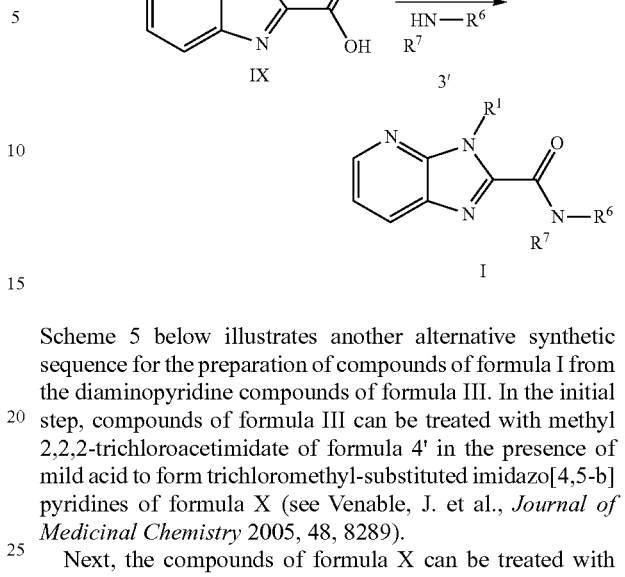

Scheme 4 below illustrates another alternative synthetic sequence for preparation of the compounds of formula I from the esters of formula VIII. In an initial step, esters of formula VIII can be hydrolyzed to the corresponding imidazopyridine carboxylic acids of formula IX under basic or acidic aqueous conditions. During the initial step, the $R^1$ substituent on the esters of formula VIII should be represented by the same moiety as is desired in the final product, or a protected variation thereof.

Next, the imidazopyridine acids of formula IX can be reacted with an appropriate amine of formula 3' using any of a variety of amide coupling reagents such as 2,4,6-tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), dicyclohexylcarbodiimide (DCC), etc., to provide the compounds of formula I.

Scheme 4

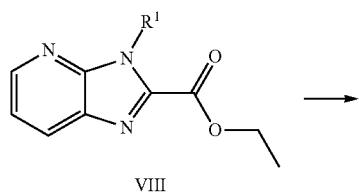

Scheme 5 below illustrates another alternative synthetic sequence for the preparation of compounds of formula I from the diaminopyridine compounds of formula III. In the initial step, compounds of formula III can be treated with methyl 2,2,2-trichloroacetimidate of formula 4' in the presence of mild acid to form trichloromethyl-substituted imidazo[4,5-b] pyridines of formula X (see Venable, J. et al., *Journal of Medicinal Chemistry* 2005, 48, 8289).

Next, the compounds of formula X can be treated with amines of formula 3' under mild basic aqueous conditions to provide compounds of formula I.

Scheme 5

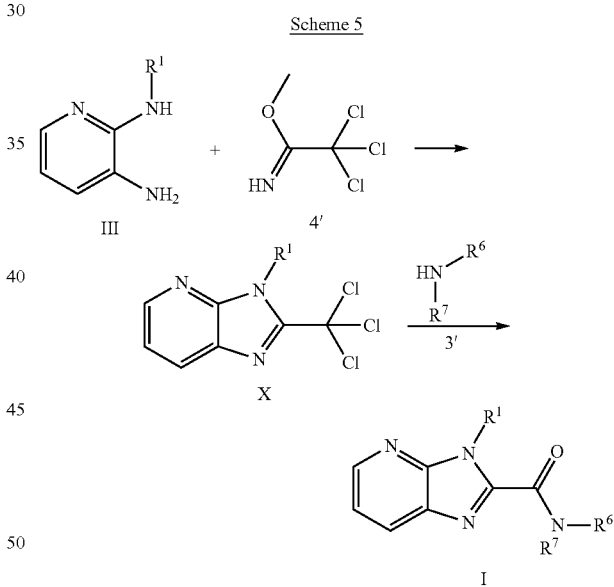

Scheme 6 below illustrates another synthetic sequence for the prepratation of the compounds of formula I wherein $R^1$ is optionally substituted aryl.

In a first step, 2-amino-3-nitropyridine is coupled with a haloaryl compound of formula 5 in the presence of a metal catalyst (palladium, copper, rhodium, etc.), a ligand, and a base at temperatures ranging from room temperature to ~200° C., to generate anilinopyridine structures of formula XI. This general reaction is sometimes referred to as the Buchwald-Hartwig amination. Similar couplings have been described previously (WO2008/4117A1 and *Org. Lett.* 2009, 11, 5502-5505). During this reaction, the $R^1$ substituent on the haloaryl compound of formula 5 should be represented by the same moiety as is desired in the final product, or a protected variation thereof. For example, the final product of Example 7 [3-(4-cyano-3-fluorophenyl)-N-cyclopropyl-3H-imidazo[4,5-b]pyridine-2-carboxamide] can be prepared utilizing reaction scheme 6, wherein $R^1$ of the diaminopyridine is represented by 4-cyano-3-fluorophenyl.

In the next step, reduction of the nitro group to an amine to give the compounds of formula XII can occur through palladium or nickel reduction in the presence of a hydrogen source, or through stoichiometric metal reductions, such as iron and zinc in the presence of mild acid.

Next, compounds of formula XII can be converted to compounds of formula I through reaction of compounds of formula XII and a compound of formula IV (Scheme 2) under basic conditions, at temperatures ranging from room temperature to 200° C. followed by the room temperature addition of a dehydrating reagent/amide coupling reagent 2,4,6-tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), dicyclohexylcarbodiimide (DCC), etc., and subsequent reaction via appropriate heating (room temperature to 200° C.) to generate compounds of formula I wherein $R^1$ is optionally substituted aryl, wherein the optional substituent is represented by $(R^2)_b$.

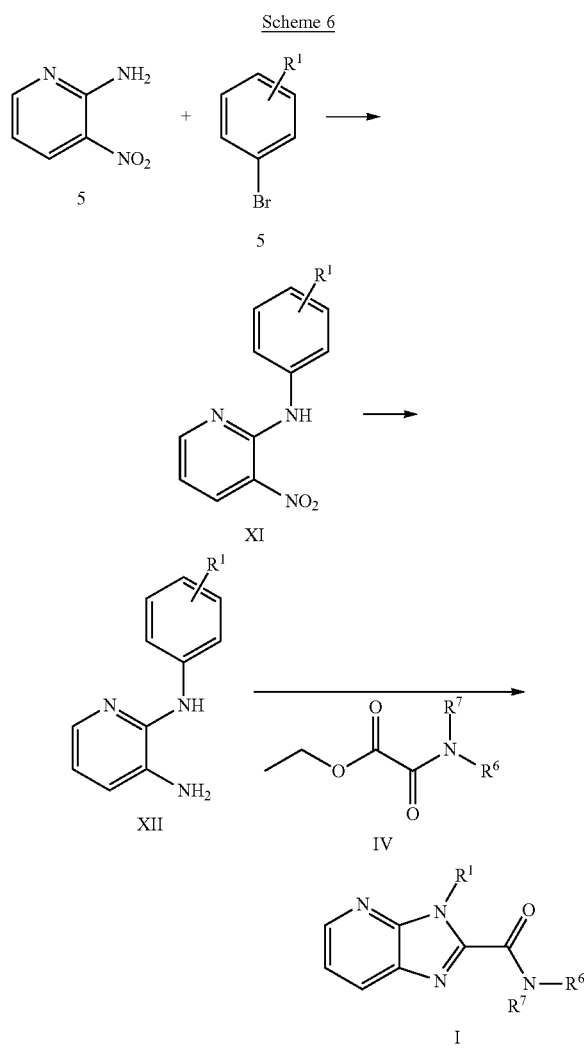

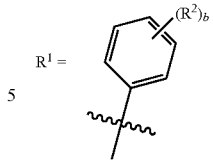

Experimental Procedures and Working Examples

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate (generally Sure-Seal™ products from the Aldrich Chemical Company, Milwaukee, Wis., or solvents that had been dried and distilled using procedures familiar to those skilled in the art). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

Preparation P1

Ethyl(cyclopropylamino)(oxo)acetate (P1)

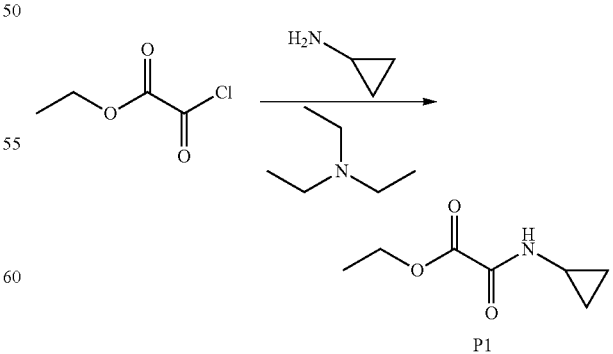

A mixture of cyclopropylamine (1.39 g, 24.3 mmol) and triethylamine (3.5 g, 35 mmol) was added drop-wise to a 0° C. solution of ethyl chloro(oxo)acetate (3.5 g, 26 mmol) in tetrahydrofuran (25 mL). The reaction mixture was stirred at 0° C. for 10 minutes and filtered; the filtrate was concentrated in vacuo to afford the product as a yellow solid Yield: 3.0 g, 19 mmol, 78%. $^1$H NMR (400 MHz, CDCl$_3$) δ 7.14 (br s, 1H), 4.34 (q, J=7.2 Hz, 2H), 2.78-2.86 (m, 1H), 1.38 (t, J=7.2 Hz, 3H), 0.83-0.90 (m, 2H), 0.59-0.65 (m, 2H).

Preparation P2

(Cyclopropylamino)(oxo)acetic acid (P2)

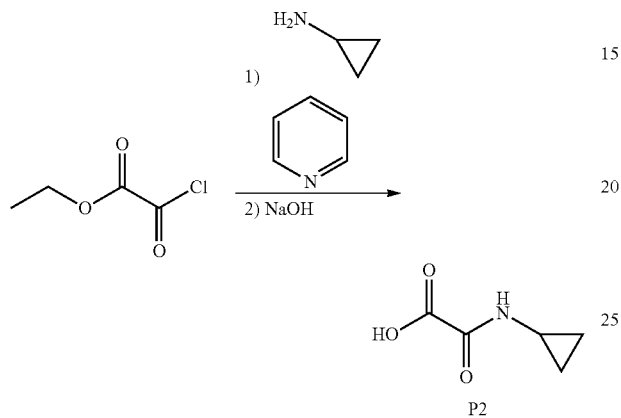

Ethyl chloro(oxo)acetate (96 mL, 0.86 mol) was added over 10 minutes to a −20° C. solution of cyclopropylamine (60 mL, 0.86 mol) and pyridine (70 mL, 0.86 mol) in dichloromethane (740 mL), and the reaction mixture was stirred at 0° C. for 1 hour, then at 20° C. for 20 hours. The reaction mixture was washed with aqueous hydrochloric acid (1 M, 3×185 mL), then the organic layer was stirred with aqueous sodium hydroxide solution (1 M, 930 mL, 0.93 mol) for 30 minutes. The resulting aqueous layer was acidified to pH 1 with concentrated hydrochloric acid (78 mL), treated with sodium chloride (100 g), and extracted with dichloromethane (6×500 mL) and ethyl acetate (6×500 mL). The combined organic layers were dried over magnesium sulfate, filtered, and concentrated in vacuo; the resulting solid was mixed with ethyl acetate (150 mL) and warmed to reflux. After cooling to room temperature over 16 hours with stirring, the solid was collected via filtration and washed with ethyl acetate, affording the product as a sparkling white solid. Yield: 67.8 g, 0.525 mol, 61%. LCMS m/z 130.0 [M+H]$^+$. $^1$H NMR (400 MHz, DMSO-d$_6$) δ 13.73 (br s, 1H), 8.83 (br d, J=4.0 Hz, 1H), 2.68-2.77 (m, 1H), 0.61-0.68 (m, 2H), 0.54-0.61 (m, 2H).

EXAMPLES

Example 1

N-Cyclopropyl-3-(3-fluoro-4-methylphenyl)-3H-imidazo[4,5-b]pyridine-2-carboxamide (1)

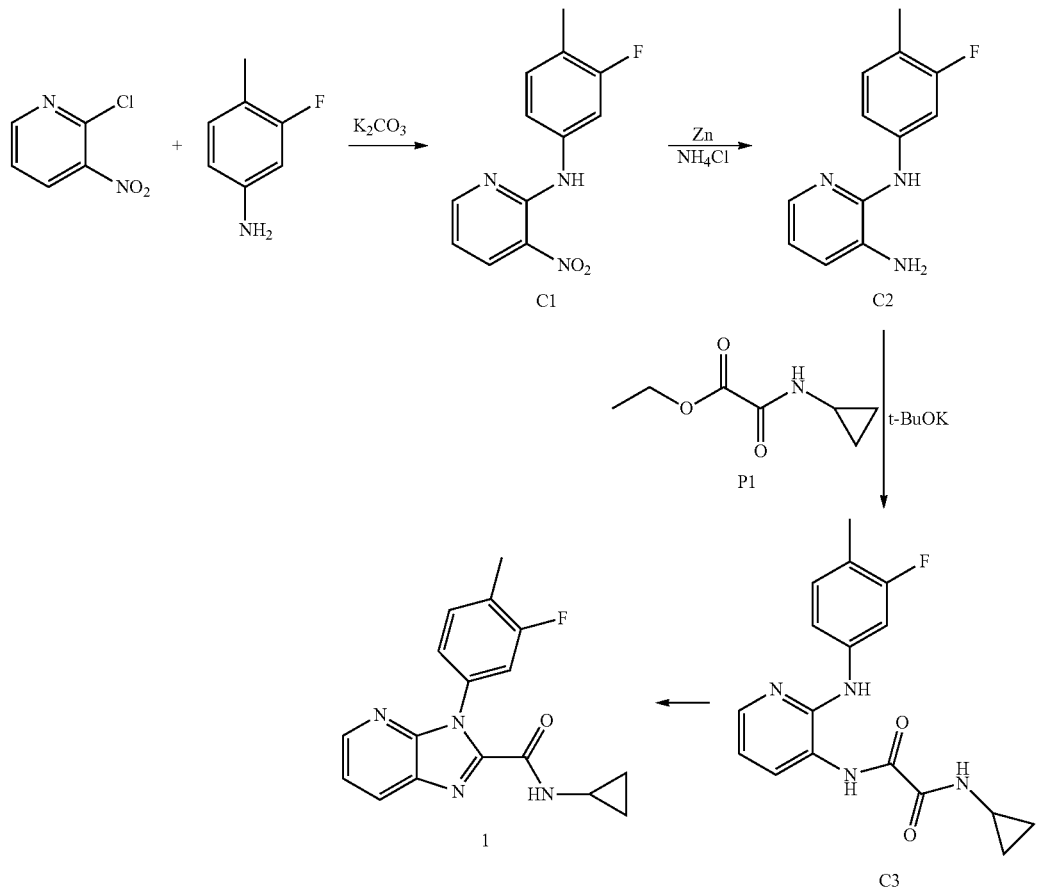

Step 1. Synthesis of N-(3-fluoro-4-methylphenyl)-3-nitropyridin-2-amine (C1)

A mixture of 2-chloro-3-nitropyridine (4.76 g, 30.0 mmol), 3-fluoro-4-methylaniline (3.75 g, 30.0 mmol) and potassium carbonate (8.29 g, 60.0 mmol) in dimethyl sulfoxide (30 mL) was stirred at 140° C. for 40 minutes. The reaction mixture was then cooled to room temperature, diluted with water, and extracted with ethyl acetate. The combined organic layers were washed with water, dried over magnesium sulfate, filtered, and concentrated in vacuo to afford the product as a black solid. Yield: 6.78 g, 27.4 mmol, 91%. $^1$H NMR (400 MHz, CDCl$_3$) δ 10.11 (br s, 1H), 8.54 (dd, J=8.3, 1.8 Hz, 1H), 8.51 (dd, J=4.6, 1.8 Hz, 1H), 7.59-7.64 (m, 1H), 7.15-7.21 (m, 2H), 6.86 (dd, J=8.4, 4.6 Hz, 1H), 2.28 (d, J=2.0 Hz, 3H).

Step 2. Synthesis of $N^2$-(3-fluoro-4-methylphenyl)pyridine-2,3-diamine (C2)

Zinc dust (14.3 g, 219 mmol) was added to a stirring mixture of N-(3-fluoro-4-methylphenyl)-3-nitropyridin-2-amine (C1) (6.78 g, 27.4 mmol) and ammonium chloride (11.7 g, 219 mmol) in tetrahydrofuran (55 mL) and water (55 mL), which caused the temperature of the mixture to rise to 45° C. The reaction mixture was stirred for 10 minutes, and then filtered through a pad of Celite, rinsing with ethyl acetate. The organic layer from the filtrate was further diluted with ethyl acetate, washed with aqueous ammonium chloride solution and with saturated aqueous sodium chloride solution, dried over magnesium sulfate, and filtered. The filtrate was concentrated in vacuo to afford the product as a black solid (6.6 g), the bulk of which was taken directly to the following step. LCMS m/z 218.1 [M+H]$^+$. $^1$H NMR (400 MHz, CDCl$_3$), characteristic product peaks: δ 7.84 (dd, J=4.9, 1.6 Hz, 1H), 7.01 (dd, J=7.6, 1.6 Hz, 1H), 6.82 (br dd, J=8, 2 Hz, 1H), 6.77 (dd, J=7.6, 4.9 Hz, 1H), 2.20 (d, J=2 Hz, 3H).

Step 3. Synthesis of N-cyclopropyl-N'-{2-[(3-fluoro-4-methylphenyl)amino]pyridin-3-yl}ethanediamide (C3)

Potassium tert-butoxide (4.54 g, 40.5 mmol) was added to a solution of $N^2$-(3-fluoro-4-methylphenyl)pyridine-2,3-diamine (C2) (from the previous step, 5.87 g, 24.4 mmol) and ethyl(cyclopropylamino)(oxo)acetate (P1) (6.36 g, 40.5 mmol) in 1-methylpyrrolidin-2-one (27 mL). The reaction mixture was heated at 120° C. for 10 minutes, cooled to room temperature and diluted with aqueous ammonium chloride solution. Tetrahydrofuran was added to assist solubilization, followed by ethyl acetate. The organic layer was washed with saturated aqueous sodium chloride solution, dried over magnesium sulfate, filtered, and concentrated in vacuo to provide the crude product (13.0 g). A portion of this material was used directly in the following step. LCMS m/z 329.0 [M+H]$^+$.

Step 4. Synthesis of N-cyclopropyl-3-(3-fluoro-4-methylphenyl)-3H-imidazo[4,5-b]pyridine-2-carboxamide (1)

A mixture of N-cyclopropyl-N'-{2-[(3-fluoro-4-methylphenyl)amino]pyridin-3-yl}ethanediamide (C3) (from the preceding step, 8.86 g, ≤16.6 mmol) and ethane-1,2-diol (27 mL) was stirred at 200° C. for 1 hour. After cooling to room temperature, the reaction mixture was diluted with water (100 mL) and aqueous sodium hydroxide solution (1 M, 100 mL), then extracted with ethyl acetate. The combined organic layers were washed with saturated aqueous sodium chloride solution, dried over magnesium sulfate, filtered, and concentrated under reduced pressure. Purification using silica gel chromatography (Gradient: 5% to 50% ethyl acetate in heptane) was followed by recrystallization from 3:1 toluene/heptane, to afford the product as a solid. Yield: 2.52 g, 8.12 mmol, 49% over three steps. LCMS m/z 311.0 [M+H]$^+$. $^1$H NMR (400 MHz, CDCl$_3$) δ 8.50 (dd, J=4.7, 1.5 Hz, 1H), 8.13 (dd, J=8.1, 1.5 Hz, 1H), 7.68 (br s, 1H), 7.37 (dd, J=8.1, 4.7 Hz, 1H), 7.34-7.40 (m, 1H), 7.10-7.15 (m, 2H), 2.83-2.90 (m, 1H), 2.37 (br d, J=2 Hz, 3H), 0.83-0.89 (m, 2H), 0.67-0.72 (m, 2H).

Example 2

3-Cyclopentyl-N-cyclopropyl-3H-imidazo[4,5-b]pyridine-2-carboxamide (2)

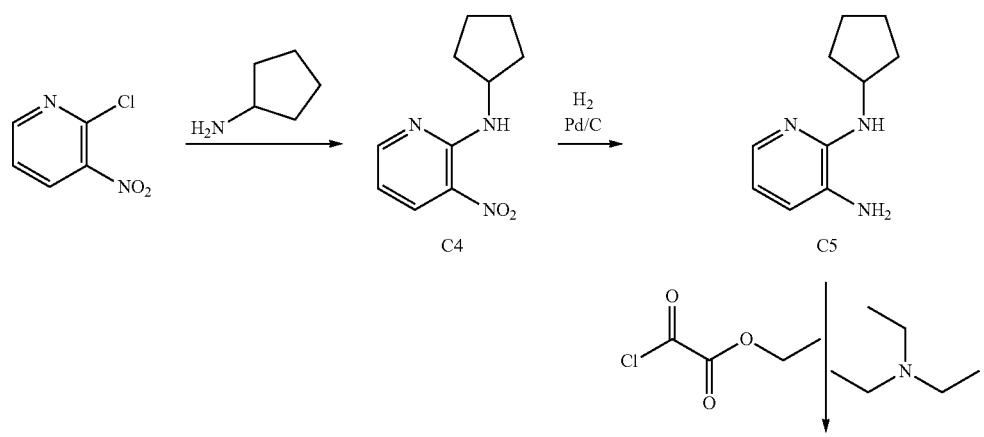

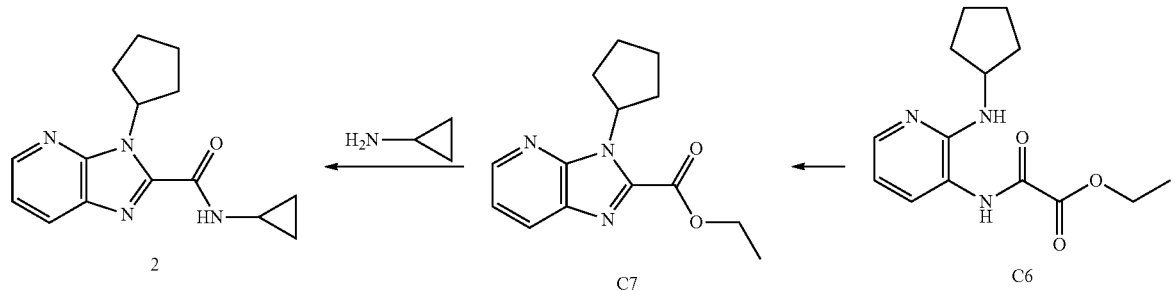

Step 1. Synthesis of N-cyclopentyl-3-nitropyridin-2-amine (C4)

Cyclopentanamine (2.7 g, 32 mmol) was added to a solution of 2-chloro-3-nitropyridine (5.0 g, 32 mmol) in tetrahydrofuran (200 mL), and the reaction mixture was stirred at reflux for 18 hours. After removal of solvent under reduced pressure, the residue was purified via silica gel chromatography to give the product as a yellow solid. Yield: 5.5 g, 26 mmol, 81%. $^1$H NMR (400 MHz, CD$_3$OD) δ 8.42 (dd, half of ABX pattern, J=8.3, 1.8 Hz, 1H), 8.40 (dd, half of ABX pattern, J=4.5, 1.8 Hz, 1H), 6.69 (dd, J=8.3, 4.5 Hz, 1H), 4.51-4.59 (m, 1H), 2.07-2.17 (m, 2H), 1.62-1.85 (m, 4H), 1.51-1.62 (m, 2H)

Step 2. Synthesis of N$^2$-cyclopentylpyridine-2,3-diamine (C5)

To a solution of N-cyclopentyl-3-nitropyridin-2-amine (C4) (4.7 g, 23 mmol) in methanol (100 mL) was added palladium on carbon (0.5 g), and the mixture was degassed with hydrogen. After stirring under hydrogen at room temperature for 4 hours, the reaction mixture was filtered; the filtrate was concentrated in vacuo to afford the product as a black solid. Yield: 3.6 g, 20 mmol, 87%. $^1$H NMR (400 MHz, DMSO-d$_6$) δ 7.35 (dd, J=5, 1 Hz, 1H), 6.63 (dd, J=7.3, 1.0 Hz, 1H), 6.30 (dd, J=7.3, 5.0 Hz, 1H), 5.31 (br d, J=6.3 Hz, 1H), 4.69 (br s, 2H), 4.18-4.28 (m, 1H), 1.88-2.00 (m, 2H), 1.61-1.75 (m, 2H), 1.36-1.60 (m, 4H).

Step 3. Synthesis of ethyl{[2-(cyclopentylamino)pyridin-3-yl]amino}(oxo)acetate (C6)

To a solution of N$^2$-cyclopentylpyridine-2,3-diamine (C5) (1.78 g, 10.0 mmol) and triethylamine (1.52 g, 15.0 mmol) in dichloromethane (100 mL) was added ethyl chloro(oxo)acetate (1.49 g, 10.9 mmol), and the reaction mixture was stirred at room temperature for 18 hours. Removal of volatiles in vacuo afforded the crude product (2 g) as a brown solid, which was used in the next step without further purification.

Step 4. Synthesis of ethyl 3-cyclopentyl-3H-imidazo[4,5-b]pyridine-2-carboxylate (C7)

A solution of crude ethyl {[2-(cyclopentylamino)pyridin-3-yl]amino}(oxo)acetate (C6) (from the previous step, 2 g) in toluene (100 mL) was stirred at reflux for 18 hours. The reaction mixture was concentrated in vacuo and the residue was purified using silica gel chromatography (Gradient: 9% to 50% ethyl acetate in petroleum ether) to provide the product as a brown solid. Yield: 0.70 g, 2.7 mmol, 27% over 2 steps. $^1$H NMR (400 MHz, CD$_3$OD) δ 8.53 (dd, J=4.6, 1.4 Hz, 1H), 8.14 (dd, J=8.2, 1.4 Hz, 1H), 7.40 (dd, J=8.2, 4.7 Hz, 1H), 5.79-5.89 (m, 1H), 4.51 (q, J=7.1 Hz, 2H), 2.48-2.61 (m, 2H), 2.07-2.20 (m, 4H), 1.70-1.83 (m, 2H), 1.46 (t, J=7.2 Hz, 3H).

Step 5. Synthesis of 3-cyclopentyl-N-cyclopropyl-3H-imidazo[4,5-b]pyridine-2-carboxamide (2)

To a solution of ethyl 3-cyclopentyl-3H-imidazo[4,5-b]pyridine-2-carboxylate (C7) (0.12 g, 0.46 mmol) in ethanol (10 mL) was added cyclopropylamine (0.55 g, 9.6 mmol), and the reaction mixture was stirred at room temperature for 18 hours. After concentration in vacuo, purification was effected via preparative thin layer chromatography on silica gel (Eluent: 5:1 petroleum ether/ethyl acetate) to afford the product as a yellow solid. Yield: 36 mg, 0.13 mmol, 28%. LCMS m/z 270.9 [M+H]$^+$. $^1$H NMR (400 MHz, CDCl$_3$) δ 8.47 (dd, J=4.6, 1.5 Hz, 1H), 8.02 (br d, J=8 Hz, 1H), 7.85 (br s, 1H), 7.27 (dd, J=8.2, 4.6 Hz, 1H, assumed; partially obscured by solvent peak), 6.16-6.27 (m, 1H), 2.89-2.97 (m, 1H), 2.51-2.64 (m, 2H), 2.06-2.19 (m, 4H), 1.69-1.81 (m, 2H), 0.87-0.95 (m, 2H), 0.69-0.76 (m, 2H).

Example 3

3-(4-Chlorophenyl)-N-cyclopropyl-3H-imidazo[4,5-b]pyridine-2-carboxamide (3)

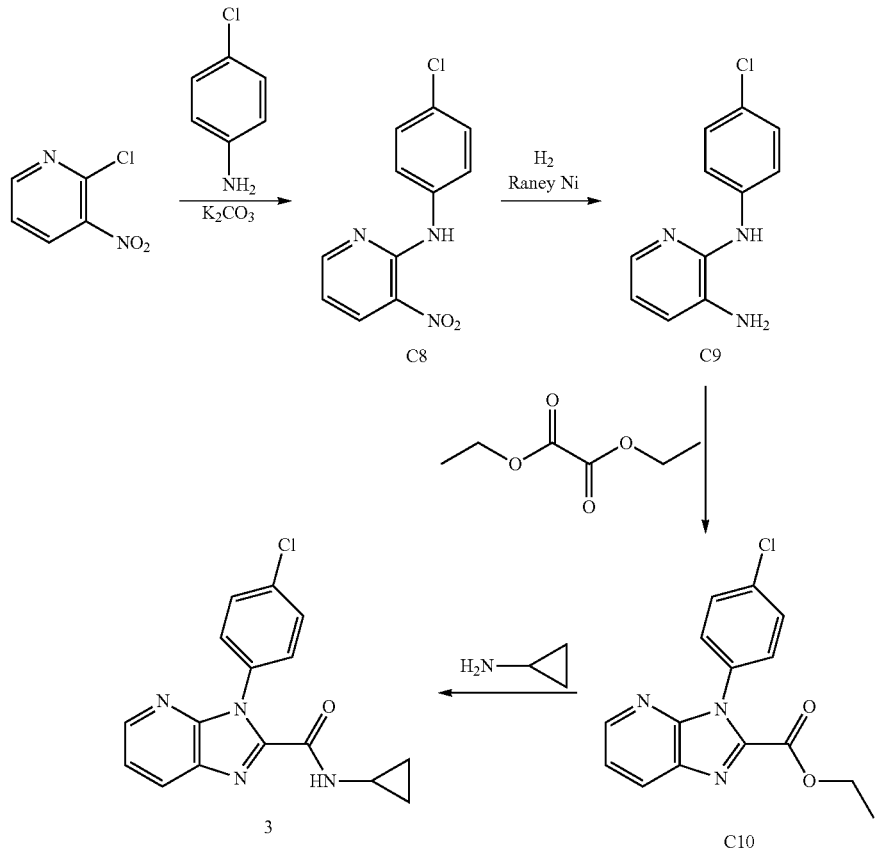

Step 1. Synthesis of N-(4-chlorophenyl)-3-nitropyridin-2-amine (C8)

To a solution of 2-chloro-3-nitropyridine (15.4 g, 97.1 mmol) in N,N-dimethylformamide (100 mL) were added 4-chloroaniline (12.4 g, 97.2 mmol) and potassium carbonate (20 g, 140 mmol). The reaction mixture was stirred at 100° C. for 18 hours, and then poured into ice-water (200 mL). The precipitate was collected via filtration and washed with water (3×30 mL) to provide the product as a black solid. Yield: 15 g, 60 mmol, 62%. $^1$H NMR (400 MHz, DMSO-$d_6$) δ 9.97 (br s, 1H), 8.47-8.57 (m, 2H), 7.69 (d, J=8.8 Hz, 2H), 7.41 (d, J=8.8 Hz, 2H), 7.01 (dd, J=8.2, 4.6 Hz, 1H).

Step 2. Synthesis of N²-(4-chlorophenyl)pyridine-2,3-diamine (C9)

To a solution of N-(4-chlorophenyl)-3-nitropyridin-2-amine (C8) (2.68 g, 10.7 mmol) in ethyl acetate (100 mL) was added Raney nickel (1.5 g), and the mixture was degassed with hydrogen. After 6 hours of hydrogenation at room temperature, the reaction mixture was filtered; concentration of the filtrate in vacuo afforded the product as a black solid. Yield: 1.8 g, 8.2 mmol, 77%. $^1$H NMR (400 MHz, DMSO-$d_6$) δ 7.88 (br s, 1H), 7.67 (d, J=8.9 Hz, 2H), 7.50 (br d, J=4 Hz, 1H), 7.25 (d, J=8.9 Hz, 2H), 6.91 (br d, J=7.5 Hz, 1H), 6.64 (dd, J=7.3, 4.8 Hz, 1H), 5.08 (br s, 2H).

Step 3. Synthesis of ethyl 3-(4-chlorophenyl)-3H-imidazo[4,5-b]pyridine-2-carboxylate (C10)

A mixture of N²-(4-chlorophenyl)pyridine-2,3-diamine (C9) (1.8 g, 8.2 mmol) and diethyl ethanedioate (18 g, 123 mmol) was stirred at 140° C. for 18 hours. Purification using silica gel chromatography (Gradient: 16% to 50% ethyl acetate in petroleum ether) provided the product as a brown solid, containing approximately 30% of a contaminant by $^1$H NMR analysis. Yield: 250 mg, 0.83 mmol, 10%. $^1$H NMR (400 MHz, CD$_3$OD), product peaks only: δ 8.49 (dd, J=4.8, 1.5 Hz, 1H), 8.31 (dd, J=8.2, 1.4 Hz, 1H), 7.61 (br d, J=8.9 Hz, 2H), 7.52 (dd, J=8.2, 4.6 Hz, 1H), 7.49 (br d, J=8.9 Hz, 2H), 4.34 (q, J=7.2 Hz, 2H), 1.25 (t, J=7.2 Hz, 3H).

Step 4. Synthesis of 3-(4-chlorophenyl)-N-cyclopropyl-3H-imidazo[4,5-b]pyridine-2-carboxamide (3)

Ethyl 3-(4-chlorophenyl)-3H-imidazo[4,5-b]pyridine-2-carboxylate (C10) was converted to the product using the method described for synthesis of 2 in Example 2. The product was obtained as an off-white solid. Yield: 34.5 mg, 0.110 mmol, 28%. LCMS m/z 312.9 [M+H]⁺. $^1$H NMR (400 MHz, CD$_3$OD) δ 8.42 (dd, J=4.8, 1.5 Hz, 1H), 8.24 (dd, J=8.2, 1.4 Hz, 1H), 7.58 (br d, J=8.8 Hz, 2H), 7.43-7.49 (m, 3H), 2.76-2.83 (m, 1H), 0.77-0.84 (m, 2H), 0.63-0.69 (m, 2H).

Example 4

3-(4-Chloro-3-fluorophenyl)-N-cyclopropyl-3H-imidazo[4,5-b]pyridine-2-carboxamide (4)

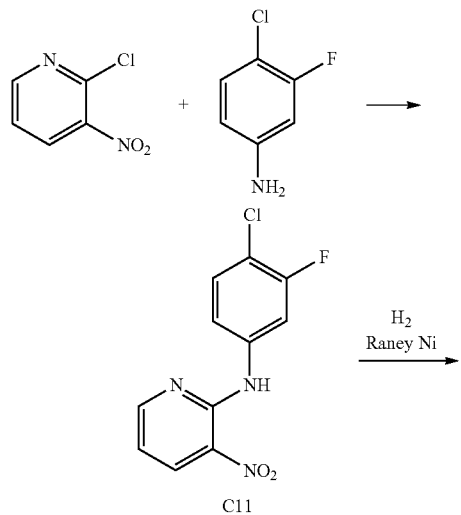

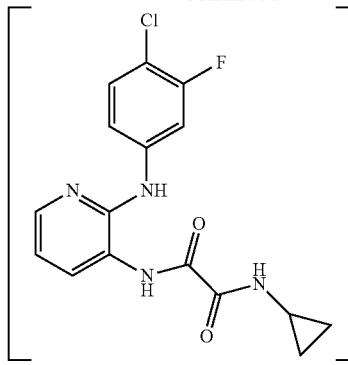

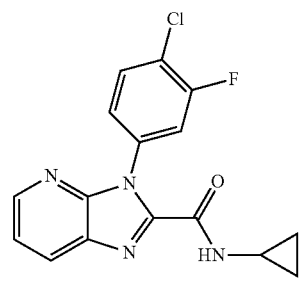

Step 1. Synthesis of N-(4-chloro-3-fluorophenyl)-3-nitropyridin-2-amine (C11)

4-Chloro-3-fluoroaniline (10.0 g, 68.7 mmol) was heated to 180° C. in an oil bath. 2-Chloro-3-nitropyridine (11.0 g, 69.4 mmol) was added, and the resulting mixture was stirred at 180° C. for 10 minutes. The reaction mixture was then cooled to 15° C. and washed with petroleum ether, providing the product as a salmon-pink solid. Yield: 15 g, 56 mmol, 82%. $^1$H NMR (400 MHz, CDCl$_3$) δ 10.20 (br s, 1H), 8.57 (dd, J=8.3, 1.6 Hz, 1H), 8.54 (dd, J=4.6, 1.7 Hz, 1H), 7.90 (dd, J=11.3, 2.4 Hz, 1H), 7.38 (dd, J=8.5, 8.3 Hz, 1H), 7.23-7.28 (m, 1H, assumed; partially obscured by solvent peak), 6.94 (dd, J=8.3, 4.5 Hz, 1H).

Step 2. Synthesis of N$^2$-(4-chloro-3-fluorophenyl)pyridine-2,3-diamine (C12)

A mixture of N-(4-chloro-3-fluorophenyl)-3-nitropyridin-2-amine (C11) (5.0 g, 19 mmol) and Raney nickel (3 g) in ethyl acetate (400 mL) was degassed three times with hydrogen. The reaction mixture was then hydrogenated at room temperature for 20 hours. After removal of the catalyst via filtration, the filtrate was concentrated in vacuo. Purification via silica gel chromatography afforded the product as a gray solid. Yield: 3.1 g, 13 mmol, 68%. $^1$H NMR (400 MHz, CDCl$_3$) δ 7.87 (dd, J=4.9, 1.6 Hz, 1H), 7.38 (dd, J=11.5, 2.5 Hz, 1H), 7.24 (dd, J=8.5, 8.4 Hz, 1H), 7.06 (dd, J=7.6, 1.6 Hz, 1H), 6.92 (ddd, J=8.7, 2.5, 1.0 Hz, 1H), 6.82 (dd, J=7.6, 4.9 Hz, 1H), 6.37 (br s, 1H), 3.38 (br s, 2H).

Step 3. Synthesis of 3-(4-chloro-3-fluorophenyl)-N-cyclopropyl-3H-imidazo[4,5-b]pyridine-2-carboxamide (4)

A mixture of the mono-tosylate salt of N²-(4-chloro-3-fluorophenyl)pyridine-2,3-diamine (C12) [prepared via treatment of C12 with p-toluenesulfonic acid monohydrate (1.5 equivalents) in ethanol at 80° C., followed by cooling to room temperature and isolation via filtration] (1.003 g, 2.447 mmol), (cyclopropylamino)(oxo)acetic acid (P2) (0.304 g, 2.35 mmol), 2,6-dimethylpyridine (0.91 mL, 0.84 g, 7.8 mmol), and 2-methyltetrahydrofuran (10 mL) was cooled to −10° C. and treated with 2,4,6-tripropyl-1,3,5,2,4,6-trioxatriphosphinane 2,4,6-trioxide (50 weight % solution in ethyl acetate, 4.3 mL, 4.6 g, 7.2 mmol). The reaction mixture was warmed to 0° C. and held for 1 hour, heated at reflux for 20 hours, and then cooled to 0° C. and filtered, rinsing with 2-methyltetrahydrofuran. The filtrate was sequentially washed with water (10 mL, 5 mL), with aqueous ammonium hydroxide solution (15%, 3×5 mL), with aqueous hydrochloric acid (0.1 M, 10 mL, 5 mL), and with water (10 mL). The organic layer was distilled to a volume of approximately 4 mL, diluted with 2-nnethyltetrahydrofuran (13 mL), and again distilled to approximately 4 mL, whereupon it was cooled to 50° C. and treated with heptane (3 mL). The resulting slurry was stirred at 50° C. for 2 hours, cooled to 20° C., and stirred for 12 hours. The solid was collected via filtration and washed with a mixture of heptane and 2-methyltetrahydrofuran (2:1, 5 mL). The resulting material (0.488 g) was reslurried in a mixture of 2-propanol and ethyl acetate (9:1, 4.9 mL), warmed to 40° C., cooled to 20° C., and stirred for 16 hours. Filtration and washing with 2-propanol (3 mL) afforded the product as an off-white solid. Yield: 410 mg, 1.24 mmol, 53%. LCMS m/z 330.9, 332.9 [M+H]⁺. ¹H NMR (400 MHz, DMSO-d₆) δ 9.17 (d, J=4.8 Hz, 1H), 8.45 (d, J=4.5 Hz, 1H), 8.27 (d, J=8.0 Hz, 1H), 7.71-7.80 (m, 2H), 7.47 (dd, J=8.0, 4.8 Hz, 1H), 7.40 (br d, J=8.5 Hz, 1H), 2.77-2.86 (m, 1H), 0.65-0.69 (m, 4H).

Example 5

3-(4-Chloro-3-fluorophenyl)-N-(1-methyl-1H-pyrazol-3-yl)-3H-imidazo[4,5-b]pyridine-2-carboxamide (5)

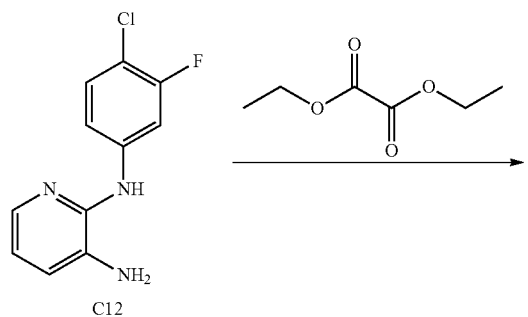

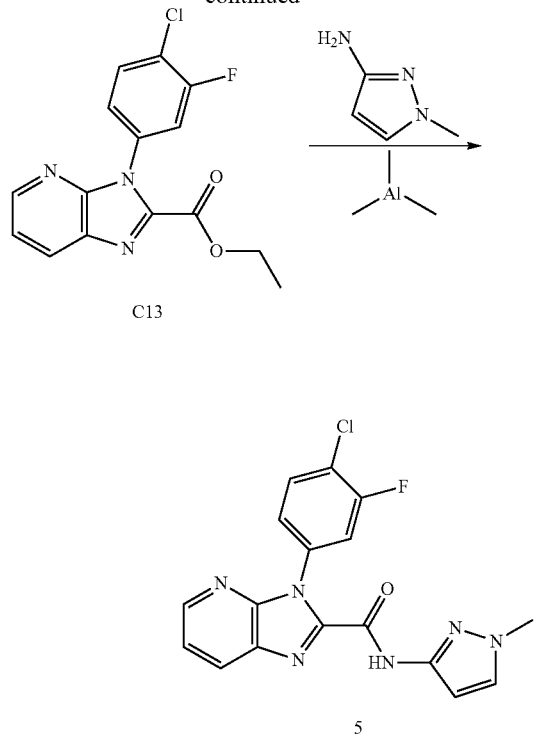

Step 1. Synthesis of ethyl 3-(4-chloro-3-fluorophenyl)-3H-imidazo[4,5-b]pyridine-2-carboxylate (C13)

Conversion of N²-(4-chloro-3-fluorophenyl)pyridine-2,3-diamine (C12) to the product was effected using the method described for synthesis of C10 in Example 3. The product was obtained as a brown solid. Yield: 700 mg, 2.2 mmol, 17%. ¹H NMR (400 MHz, CDCl₃) δ 8.55 (dd, J=4.6, 1.4 Hz, 1H), 8.29 (dd, J=8.2, 1.4 Hz, 1H), 7.61 (dd, J=8.3, 8.0 Hz, 1H), 7.42 (dd, J=8.2, 4.8 Hz, 1H), 7.29 (dd, J=8.9, 2.3 Hz, 1H, assumed; partially obscured by solvent peak), 7.18-7.22 (m, 1H), 4.44 (q, J=7.2 Hz, 2H), 1.41 (t, J=7.1 Hz, 3H).

Step 2. Synthesis of 3-(4-chloro-3-fluorophenyl)-N-(1-methyl-1H-pyrazol-3-yl)-3H-imidazo[4,5-b]pyridine-2-carboxamide (5)

To a solution of ethyl 3-(4-chloro-3-fluorophenyl)-3H-imidazo[4,5-b]pyridine-2-carboxylate (C13) (32 mg, 0.10 mmol) and 1-methyl-1H-pyrazol-3-amine (29 mg, 0.30 mol) in toluene (3 mL) was added trimethylaluminum (2 M solution in toluene, 0.3 mL, 0.6 mmol) at room temperature. The reaction mixture was irradiated in a microwave reactor at 150° C. for 1 hour, whereupon it was partitioned between water (20 mL) and ethyl acetate (50 mL). The organic layer was washed with saturated aqueous sodium chloride solution (20 mL), dried over sodium sulfate, filtered, and concentrated in vacuo. Purification via reversed phase HPLC (Column: Agella Venusil ASB-C18, 5 μm; Mobile phase A: 0.225% formic acid in water; Mobile phase B: 0.225% formic acid in acetonitrile; Gradient: 33% to 63% B) afforded the product as a yellow solid. Yield: 2.0 mg, 5.4 μmol, 5%. LCMS m/z 371.1 [M+H]⁺. ¹H NMR (400 MHz, CD₃OD) δ 8.47 (br d, J=4.6

Hz, 1H), 8.32 (br d, J=8 Hz, 1H), 7.69 (dd, J=8, 8 Hz, 1H), 7.48-7.56 (m, 3H), 7.35 (br d, J=8 Hz, 1H), 6.52-6.55 (m, 1H), 3.83 (s, 3H).

Example 6

3-(4-Chloro-3-fluorophenyl)-N-propyl-3H-imidazo[4,5-b]pyridine-2-carboxamide (6)

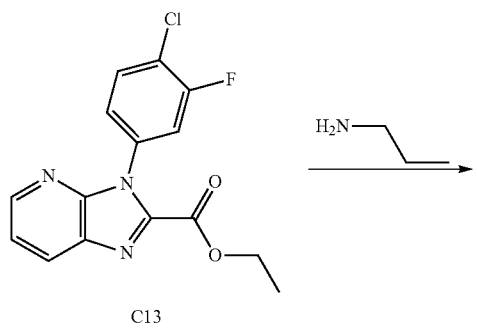

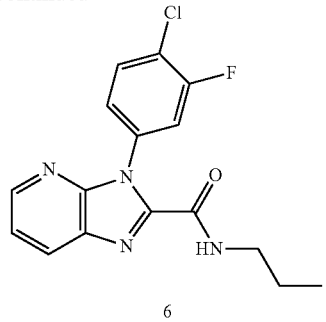

n-Propylamine (148 mg, 2.5 mol) was added to a solution of ethyl 3-(4-chloro-3-fluorophenyl)-3H-imidazo[4,5-b]pyridine-2-carboxylate (C13) (80 mg, 0.25 mmol) in ethanol (5 mL) and the reaction mixture was stirred at room temperature for 18 hours. After concentration under reduced pressure, the residue was purified by preparative thin layer chromatography on silica gel (Eluent: 1:1 petroleum ether/ethyl acetate) to provide the product as a pale yellow solid. Yield: 28 mg, 84 μmol, 34%. LCMS m/z 332.9 [M+H]$^+$. $^1$H NMR (400 MHz, CD$_3$OD) δ 8.43 (dd, J=4.8, 1.4 Hz, 1H), 8.26 (dd, J=8.2, 1.5 Hz, 1H), 7.67 (dd, J=8.4, 8.2 Hz, 1H), 7.45-7.50 (m, 2H), 7.30 (ddd, J=8.5, 2.3, 1.2 Hz, 1H), 3.28-3.34 (m, 2H, assumed; partially obscured by solvent peak), 1.58-1.68 (m, 2H), 0.96 (t, J=7.4 Hz, 3H).

Example 7

3-(4-Cyano-3-fluorophenyl)-N-cyclopropyl-3H-imidazo[4,5-b]pyridine-2-carboxamide (7)

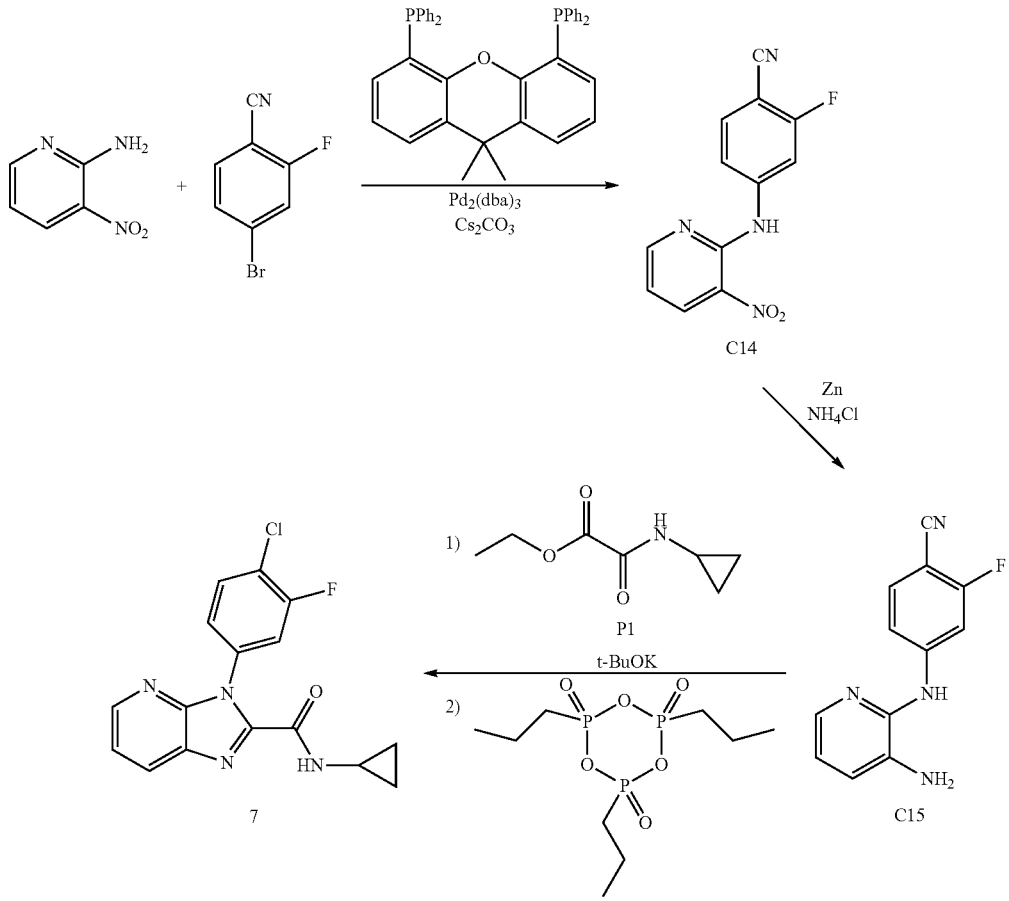

Step 1. Synthesis of 2-fluoro-4-[(3-nitropyridin-2-yl)amino]benzonitrile (C14)

A mixture of 3-nitropyridin-2-amine (3.44 g, 24.7 mmol), 4-bromo-2-fluorobenzonitrile (4.95 g, 24.7 mmol), tris(dibenzylideneacetone)dipalladium(0) (226 mg, 0.247 mmol), 4,5-bis(diphenylphosphino)-9,9-dimethylxanthene (XantPhos, 286 mg, 0.494 mmol) and cesium carbonate (32.3 g, 99.0 mmol) in 1,4-dioxane (124 mL) was degassed, placed under nitrogen and stirred at 100° C. for 30 minutes. The reaction mixture was filtered through a pad of Celite using tetrahydrofuran, and the filtrate was concentrated in vacuo. A 1:1 mixture of heptane and ethyl acetate was added to the residue, and the mixture was cooled in an ice/water bath. The solid was collected via filtration and washed with cold 1:1 heptane/ethyl acetate to afford the product as a gray solid. Yield: 6.2 g, 24 mmol, 97%. LCMS m/z 259.1 [M+H]$^+$. $^1$H NMR (400 MHz, CDCl$_3$) δ 10.46 (br s, 1H), 8.60-8.63 (m, 2H), 8.16 (dd, J=11.8, 2.1 Hz, 1H), 7.59 (dd, J=8.5, 7.2 Hz, 1H), 7.40 (br dd, J=8.6, 2 Hz, 1H), 7.05-7.09 (m, 1H).

Step 2. Synthesis of 4-[(3-aminopyridin-2-yl)-amino]-2-fluorobenzonitrile (C15)

To a solution of 2-fluoro-4-[(3-nitropyridin-2-yl)amino]benzonitrile (C14) (5.4 g, 21 mmol) in a 1:1 mixture of tetrahydrofuran and water (40 mL) was added ammonium chloride (8.9 g, 170 mmol), followed by zinc (10.8 g, 165 mmol). The mixture was stirred at 60° C. for 30 minutes, whereupon it was filtered through a pad of Celite. The organic layer from the filtrate was diluted with ethyl acetate, washed with saturated aqueous ammonium chloride solution, dried over sodium sulfate, filtered, and concentrated in vacuo; the residue was washed with heptane to afford the product as a brown solid. Yield: 4.2 g, 18 mmol, 86%. LCMS m/z 229.1 [M+H]$^+$. $^1$H NMR (400 MHz, DMSO-d$_6$) δ 8.68 (br s, 1H), 7.82 (dd, J=13.6, 2.0 Hz, 1H), 7.66 (dd, J=8.4, 8.3 Hz, 1H), 7.61 (dd, J=4.8, 1.6 Hz, 1H), 7.37 (dd, J=8.8, 2.0 Hz, 1H), 7.03 (dd, J=7.8, 1.6 Hz, 1H), 6.82 (dd, J=7.8, 4.8 Hz, 1H), 5.24 (br s, 2H).

Step 3. Synthesis of 3-(4-cyano-3-fluorophenyl)-N-cyclopropyl-3H-imidazo[4,5-b]pyridine-2-carboxamide (7)

To a mixture of 4-[(3-aminopyridin-2-yl)amino]-2-fluorobenzonitrile (C15) (3.9 g, 17 mmol) and ethyl(cyclopropylamino)(oxo)acetate (P1) (4.03 g, 25.6 mmol) in 1-methylpyrrolidin-2-one (17 mL) was added potassium tert-butoxide (2.88 g, 25.7 mmol). The reaction mixture was stirred at 120° C. for 30 minutes, cooled to room temperature, and treated with 2,4,6-tripropyl-1,3,5,2,4,6-trioxatriphosphinane 2,4,6-trioxide (T3P) (~50% weight solution, 20.3 mL, 32 mmol). After the reaction mixture had been stirred at 120° C. for 18 hours, it was allowed to cool. Water (10 mL) was added and stirring was continued for 10 minutes. Saturated aqueous sodium bicarbonate solution (20 mL) was introduced, and the mixture was extracted with ethyl acetate (3×50 mL). The combined organic layers were washed with saturated aqueous sodium chloride solution, filtered, and concentrated in vacuo Silica gel chromatography (Gradient: 10% to 50% ethyl acetate in petroleum ether) afforded the product as a white solid. Yield: 2.29 g, 7.13 mmol, 42%. LCMS m/z 322.2 [M+H]$^+$. $^1$H NMR (400 MHz, CDCl$_3$) δ 8.50 (dd, J=4.7, 1.4 Hz, 1H), 8.17 (dd, J=8.2, 1.5 Hz, 1H), 7.79-7.85 (m, 1H), 7.69 (br s, 1H), 7.38-7.45 (m, 3H), 2.83-2.90 (m, 1H), 0.87-0.93 (m, 2H), 0.68-0.73 (m, 2H).

Example 8

4-[2-(Azetidin-1-ylcarbonyl)-3H-imidazo[4,5-b]pyridin-3-yl]-2-fluorobenzonitrile (8)

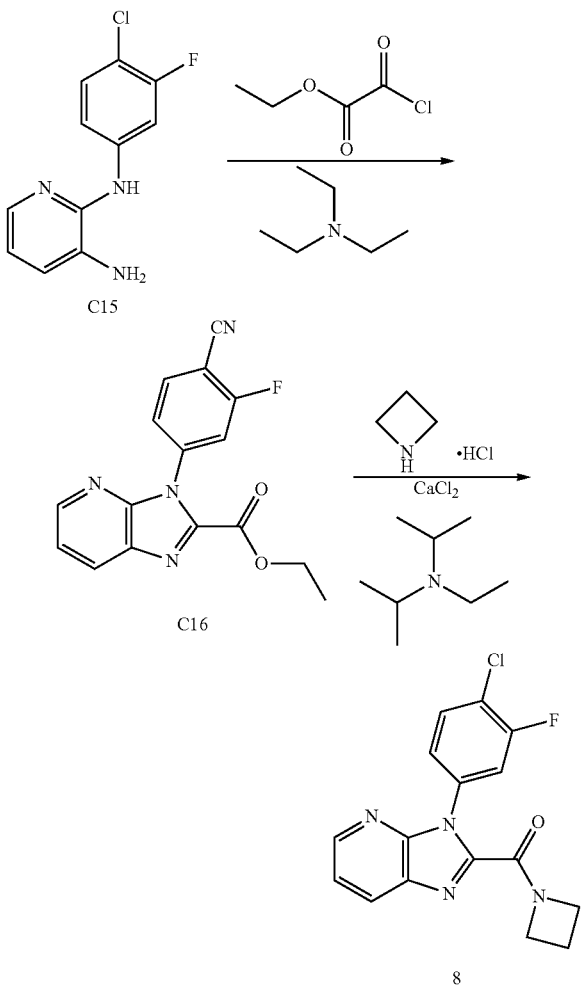

Step 1. Synthesis of ethyl 3-(4-cyano-3-fluorophenyl)-3H-imidazo[4,5-b]pyridine-2-carboxylate (C16)

To a 0° C. solution of 4-[(3-aminopyridin-2-yl)amino]-2-fluorobenzonitrile (C15) (300 mg, 1.31 mmol) and triethylamine (270 mg, 2.67 mmol) in dichloromethane (20 mL) was added ethyl chloro(oxo)acetate (220 mg, 1.61 mmol), and the solution was stirred at 0° C. for 2 hours. After addition of water (20 mL), the mixture was extracted with dichloromethane (3×20 mL); the combined organic layers were washed with saturated aqueous sodium chloride solution (20 mL), dried over sodium sulfate, filtered, concentrated under reduced pressure and purified by preparative thin layer chromatography on silica gel (Eluent: 10:1 dichloromethane/methanol) to afford the product as a yellow solid. Yield: 40 mg, 0.13 mmol, 10%. $^1$H NMR (400 MHz, CDCl$_3$), characteristic peaks: δ 8.55 (d, J=5 Hz, 1H), 4.46 (q, J=7 Hz, 2H), 1.43 (t, J=7 Hz, 3H).

Step 2. Synthesis of 4-[2-(azetidin-1-ylcarbonyl)-3H-imidazo[4,5-b]pyridin-3-yl]-2-fluorobenzonitrile (8)

A mixture of azetidine hydrochloride (120 mg, 1.3 mmol) and N,N-diisopropylethylamine (168 mg, 1.30 mmol) in methanol (2 mL) was stirred at room temperature for 1 hour. At this point, ethyl 3-(4-cyano-3-fluorophenyl)-3H-imidazo[4,5-b]pyridine-2-carboxylate (C16) (40 mg, 0.13 mmol) and calcium chloride (15 mg, 0.13 mmol) were added, and the reaction mixture was stirred at room temperature for an additional 2 hours. After removal of solvents in vacuo, the residue was purified by reversed phase HPLC (Column: DIKMA Diamonsil C18(2), 5 μm; Mobile phase A: 0.225% formic acid in water; Mobile phase B: 0.225% formic acid in acetonitrile; Gradient: 15% to 45% B) to provide the product as a yellow solid. Yield: 4.0 mg, 12 μmol, 9%. LCMS m/z 322.1 [M+H]$^+$. $^1$H NMR (400 MHz, CDCl$_3$) δ 8.49 (dd, J=4.8, 1.3 Hz, 1H), 8.20 (dd, J=8.2, 1.4 Hz, 1H), 7.77-7.82 (m, 1H), 7.36-7.43 (m, 3H), 4.80-4.89 (m, 2H), 4.18-4.26 (m, 2H), 2.39-2.50 (m, 2H).

Example 9

Azetidin-1-yl[3-(4-chloro-3,5-difluorophenyl)-3H-imidazo[4,5-b]pyridin-2-yl]methanone (9)

Step 1. Synthesis of N-(4-chloro-3,5-difluorophenyl)-3-nitropyridin-2-amine (C17)

A mixture of 4-chloro-3,5-difluoroaniline (1.64 g, 10.0 mmol), 2-chloro-3-nitropyridine (1.56 g, 9.84 mmol) and cesium carbonate (6.56 g, 20.1 mmol) in N,N-dimethylformamide (30 mL) was stirred at 80° C. for 36 hours. The reaction mixture was cooled to room temperature, diluted with water (200 mL) and extracted with ethyl acetate (3×200 mL). The combined organic layers were washed with saturated aqueous sodium chloride solution (5×50 mL), dried over sodium sulfate, filtered, concentrated in vacuo and purified by chromatography on silica gel (Gradient: 0% to 5% ethyl acetate in petroleum ether) to provide the product as a yellow solid. Yield: 200 mg, 0.70 mmol, 7%. $^1$H NMR (400 MHz, CDCl$_3$) δ 10.23 (br s, 1H), 8.55-8.61 (m, 2H), 7.52 (br d, J=9 Hz, 2H), 6.96-7.01 (m, 1H).

Step 2. Synthesis of N$^2$-(4-chloro-3,5-difluorophenyl)pyridine-2,3-diamine (C18)

To a solution of N-(4-chloro-3,5-difluorophenyl)-3-nitropyridin-2-amine (C17) (100 mg, 0.35 mmol) in a 1:1 mixture of tetrahydrofuran and water (20 mL) was added ammonium chloride (148 mg, 2.77 mmol) followed by zinc (182 mg, 2.78 mmol), and the reaction mixture was stirred at room temperature for 2 hours. It was then diluted with water (10 mL) and

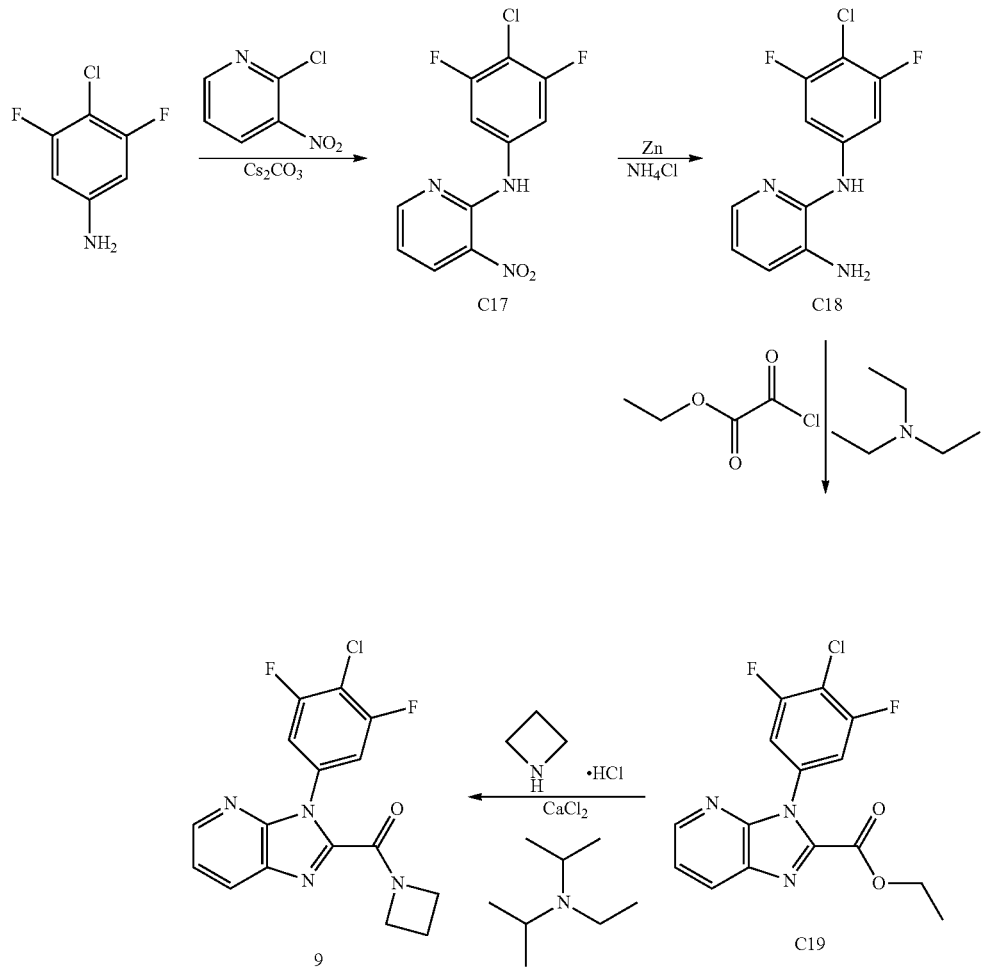

extracted with ethyl acetate (3×20 mL); the combined organic layers were washed with saturated aqueous sodium chloride solution (20 mL), dried over sodium sulfate, filtered, and concentrated in vacuo to afford the product as a yellow solid. This material was used directly in the following step. Yield: 80 mg, 0.31 mmol, 89%.

Step 3. Synthesis of ethyl 3-(4-chloro-3,5-difluorophenyl)-3H-imidazo[4,5-b]pyridine-2-carboxylate (C19)

$N^2$-(4-Chloro-3,5-difluorophenyl)pyridine-2,3-diamine (C18) was converted to the product using the method described for synthesis of C16 in Example 8. The product was obtained as a yellow solid. Yield: 40 mg, 0.12 mmol, 41%. $^1$H NMR (400 MHz, CDCl$_3$) δ 8.56 (dd, J=4.7, 1.3 Hz, 1H), 8.30 (dd, J=8.1, 1.5 Hz, 1H), 7.44 (dd, J=8.2, 4.7 Hz, 1H), 7.11-7.15 (m, 2H), 4.46 (q, J=7.2 Hz, 2H), 1.43 (t, J=7.2 Hz, 3H).

Step 4. Synthesis of azetidin-1-yl[3-(4-chloro-3,5-difluorophenyl)-3H-imidazo[4,5-b]pyridin-2-yl]methanone (9)

Ethyl 3-(4-chloro-3,5-difluorophenyl)-3H-imidazo[4,5-b]pyridine-2-carboxylate (C19) was converted to the product using the method described for synthesis of 8 in Example 8. The product was obtained as a yellow solid. Yield: 7.9 mg, 23 μmol, 39%. LCMS m/z 349.1 [M+H]$^+$. $^1$H NMR (400 MHz, CDCl$_3$) δ 8.50 (dd, J=4.7, 1.4 Hz, 1H), 8.19 (dd, J=8.1, 1.4 Hz, 1H), 7.39 (dd, J=8.1, 4.7 Hz, 1H), 7.10-7.15 (m, 2H), 4.80-4.85 (m, 2H), 4.19-4.25 (m, 2H), 2.40-2.49 (m, 2H).

Example 10

Azetidin-1-yl[3-(4-chloro-3-fluorophenyl)-3H-imidazo[4,5-b]pyridin-2-yl]methanone (10)

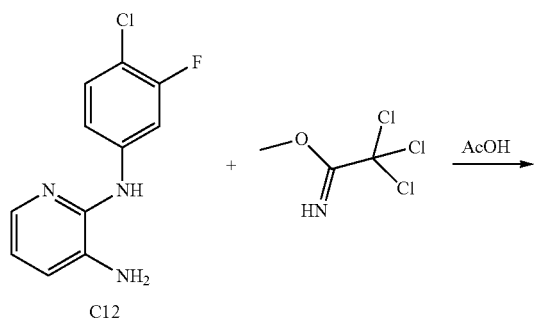

C12

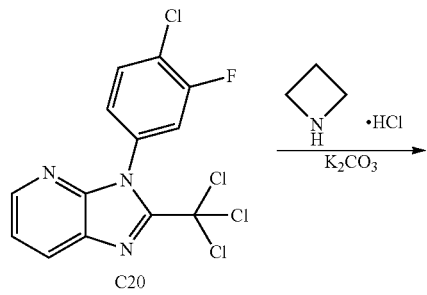

C20

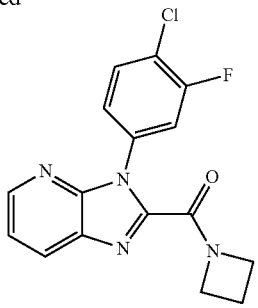

10

Step 1. Synthesis of 3-(4-chloro-3-fluorophenyl)-2-(trichloromethyl)-3H-imidazo[4,5-b]pyridine (C20)

Methyl 2,2,2-trichloroethanimidoate (0.743 mL, 6.00 mmol) was added to a solution of $N^2$-(4-chloro-3-fluorophenyl)pyridine-2,3-diamine (C12) (951 mg, 4.00 mmol) in acetic acid (4 mL), and the reaction mixture was stirred at room temperature for 5 hours. After concentration in vacuo, the residue was purified via chromatography on silica gel (Gradient: 5% to 100% ethyl acetate in heptane) to afford the product as a white solid. Yield: 1.04 g, 2.85 mmol, 71%. LCMS m/z 366.0 [M+H]$^+$. $^1$H NMR (400 MHz, CDCl$_3$) δ 8.49 (dd, J=4.7, 1.5 Hz, 1H), 8.27 (dd, J=8.1, 1.5 Hz, 1H), 7.64 (ddd, J=8.5, 7.8, 0.3 Hz, 1H), 7.42 (dd, J=8.1, 4.7 Hz, 1H), 7.39 (ddd, J=8.8, 2.4, 0.2 Hz, 1H), 7.32 (ddd, J=8.5, 2.4, 1.3 Hz, 1H).

Step 2. Synthesis of azetidin-1-yl[3-(4-chloro-3-fluorophenyl)-3H-imidazo[4,5-b]pyridin-2-yl]methanone (10)

3-(4-Chloro-3-fluorophenyl)-2-(trichloromethyl)-3H-imidazo[4,5-b]pyridine (C20) (50 mg, 0.14 mmol) was dissolved in a 3:1 mixture of acetonitrile and water (1.4 mL). Azetidine hydrochloride (25.6 mg, 0.274 mmol) was added, followed by an aqueous solution of potassium carbonate (4 M, 0.15 mL, 0.60 mmol), and the reaction mixture was heated at 50° C. for 22 hours, then at 80° C. for 3 hours, and finally at 100° C. for 18 hours. The layers were separated, and the organic layer was concentrated in vacuo; purification via reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 30% to 50% B) afforded the product. Yield: 17 mg, 51 μmol, 36%. LCMS m/z 331.1, 333.1 [M+H]$^+$. $^1$H NMR (600 MHz, DMSO-d$_6$) δ 8.45 (dd, J=4.6, 1.5 Hz, 1H), 8.30 (dd, J=7.9, 1.3 Hz, 1H), 7.76 (dd, J=8.3, 8.3 Hz, 1H), 7.73 (dd, J=10.1, 2.2 Hz, 1H), 7.46 (dd, J=8.1, 4.6 Hz, 1H), 7.40-7.43 (m, 1H), 4.64-4.68 (m, 2H), 4.02-4.07 (m, 2H), 2.29-2.35 (m, 2H).

Method A

Synthesis of Examples from 2-Chloro-3-nitropyridine and Amines

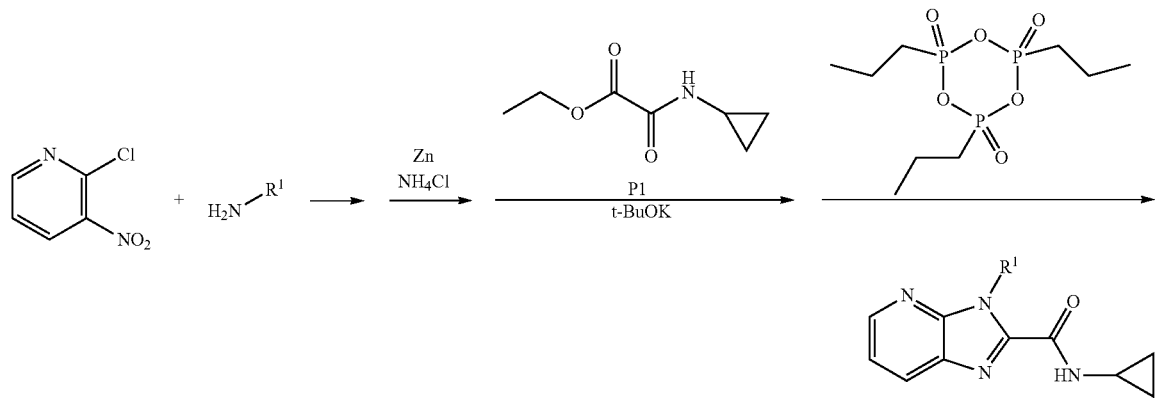

The requisite amine (0.20 mmol) was combined with a solution of 2-chloro-3-nitropyridine (31.7 mg, 0.200 mmol) in tetrahydrofuran (0.1 mL) and polyethylene glycol 400 (PEG 400, 0.1 mL); if an amine salt was used, triethylamine (28 µL, 0.20 mmol) was also added. The reaction mixture was shaken at 150° C. for 1-1.5 hours, then cooled to room temperature. To this was added tetrahydrofuran (0.4 mL) and a solution of ammonium chloride (85.6 mg, 1.60 mmol) in water (0.4 mL), followed by zinc (approximately 105 mg, 1.6 mmol). The reaction mixture was shaken at 65° C. for 1.5 hours, then partitioned between water (1 mL) and ethyl acetate (2.5 mL). The organic layer was eluted through a 6 mL solid phase extraction cartridge filled with sodium sulfate (approximately 1 g). This extraction was repeated twice, and the combined eluates from the cartridge were concentrated in vacuo. To the crude residue was added a solution of ethyl (cyclopropylamino)(oxo)acetate (P1) (47 mg, 0.30 mmol) in 1-methylpyrrolidin-2-one (0.2 mL) and a solution of potassium tert-butoxide in tetrahydrofuran (1 M, 0.3 mL, 0.3 mmol); this reaction mixture was shaken at 120° C. for 30 minutes, then cooled to room temperature and treated with acetic acid (18 µL, 0.31 mmol). 2,4,6-Tripropyl-1,3,5,2,4,6-trioxatriphosphinane 2,4,6-trioxide (T3P, 50% weight solution in ethyl acetate, 254 mg, 0.40 mmol) was added, and the reaction mixture was shaken at 120° C. for 24 hours. The reaction mixture was then partitioned between ethyl acetate (2.5 mL) and aqueous sodium hydroxide solution (1 M, 1.5 mL); the organic layer was eluted through a 6 mL solid phase extraction cartridge filled with sodium sulfate (approximately 1 g). This extraction was repeated twice, and the combined eluates from the cartridge were concentrated in vacuo and purified via reversed phase HPLC using one of the following systems: 1) Column: Waters XBridge C18, 5 µm; Mobile phase A: 0.03% ammonium hydroxide in water (v/v); Mobile phase B: 0.03% ammonium hydroxide in acetonitrile (v/v); Gradient: 20% to 60% B or 10% to 100% B; 2) Column: Waters Sunfire C18, 5 µm; Mobile phase A: 0.05% trifluoroacetic acid in water (v/v); Mobile phase B: 0.05% trifluoroacetic acid in acetonitrile (v/v); Gradient: 10% to 100% B.

Using the methodology described above for Examples 1-10, the compounds in Table 1 and Table 2 were also made (See Tables 1 and 2 for characterization data).

TABLE 1

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 11 | (structure shown) | Example 1$^2$; C12 | $^1$H NMR (600 MHz, DMSO-d$_6$), δ 8.46 (dd, J = 4.6, 1.5 Hz, 1H), 8.28 (dd, J = 8.1, 1.5 Hz, 1H), 7.81 (dd, J = 8.3, 8.3 Hz, 1H), 7.74 (dd, J = 10.1, 2.2 Hz, 1H), 7.47 (dd, J = 8.1, 4.6 Hz, 1H), 7.41-7.44 (m, 1H), 3.15 (s, 3H), 2.98 (s, 3H); 319.0, 321.0 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 12 | 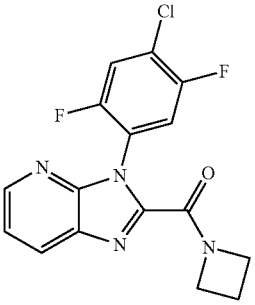 ·CF$_3$COOH | Example 10 | $^1$H NMR (600 MHz, DMSO-d$_6$), δ 8.46-8.49 (m, 1H), 8.32-8.36 (m, 1H), 7.90-7.96 (m, 2H), 7.47-7.51 (m, 1H), 4.71 (dd, J = 7.7, 7.7 Hz, 2H), 4.06 (dd, J = 7.7, 7.4 Hz, 2H), 2.30-2.37 (m, 2H); 349.1, 351.1 |
| 13 | 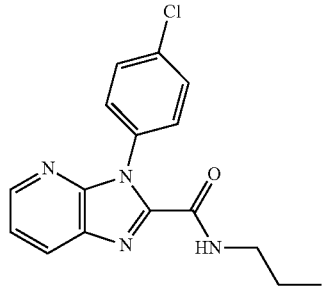 [SMILES: CCCNC(=O)c1nc2cccnc2n1-c1ccc(Cl)cc1] | Example 6; C10 | characteristic peaks: 8.46-8.53 (m, 1H), 8.15 (br d, J = 8 Hz, 1H), 7.63-7.73 (br m, 1H), 7.53 (br d, J = 8 Hz, 2H), 7.39 (br d, J = 8 Hz, 2H), 3.33-3.43 (m, 2H), 0.99 (t, J = 7.3 Hz, 3H); 314.8 |
| 14 | 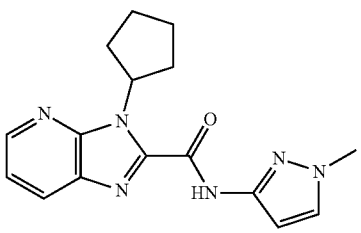 [SMILES: Cn1ccc(NC(=O)c2nc3cccnc3n2C2CCCC2)n1] | C7$^3$ | 10.09 (br s, 1H), 8.49 (dd, J = 4.6, 1.5 Hz, 1H), 8.07 (dd, J = 8.2, 1.5 Hz, 1H), 7.32 (d, J = 2.3 Hz, 1H), 7.29 (dd, J = 8.2, 4.6 Hz, 1H), 6.78 (d, J = 2.3 Hz, 1H), 6.22-6.33 (m, 1H), 3.87 (s, 3H), 2.55-2.67 (m, 2H), 2.08-2.21 (m, 4H), 1.70-1.83 (m, 2H); 311.0 |
| 15 | 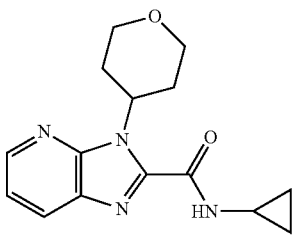 [SMILES: O=C(NC1CC1)c1nc2cccnc2n1C1CCOCC1] | Example 2 | $^1$H NMR (400 MHz, CD$_3$OD), δ 8.47 (dd, J = 4.7, 1.4 Hz, 1H), 8.09 (dd, J = 8.2, 1.4 Hz, 1H), 7.36 (dd, J = 8.2, 4.6 Hz, 1H), 5.68 (tt, J = 12, 4 Hz, 1H), 4.13 (dd, J = 11.5, 4.5 Hz, 2H), 3.60 (ddd, J = 12.4, 11.8, 1.5 Hz, 2H), 3.03-3.15 (m, 2H), 2.89-2.96 (m, 1H), 1.81-1.89 (m, 2H), 0.83-0.90 (m, 2H), 0.69-0.76 (m, 2H); 286.9 |
| 16 | 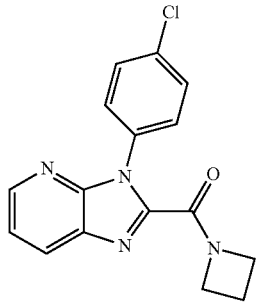 [SMILES: O=C(c1nc2cccnc2n1-c1ccc(Cl)cc1)N1CCC1] | Example 10; C9 | $^1$H NMR (600 MHz, DMSO-d$_6$), δ 8.44 (dd, J = 4.7, 1.3 Hz, 1H), 8.28 (dd, J = 8.1, 1.3 Hz, 1H), 7.56 (br AB quartet, J$_{AB}$ = 8.7 Hz, Δν$_{AB}$ = 39.2 Hz, 4H), 7.45 (dd, J = 8.1, 4.7 Hz, 1H), 4.63 (dd, J = 7.8, 7.7 Hz, 2H), 4.04 (dd, J = 7.8, 7.7 Hz, 2H), 2.28-2.35 (m, 2H); 313.1, 315.1 |

TABLE 1-continued

| Example Number | Structure | Method of Preparation; Non-commercial Starting Materials | ¹H NMR (400 MHz, CDCl₃), δ (ppm); Mass spectrum, observed ion m/z [M + H]⁺ or HPLC retention time¹ (minutes); Mass spectrum m/z [M + H]⁺ (unless otherwise indicated) |
|---|---|---|---|
| 17 | 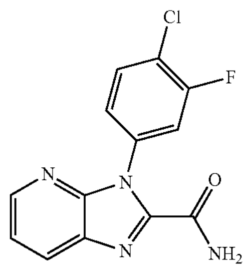 [SMILES: NC(=O)c1nc2cccnc2n1-c1ccc(Cl)c(F)c1] | Example 7; C12 | 8.52 (dd, J = 4.7, 1.3 Hz, 1H), 8.19 (dd, J = 8.2, 1.3 Hz, 1H), 7.59 (dd, J = 8.2, 8.2 Hz, 1H), 7.41 (dd, J = 8.1, 4.7 Hz, 1H), 7.28-7.32 (m, 1H), 7.20-7.24 (m, 1H); 290.8 |
| 18 | 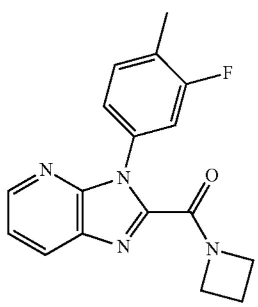 [SMILES: Cc1ccc(-n2c(C(=O)N3CCC3)nc3cccnc32)cc1F] | Example 3⁴ | 8.49 (d, J = 4.4 Hz, 1H), 8.15 (d, J = 7.6 Hz, 1H), 7.31-7.38 (m, 2H), 7.10-7.16 (m, 2H), 4.73-4.80 (m, 2H), 4.16-4.24 (m, 2H), 2.36 (s, 3H), 2.36-2.45 (m, 2H); 311.0 |
| 19 | 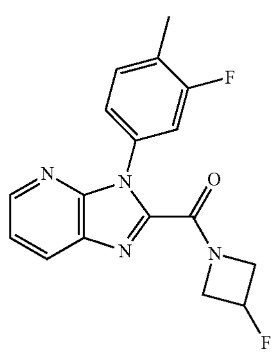 [SMILES: Cc1ccc(-n2c(C(=O)N3CC(F)C3)nc3cccnc32)cc1F] | Example 3⁴ | 8.45 (dd, J = 4.8, 1.3 Hz, 1H), 8.30 (dd, J = 8.2, 1.1 Hz, 1H), 7.38-7.49 (m, 3H), 7.23-7.27 (m, 1H), 5.49 (br d, $J_{HF}$ = 57 Hz, 1H), 4.93-5.05 (m, 1H), 4.63-4.76 (m, 1H), 4.32-4.44 (m, 1H), 4.04-4.16 (m, 1H), 2.33 (s, 3H); 329.0 |
| 20 | 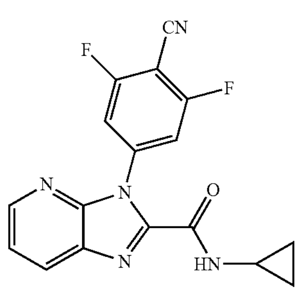 [SMILES: N#Cc1c(F)cc(-n2c(C(=O)NC3CC3)nc3cccnc32)cc1F] | Example 7 | 8.50 (dd, J = 4.7, 1.5 Hz, 1H), 8.17 (dd, J = 8.2, 1.5 Hz, 1H), 7.67 (br d, 1H), 7.44 (dd, J = 8.1, 4.7 Hz, 1H), 7.21-7.25 (m, 2H), 2.83-2.90 (m, 1H), 0.88-0.94 (m, 2H), 0.69-0.74 (m, 2H); 340.1 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 21 | (structure) | Example 3$^4$ | 8.51 (dd, J = 4.6, 1.2 Hz, 1H), 8.19 (dd, J = 8.2, 1.1 Hz, 1H), 7.57 (dd, J = 8.3, 8.0 Hz, 1H), 7.39 (dd, J = 8.2, 4.6 Hz, 1H), 7.27 (dd, J = 8.8, 2.3 Hz, 1H), 7.16-7.22 (m, 1H), 5.33-5.54 (m, J$_{HF}$ = 57 Hz, 1H), 5.08-5.20 (m, 1H), 4.85-4.98 (m, 1H), 4.40-4.52 (m, 1H), 4.23-4.36 (m, 1H); 348.9 |
| 22 | (structure) | Example 3$^4$ | 8.49 (dd, J = 4.7, 1.4 Hz, 1H), 8.18 (dd, J = 8.2, 1.4 Hz, 1H), 7.47 (dd, J = 8.4, 7.4 Hz, 1H), 7.37 (dd, J = 8.1, 4.8 Hz, 1H), 7.28-7.35 (m, 2H), 4.69-4.96 (br m, 2H), 4.16-4.26 (m, 2H), 2.37-2.47 (m, 2H); 331.0 |
| 23 | (structure) | Example 3$^4$ | 8.50 (dd, J = 4.8, 1.5 Hz, 1H), 8.15 (dd, J = 8.1, 1.4 Hz, 1H), 7.66 (br s, 1H), 7.45 (dd, J = 9.0, 7.4 Hz, 1H), 7.40 (dd, J = 8.1, 4.7 Hz, 1H), 7.31-7.37 (m, 2H), 2.83-2.89 (m, 1H), 0.84-0.91 (m, 2H), 0.68-0.73 (m, 2H); 330.9 |
| 24 | (structure) | Example 5; C10 | characteristic peaks: 9.94 (br s, 1H), 8.52 (dd, J = 4.8, 1.5 Hz, 1H), 8.20 (dd, J = 8.2, 1.4 Hz, 1H), 7.56 (br d, J = 8.8 Hz, 2H), 7.43 (br d, J = 8.7 Hz, 2H), 7.40 (dd, J = 8.2, 4.6 Hz, 1H), 6.68 (d, J = 2.1 Hz, 1H), 3.85 (s, 3H); 352.9 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 25 | 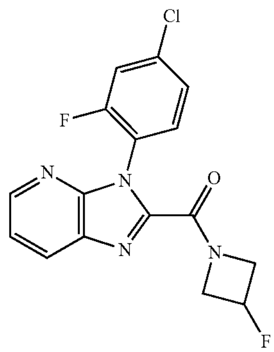 [SMILES: O=C(c1nc2cccnc2n1-c1ccc(Cl)cc1F)N1CC(F)C1] | Example 3$^4$ | 8.51 (dd, J = 4.8, 1.4 Hz, 1H), 8.20 (dd, J = 8.2, 1.4 Hz, 1H), 7.46 (dd, J = 8.4, 7.9 Hz, 1H), 7.39 (dd, J = 8.2, 4.8 Hz, 1H), 7.29-7.37 (m, 2H), 5.33-5.54 (m, J$_{HF}$ = 57 Hz, 1H), 4.8-5.3 (v br m, 2H), 4.40-4.54 (m, 1H), 4.23-4.37 (m, 1H); 348.9 |
| 26 | 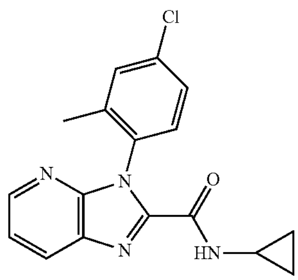 [SMILES: Cc1cc(Cl)ccc1-n1c(C(=O)NC2CC2)nc2cccnc21] | Example 3$^4$ | 8.49 (dd, J = 4.8, 1.1 Hz, 1H), 8.15 (dd, J = 7.9, 1.1 Hz, 1H). 7.66 (br s, 1H), 7.32-7.43 (m, 3H), 7.19 (d, J = 8.2 Hz, 1H), 2.81-2.89 (m, 1H), 1.98 (s, 3H), 0.83-0.89 (m, 2H), 0.66-0.71 (m, 2H); 327.0 |
| 27 | 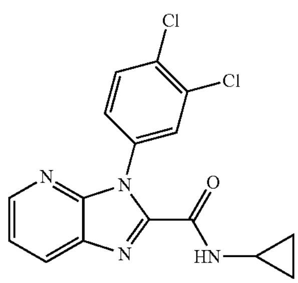 | Method A | 2.97 minutes; 347.0, 349.0 |
| 28 | 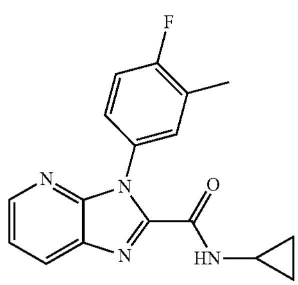 | Method A | 2.59 minutes; 311.1 |
| 29 | 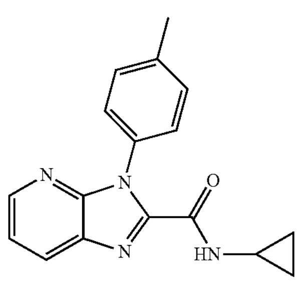 [SMILES: Cc1ccc(-n2c(C(=O)NC3CC3)nc3cccnc32)cc1] | Method A | 2.51 minutes; 293.1 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time[1] (minutes); Mass spectrum m/z [M + H]$^+$ (unless otherwise indicated) |
|---|---|---|---|
| 30 | (3,4,5-trifluorophenyl-imidazopyridine-cyclopropylamide) ·CF$_3$COOH | Method A | 2.70 minutes; 333.0 |
| 31 | (4-fluoro-3-cyanophenyl-imidazopyridine-cyclopropylamide) | Method A | 2.46 minutes; 322.1 |
| 32 | (4-fluoro-3-chlorophenyl-imidazopyridine-cyclopropylamide) | Method A | 2.53 minutes; 331.0, 333.0 |
| 33 | (4-methyl-3-chlorophenyl-imidazopyridine-cyclopropylamide) | Method A | 2.90 minutes; 327.0, 329.0 |
| 34 | (4-chloro-2-methylphenyl-imidazopyridine-azetidinylamide) | Example 3[4] | 8.48 (dd, J = 4.8, 1.5 Hz, 1H), 8.18 (dd, J = 8.2, 1.4 Hz, 1H), 7.30-7.40 (m, 3H), 7.17 (d, J = 8.3 Hz, 1H), 4.75-4.92 (m, 2H), 4.15-4.22 (m, 2H), 2.36-2.46 (m, 2H), 1.99 (s, 3H); 327.0 |

TABLE 1-continued

| Example Number | Structure | Method of Preparation; Non-commercial Starting Materials | 1H NMR (400 MHz, CDCl3), δ (ppm); Mass spectrum, observed ion m/z [M + H]+ or HPLC retention time1 (minutes); Mass spectrum m/z [M + H]+ (unless otherwise indicated) |
|---|---|---|---|
| 35 | 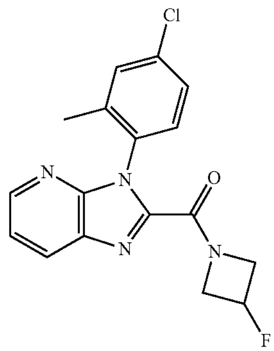 [SMILES: Cc1cc(Cl)ccc1-n1c(C(=O)N2CC(F)C2)nc2cccnc21] | Example 3[4] | presumed to be a mixture of rotamers; 8.50 (dd, J = 4.6, 1.4 Hz, 1H), 8.20 (br d, J = 8.0 Hz, 1H), 7.31-7.42 (m, 3H), 7.14-7.19 (m, 1H), 5.32-5.52 (m, $J_{HF}$ = 57 Hz, 1H), 5.04-5.26 (m, 1H), 4.82-5.03 (m, 1H), 4.38-4.50 (m, 1H), 4.21-4.34 (m, 1H), 1.99 and 1.97 (2 s, total 3H); 345.0 |
| 36 | 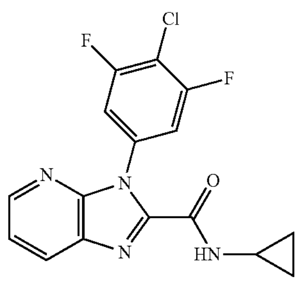 [SMILES: O=C(NC1CC1)c1nc2cccnc2n1-c1cc(F)c(Cl)c(F)c1] | Example 9 | 8.51 (dd, J = 4.6, 1.5 Hz, 1H), 8.15 (dd, J = 8.2, 1.5 Hz, 1H), 7.68 (br s, 1H), 7.41 (dd, J = 8.2, 4.8 Hz, 1H), 7.11-7.16 (m, 2H), 2.82-2.90 (m, 1H), 0.86-0.92 (m, 2H), 0.68-0.73 (m, 2H); 349.1 |
| 37 | 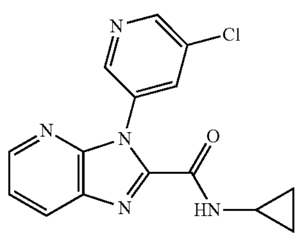 [SMILES: O=C(NC1CC1)c1nc2cccnc2n1-c1cncc(Cl)c1] | Example 2[5] | 8.72 (d, J = 2.0 Hz, 1H), 8.60 (d, J = 2.1 Hz, 1H), 8.51 (dd, J = 4.6, 1.4 Hz, 1H), 8.16 (dd, J = 8.2, 1.4 Hz, 1H), 7.86 (dd, J = 2.1, 2.0 Hz, 1H), 7.69 (br s, 1H), 7.42 (dd, J = 8.3, 4.6 Hz, 1H), 2.83-2.91 (m, 1H), 0.86-0.92 (m, 2H), 0.68-0.73 (m, 2H); 314.1, 316.0 |
| 38 | 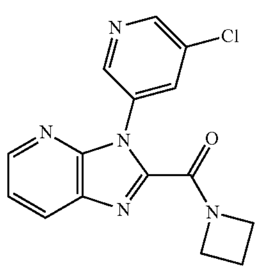 [SMILES: O=C(c1nc2cccnc2n1-c1cncc(Cl)c1)N1CCC1] | Example 37 | 8.69 (d, J = 2.3 Hz, 1H), 8.56 (d, J = 1.9 Hz, 1H), 8.50 (dd, J = 4.6, 1.3 Hz, 1H), 8.20 (dd, J = 8.1, 1.3 Hz, 1H), 7.85-7.88 (m, 1H), 7.40 (dd, J = 8.2, 4.6 Hz, 1H), 4.82-4.87 (m, 2H), 4.19-4.25 (m, 2H), 2.39-2.49 (m, 2H); 313.9, 315.9 |
| 39 | 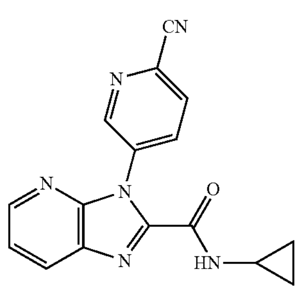 [SMILES: N#Cc1ccc(-n2c(C(=O)NC3CC3)nc3cccnc32)cn1] | Example 7[6] | 8.84 (br d, J = 2.4 Hz, 1H), 8.50 (dd, J = 4.7, 1.4 Hz, 1H), 8.18 (dd, J = 8.2, 1.4 Hz, 1H), 8.03 (dd, half of ABX pattern, J = 8.3, 2.4 Hz, 1H), 7.91 (dd, half of ABX pattern, J = 8.3, 0.5 Hz, 1H), 7.72 (br s, 1H), 7.44 (dd, J = 8.2, 4.8 Hz, 1H), 2.82-2.90 (m, 1H), 0.87-0.93 (m, 2H), 0.68-0.73 (m, 2H); 305.1 |

TABLE 1-continued

| Example Number | Structure | Method of Preparation; Non-commercial Starting Materials | ¹H NMR (400 MHz, CDCl₃), δ (ppm); Mass spectrum, observed ion m/z [M + H]⁺ or HPLC retention time¹ (minutes); Mass spectrum m/z [M + H]⁺ (unless otherwise indicated) |
|---|---|---|---|
| 40 | 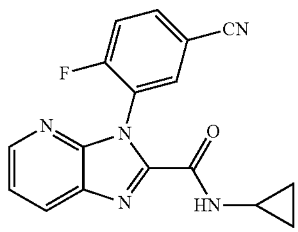 [SMILES: N#Cc1ccc(F)c(-n2c(C(=O)NC3CC3)nc3cccnc32)c1] | Example 7 | 8.50 (dd, J = 4.9, 1.4 Hz, 1H), 8.17 (dd, J = 8.3, 1.3 Hz, 1H), 7.81-7.87 (m, 2H), 7.68 (br s, 1H), 7.39-7.45 (m, 2H), 2.82-2.89 (m, 1H), 0.86-0.92 (m, 2H), 0.68-0.74 (m, 2H); 322.2 |
| 41 | 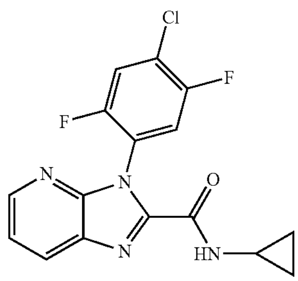 [SMILES: O=C(NC1CC1)c1nc2cccnc2n1-c1cc(F)c(Cl)cc1F] | Example 7⁷ | 8.51 (dd, J = 4.6, 1.5 Hz, 1H), 8.16 (dd, J = 8.0, 1.3 Hz, 1H), 7.64 (br s, 1H), 7.32-7.43 (m, 3H), 2.83-2.90 (m, 1H), 0.85-0.92 (m, 2H), 0.68-0.74 (m, 2H); 349.1 |
| 42 | 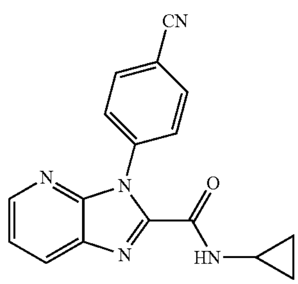 [SMILES: N#Cc1ccc(-n2c(C(=O)NC3CC3)nc3cccnc32)cc1] | Method A | 2.32 minutes; 304.1 |
| 43 | 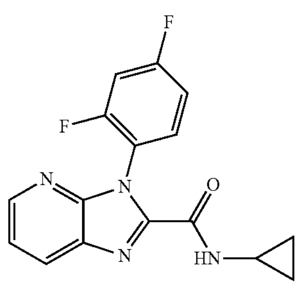 | Method A | 2.47 minutes; 315.1 |
| 44 | 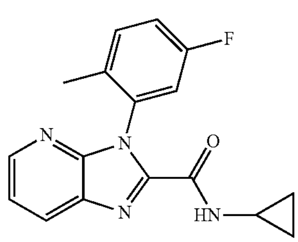 [SMILES: Cc1ccc(F)cc1-n1c(C(=O)NC2CC2)nc2cccnc21] | Method A | 2.54 minutes; 311.1 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 45 | 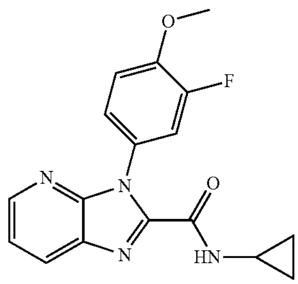 [SMILES: COc1ccc(-n2c(C(=O)NC3CC3)nc3cccnc32)cc1F] | Method A | 2.44 minutes; 327.1 |
| 46 | 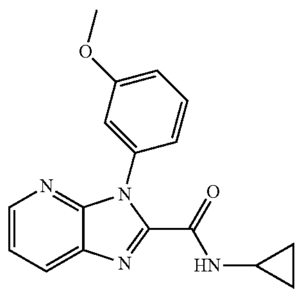 [SMILES: COc1cccc(-n2c(C(=O)NC3CC3)nc3cccnc32)c1] | Method A | 2.34 minutes; 309.1 |
| 47 | 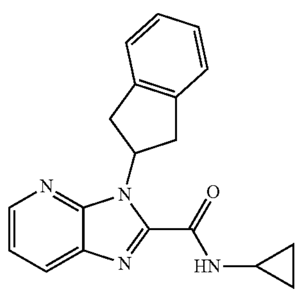 [SMILES: O=C(NC1CC1)c1nc2cccnc2n1C1Cc2ccccc2C1] | Method A | 3.25 minutes; 319.1 |
| 48 | 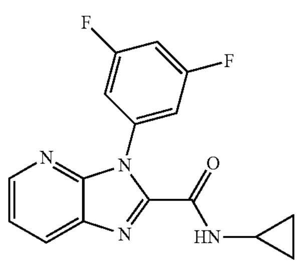 [SMILES: O=C(NC1CC1)c1nc2cccnc2n1-c1cc(F)cc(F)c1] | Method A | 2.55 minutes; 315.0 |
| 49 | 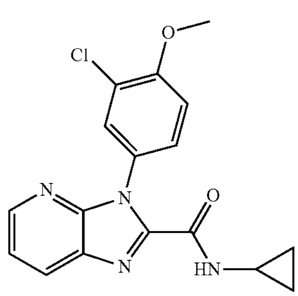 [SMILES: COc1ccc(-n2c(C(=O)NC3CC3)nc3cccnc32)cc1Cl] | Method A | 2.66 minutes; 343.0, 345.0 |

TABLE 1-continued

| Example Number | Structure | Non-commercial Starting Materials | Method of Preparation; $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 50 | 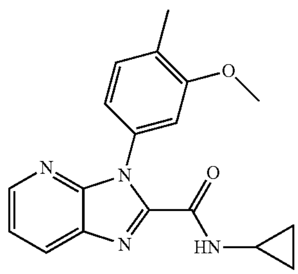 [SMILES: COc1cc(-n2c(C(=O)NC3CC3)nc3cccnc32)ccc1C] | | Method A 2.60 minutes; 323.1 |
| 51 | 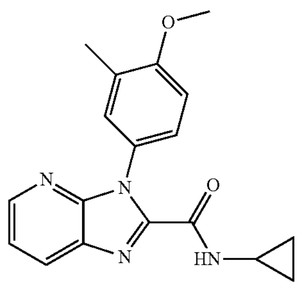 [SMILES: COc1ccc(-n2c(C(=O)NC3CC3)nc3cccnc32)cc1C] | | Method A 2.60 minutes; 323.1 |
| 52 | 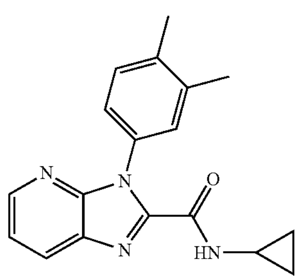 [SMILES: Cc1ccc(-n2c(C(=O)NC3CC3)nc3cccnc32)cc1C] | | Method A 2.71 minutes; 307.1 |
| 53 | 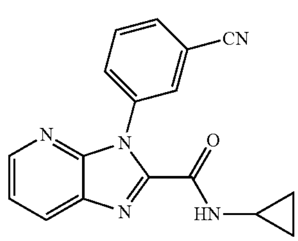 [SMILES: N#Cc1cccc(-n2c(C(=O)NC3CC3)nc3cccnc32)c1] | | Method A 2.30 minutes; 304.1 |
| 54 | 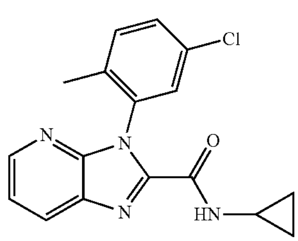 [SMILES: Cc1ccc(Cl)cc1-n1c(C(=O)NC2CC2)nc2cccnc21] | | Method A 2.85 minutes; 327.1, 329.1 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 55 | 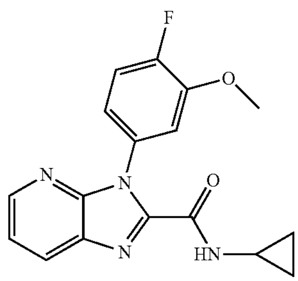 [SMILES: COc1cc(-n2c(C(=O)NC3CC3)nc3cccnc32)ccc1F] | Method A | 2.40 minutes; 327.1 |
| 56 | 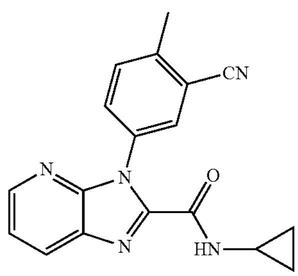 | Method A | 2.52 minutes; 318.1 |
| 57 | 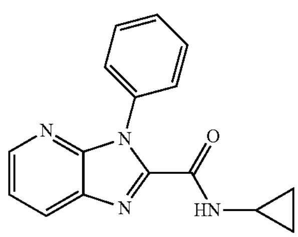 [SMILES: O=C(NC1CC1)c1nc2cccnc2n1-c1ccccc1] | Method A | 2.13 minutes; 279.1 |
| 58 | 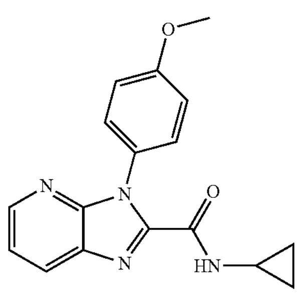 [SMILES: COc1ccc(-n2c(C(=O)NC3CC3)nc3cccnc32)cc1] | Method A | 2.33 minutes; 309.1 |
| 59 | 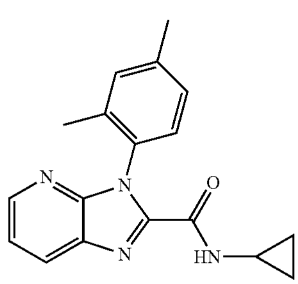 [SMILES: Cc1ccc(-n2c(C(=O)NC3CC3)nc3cccnc32)c(C)c1] | Method A | 2.74 minutes; 307.1 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 60 | 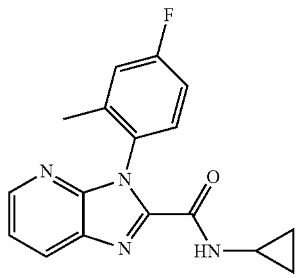 [SMILES: Cc1cc(F)ccc1-n1c(C(=O)NC2CC2)nc2cccnc21] | Method A | 2.55 minutes; 311.1 |
| 61 | 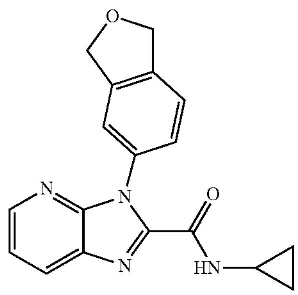 [SMILES: O=C(NC1CC1)c1nc2cccnc2n1-c1ccc2c(c1)COC2] | Method A | 2.10 minutes; 321.1 |
| 62 | 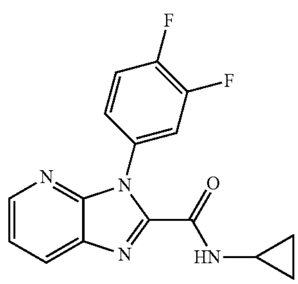 [SMILES: O=C(NC1CC1)c1nc2cccnc2n1-c1ccc(F)c(F)c1] | Method A | 2.52 minutes; 315.0 |
| 63 | 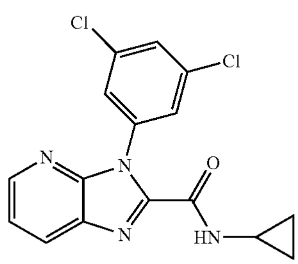 [SMILES: O=C(NC1CC1)c1nc2cccnc2n1-c1cc(Cl)cc(Cl)c1] | Method A | 3.06 minutes; 347.0, 349.0 |
| 64 | 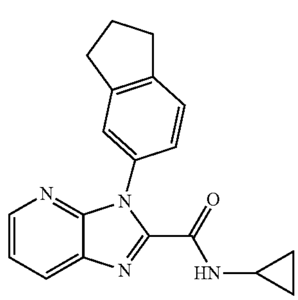 [SMILES: O=C(NC1CC1)c1nc2cccnc2n1-c1ccc2c(c1)CCC2] | Method A | 2.83 minutes; 319.1 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 65 | 3-fluorophenyl imidazo[4,5-b]pyridine-2-carboxamide, N-cyclopropyl | Method A | 2.39 minutes; 297.1 |
| 66 | 3,5-dimethoxyphenyl imidazo[4,5-b]pyridine-2-carboxamide, N-cyclopropyl | Method A | 2.46 minutes; 339.1 |
| 67 | 2-fluoro-4-methylphenyl imidazo[4,5-b]pyridine-2-carboxamide, N-cyclopropyl | Method A | 2.69 minutes; 311.1 |
| 68 | 4-fluorophenyl imidazo[4,5-b]pyridine-2-carboxamide, N-cyclopropyl | Method A | 2.35 minutes; 297.1 |
| 69 | 3-chlorophenyl imidazo[4,5-b]pyridine-2-carboxamide, N-cyclopropyl | Example 7[8] | 8.50 (dd, J = 4.8, 1.3 Hz, 1H), 8.14 (dd, J = 8.2, 1.1 Hz, 1H), 7.69 (br s, 1H), 7.47-7.53 (m, 2H), 7.45 (br s, 1H), 7.33-7.41 (m, 2H), 2.83-2.90 (m, 1H), 0.83-0.90 (m, 2H), 0.67-0.73 (m, 2H); 312.9 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 70 | 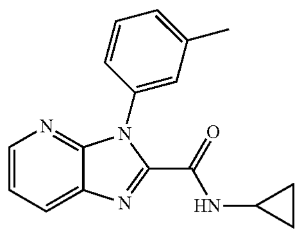 [SMILES: Cc1cccc(-n2c(C(=O)NC3CC3)nc3cccnc32)c1] | Method A | 2.48 minutes; 293.1 |
| 71 | 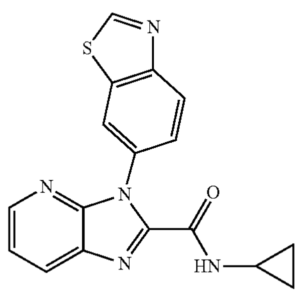 [SMILES: O=C(NC1CC1)c1nc2cccnc2n1-c1ccc2ncsc2c1] | Method A | 2.13 minutes; 336.0 |
| 72 | 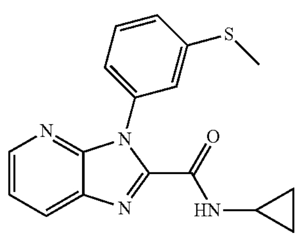 [SMILES: CSc1cccc(-n2c(C(=O)NC3CC3)nc3cccnc32)c1] | Method A | 2.65 minutes; 325.0 |
| 73 | 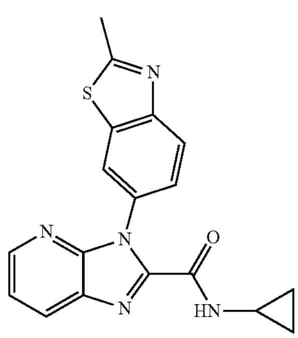 [SMILES: Cc1nc2ccc(-n3c(C(=O)NC4CC4)nc4cccnc43)cc2s1] | Method A | 2.27 minutes; 350.0 |
| 74 | 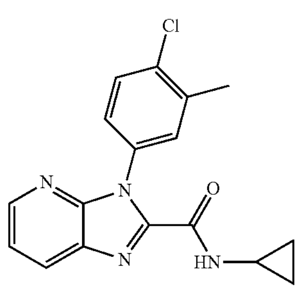 [SMILES: Cc1cc(-n2c(C(=O)NC3CC3)nc3cccnc32)ccc1Cl] | Method A | 2.85 minutes; 327.1, 329.0 |

TABLE 1-continued
| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 75 | 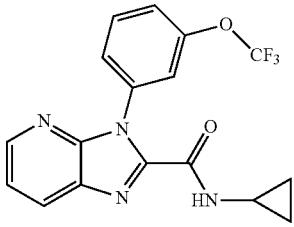 [SMILES: O=C(NC1CC1)c1nc2cccnc2n1-c1cccc(OC(F)(F)F)c1] | Method A | 2.95 minutes; 363.0 |
| 76 | 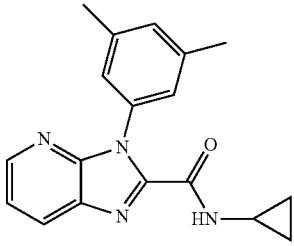 [SMILES: Cc1cc(C)cc(-n2c(C(=O)NC3CC3)nc3cccnc32)c1] | Method A | 2.71 minutes; 307.1 |
| 77 | 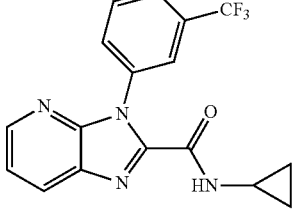 | Method A | 2.88 minutes; 347.0 |
| 78 | 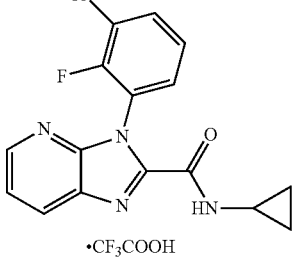 | Method A | 2.79 minutes; 331.0, 333.0 |
| 79 | 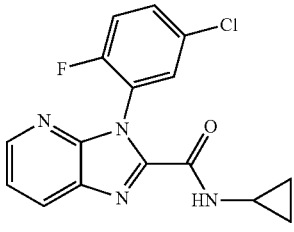 | Method A | 2.76 minutes; 331.0, 333.0 |

TABLE 1-continued

| Example Number | Structure | Method of Preparation; Non-commercial Starting Materials | $^1$H NMR (400 MHz, CDCl$_3$), δ (ppm); Mass spectrum, observed ion m/z [M + H]$^+$ or HPLC retention time[1] (minutes); Mass spectrum m/z [M + H]$^+$ (unless otherwise indicated) |
|---|---|---|---|
| 80 | (quinolinyl-imidazopyridine-2-carboxamide, N-cyclopropyl) ·CF$_3$COOH | Method A | 1.59 minutes; 330.1 |

[1] Conditions for analytical HPLC. Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.
[2] Ethyl (dimethylamino)(oxo)acetate was employed in place of ethyl (cyclopropylamino)(oxo)acetate (P1).
[3] Hydrolysis of C7 with lithium hydroxide afforded the corresponding carboxylic acid; this was condensed with 1-methyl-1H-pyrazol-3-amine using 1-[3-(dimethylamino)propyl]-3-ethylcarbodiimide hydrochloride and 1H-benzotriazol-1-ol.
[4] N,N-Diisopropylethylamine was utilized in the final step.
[5] The requisite N$^2$-(5-chloropyridin-3-yl)pyridine-2,3-diamine was prepared via reaction of 2-chloro-3-nitropyridine with 5-chloropyridin-3-amine using palladium(II) acetate and 4,5-bis(diphenylphosphino)-9,9-dimethylxanthene, followed by treatment with Raney nickel.
[6] 5-[(3-Nitropyridin-2-yl)amino]pyridine-2-carbonitrile was prepared by the method used for synthesis of C17 in Example 9.
[7] N-(4-Chloro-2,5-difluorophenyl)-3-nitropyridin-2-amine was prepared by the method used for synthesis of C17 in Example 9.
[8] N-(3-Chlorophenyl)-3-nitropyridin-2-amine was prepared by heating 2-chloro-3-nitropyridine with 3-chloroaniline at 150° C.

TABLE 2

| Example Number | Structure | Method of Preparation; Non-commercial Starting Materials | Mass spectrum, observed ion m/z [M + H]$^+$ |
|---|---|---|---|
| 81 | (5-chloropyridin-3-yl imidazopyridine-2-carboxamide, N-ethyl) | Example 2[1] | 302.0 |
| 82 | (2-trifluoromethylpyridin-4-yl imidazopyridine-2-carboxamide, N-cyclopropyl) | Example 7[2] | 348.2 |
| 83 | (5-methoxypyridin-3-yl imidazopyridine-2-carboxamide, N-cyclopropyl) | Example 7 | 309.9 |

TABLE 2-continued

| Example Number | Structure | Method of Preparation; Non-commercial Starting Materials | Mass spectrum, observed ion m/z [M + H]+ |
| --- | --- | --- | --- |
| 84 | 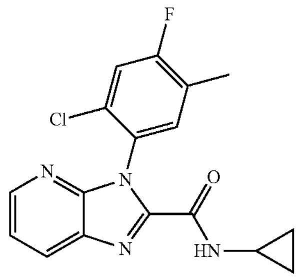 [SMILES: Cc1cc(-n2c(C(=O)NC3CC3)nc3cccnc32)c(Cl)cc1F] | Method A | 345.0, 347.0 |
| 85 | 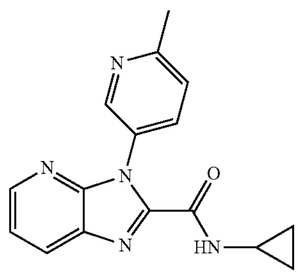 [SMILES: Cc1ccc(-n2c(C(=O)NC3CC3)nc3cccnc32)cn1] | Method A | 294.1 |
| 86 | 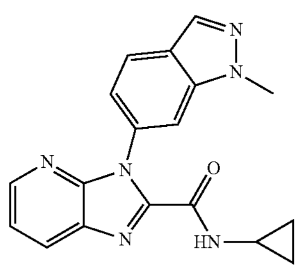 [SMILES: Cn1ncc2ccc(-n3c(C(=O)NC4CC4)nc4cccnc43)cc21] | Method A | 333.1 |
| 87 | 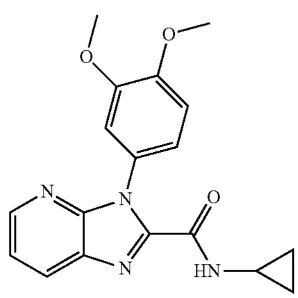 [SMILES: COc1ccc(-n2c(C(=O)NC3CC3)nc3cccnc32)cc1OC] | Method A | 339.1 |
| 88 | 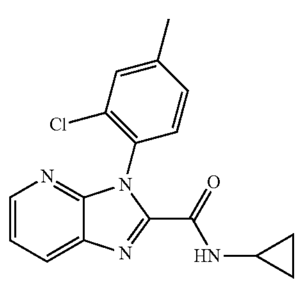 [SMILES: Cc1ccc(-n2c(C(=O)NC3CC3)nc3cccnc32)c(Cl)c1] | Method A | 327.1, 329.0 |

TABLE 2-continued

| Example Number | Structure | Method of Preparation; Non-commercial Starting Materials | Mass spectrum, observed ion m/z [M + H]+ |
|---|---|---|---|
| 89 | 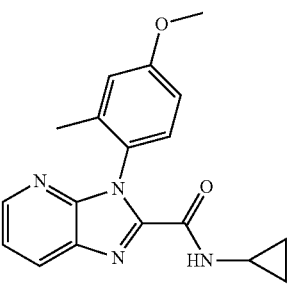 [SMILES: COc1ccc(-n2c(C(=O)NC3CC3)nc3cccnc32)c(C)c1] | Method A | 323.1 |
| 90 | 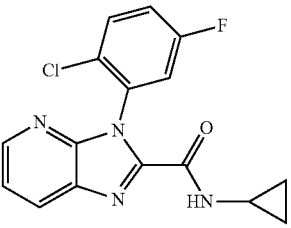 [SMILES: O=C(NC1CC1)c1nc2cccnc2n1-c1cc(F)ccc1Cl] | Method A | 331.0, 333.0 |
| 91 | 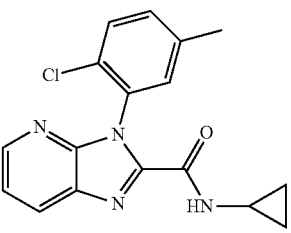 [SMILES: Cc1ccc(Cl)c(-n2c(C(=O)NC3CC3)nc3cccnc32)c1] | Method A | 327.1, 329.0 |
| 92 | 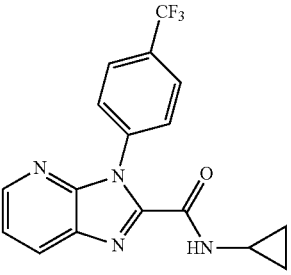 | Method A | 347.1 |

[1] See footnote 5 in Table 1.
[2] 3-Nitro-N-[2-(trifluoromethyl)pyridin-4-yl]pyridin-2-amine was prepared from 2-chloro-3-nitropyridine and 2-(trifluoromethyl)pyridin-4-amine using the method for synthesis of C17 in Example 9.

The binding affinity of the compounds in Examples 1-92 for the PDE4B isoform is shown in column 2 of Table 3 below, and the affinity of these compounds for the PDE4D isoform is shown in column 3. A review of the data shows that selected compounds have an enhanced binding affinity for the PDE4B isoform over the PDE4D isoform. For example, the data for Examples 2, 15, 17, 81, 82, 83, 85, 90 and 91 shows that these compounds display at least about a 2-fold selectivity over the PDE4D isoform. The data for Examples 13, 14, 21, 25, 35, 40, 47, 77, 88, 89 and 92 shows that these compounds display at least about a 5-fold selectivity over the PDE4D isoform. The data for Examples 19, 20, 33, 38, 41, 44, 49, 57, 61, 72, 75, 79 and 87 shows that these compounds display at least about a 10-fold to selectivity over the PDE4D isoform. The data for Examples 6, 9, 10, 11, 12, 22, 27, 31, 34, 37, 39, 43, 56, 59, 60, 63, 66, 69, 70, 73, 74, 78 and 80 shows that these compounds display at least about a 20-fold selectivity over the PDE4D isoform. The data for Examples 4, 7, 18, 36, 46, 62, 67 and 71 shows that these compounds display at least about a 40-fold selectivity over the PDE4D isoform. The data for Examples 1, 3, 8, 16, 23, 26, 28, 30, 32, 33, 42, 45, 48, 50, 51, 52, 54, 55, 58, 64, 65, 68 and 76 shows that these compounds display at least about a 50-fold selectivity over the PDE4D isoform.

The PDE4B and PDE4D binding affinity for the compounds of the present invention was determined utilizing the following biological assay(s):

Biological Assays

A portion of the human PDE4D3 coding sequence (amino acids 50 to 672 from the sequence with accession number Q08499-2) was cloned into the baculovirus expression vector pFastBac (Invitrogen) engineered to include a C-terminal His6 affinity tag to aid in purification as described in Seeger, T. F. et al., Brain Research 985 (2003) 113-126. The recombinant Bacmid was isolated and used to transfect insect cells to generate a viral stock. To generate cell paste for purification, insect cells were infected and cells were harvested 72 hours after infection. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE4 were pooled, diluted with Q Buffer A (50 mM Tris HCl pH 8, 4% glycerol, 100 mM NaCl, 1 mM TCEP, Protease inhibitors EDTA-free (Roche)) to reduce NaCl to ~200 mM, and loaded on a Q Sepharose (GE Healthcare) column. After washing with Q buffer A to baseline, PDE4D was eluted with a gradient from 10% to 60% of Buffer B (50 mM Tris HCl pH 8, 1 M NaCl, 4% glycerol, 1 mM TCEP). PDE4D fractions were analyzed by SDS-PAGE Coomassie blue staining, pooled based on purity, frozen and stored at −80° C.

Human PDE4B1 coding sequence (amino acids 122 to 736 from the sequence with accession number Q07343) with the mutations resulting in the amino acid substitutions S134E, S654A, S659A, and S661A was cloned into the baculovirus expression vector pFastBac (Invitrogen) engineered to include a N-terminal His6 affinity tag to aid in purification followed by a thrombin cleavage site. The recombinant Bacmid was isolated and used to transfect insect cells to generate a viral stock. To generate cell paste for purification, insect cells were infected with the virus stock and cells were harvested 72 hours after infection as described in Seeger, T. F. et al., Brain Research 985 (2003) 113-126. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE4 were pooled, diluted with Q buffer A (20 mM Tris HCl pH 8, 5% glycerol, 1 mM TCEP) to reduce NaCl to ~100 mM and loaded on a Source 15Q (GE Healthcare) column. After washing with Q buffer A/10% buffer B to baseline, PDE4D was eluted with a gradient from 10% to 60% of Buffer B (20 mM Tris HCl pH 8, 1 M NaCl, 5% glycerol, 1 mM TCEP). PDE4D fractions were analyzed by SDS-PAGE Coomassie blue staining, pooled based on purity, frozen and stored at −80° C.

The PDE4B and 4D assays use scintillation proximity assay (SPA) technology to measure the inhibition of human recombinant PDE4B and PDE4D enzyme activity by compounds in vitro. The PDE4B and 4D assays are run in parallel using identical parameters, except for the concentration of enzyme (~32 pM PDE4B and ~16 pM PDE4D). The assays are performed in a 384-well format with 50 μL assay buffer (50 mM Tris pH 7.5; 1.3 mM $MgCl_2$; 0.01% Brij) containing enough PDE4B and PDE4D to convert ~20% of substrate (1 μM cAMP consisting of 20 nM $^3$H-cAMP+980 μM cold cAMP) and a range of inhibitors. Reactions are incubated for 30 min at 25° C. The addition of 20 μL of 8 mg/mL yitrium silicate SPA beads (PerkinElmer) stops the reaction. The plates are sealed (TopSeal, PerkinElmer) and the beads are allowed to settle for 8 hrs, after which they are read on the Trilux Microbeta overnight.

TABLE 3

| Example Number | Human PDE4B FL; $IC_{50}$ (nM)[a] | Human PDE4D FL; $IC_{50}$ (μM)[a] | IUPAC Name |
| --- | --- | --- | --- |
| 1 | 31.8[b] | 2.21[b] | N-Cyclopropyl-3-(3-fluoro-4-methylphenyl)-3H-imidazo[4,5-b]pyridine-2-carboxamide |
| 2 | 426 | 1.27[b] | 3-Cyclopentyl-N-cyclopropyl-3H-imidazo[4,5-b]pyridine-2-carboxamide |
| 3 | 131[b] | 7.95[b] | 3-(4-Chlorophenyl)-N-cyclopropyl-3H-imidazo[4,5-b]pyridine-2-carboxamide |
| 4 | 18.4[b] | 0.908[b] | 3-(4-Chloro-3-fluorophenyl)-N-cyclopropyl-3H-imidazo[4,5-b]pyridine-2-carboxamide |
| 5 | 54.1 | 5.64 | 3-(4-Chloro-3-fluorophenyl)-N-(1-methyl-1H-pyrazol-3-yl)-3H-imidazo[4,5-b]pyridine-2-carboxamide |
| 6 | 38.1[b] | 0.778[b] | 3-(4-Chloro-3-fluorophenyl)-N-propyl-3H-imidazo[4,5-b]pyridine-2-carboxamide |
| 7 | 40.8[b] | 1.88[b] | 3-(4-Cyano-3-fluorophenyl)-N-cyclopropyl-3H-imidazo[4,5-b]pyridine-2-carboxamide |
| 8 | 16.0 | 0.910 | 4-[2-(Azetidin-1-ylcarbonyl)-3H-imidazo[4,5-b]pyridin-3-yl]-2-fluorobenzonitrile |
| 9 | 14.2[b] | 0.420[b] | Azetidin-1-yl[3-(4-chloro-3,5-difluorophenyl)-3H-imidazo[4,5-b]pyridin-2-yl]methanone |
| 10 | 15.2[b] | 0.567[b] | Azetidin-1-yl[3-(4-chloro-3-fluorophenyl)-3H-imidazo[4,5-b]pyridin-2-yl]methanone |
| 11 | 405 | 9.64 | 3-(4-Chloro-3-fluorophenyl)-N,N-dimethyl-3H-imidazo[4,5-b]pyridine-2-carboxamide |
| 12 | 99.4 | 1.52 | Azetidin-1-yl[3-(4-chloro-2,5-difluorophenyl)-3H-imidazo[4,5-b]pyridin-2-yl]methanone, trifluoroacetate salt |
| 13 | 944 | 6.64[b] | 3-(4-Chlorophenyl)-N-propyl-3H-imidazo[4,5-b]pyridine-2-carboxamide |
| 14 | 822 | 4.38 | 3-Cyclopentyl-N-(1-methyl-1H-pyrazol-3-yl)-3H-imidazo[4,5-b]pyridine-2-carboxamide |
| 15 | 1730 | 6.90 | N-Cyclopropyl-3-(tetrahydro-2H-pyran-4-yl)-3H-imidazo[4,5-b]pyridine-2-carboxamide |
| 16 | 196 | 5.50 | Azetidin-1-yl[3-(4-chlorophenyl)-3H-imidazo[4,5-b]pyridin-2-yl]methanone |
| 17 | 8510 | >30.0 | 3-(4-Chloro-3-fluorophenyl)-3H-imidazo[4,5-b]pyridine-2-carboxamide |

TABLE 3-continued

| Example Number | Human PDE4B FL; IC$_{50}$ (nM)[a] | Human PDE4D FL; IC$_{50}$ (μM)[a] | IUPAC Name |
|---|---|---|---|
| 18 | 48.7 | 2.14 | Azetidin-1-yl[3-(3-fluoro-4-methylphenyl)-3H-imidazo[4,5-b]pyridin-2-yl]methanone |
| 19 | 281 | 5.28 | (3-Fluoroazetidin-1-yl)[3-(3-fluoro-4-methylphenyl)-3H-imidazo[4,5-b]pyridin-2-yl]methanone |
| 20 | 13.8 | 0.262[b] | 3-(4-Cyano-3,5-difluorophenyl)-N-cyclopropyl-3H-imidazo[4,5-b]pyridine-2-carboxamide |
| 21 | 42.6 | 0.316 | [3-(4-Chloro-3-fluorophenyl)-3H-imidazo[4,5-b]pyridin-2-yl](3-fluoroazetidin-1-yl)methanone |
| 22 | 273 | 5.59 | Azetidin-1-yl[3-(4-chloro-2-fluorophenyl)-3H-imidazo[4,5-b]pyridin-2-yl]methanone |
| 23 | 632 | >30.0 | 3-(4-Chloro-2-fluorophenyl)-N-cyclopropyl-3H-imidazo[4,5-b]pyridine-2-carboxamide |
| 24 | 211 | >24.1 | 3-(4-Chlorophenyl)-N-(1-methyl-1H-pyrazol-3-yl)-3H-imidazo[4,5-b]pyridine-2-carboxamide |
| 25 | 910 | 5.84 | [3-(4-Chloro-2-fluorophenyl)-3H-imidazo[4,5-b]pyridin-2-yl](3-fluoroazetidin-1-yl)methanone |
| 26 | 319 | >17.9 | 3-(4-Chloro-2-methylphenyl)-N-cyclopropyl-3H-imidazo[4,5-b]pyridine-2-carboxamide |
| 27 | 12.2[b] | 0.511[b] | N-Cyclopropyl-3-(3,4-dichlorophenyl)-3H-imidazo[4,5-b]pyridine-2-carboxamide |
| 28 | 114 | 8.23 | N-Cyclopropyl-3-(4-fluoro-3-methylphenyl)-3H-imidazo[4,5-b]pyridine-2-carboxamide |
| 29 | 225 | >28.0[b] | N-Cyclopropyl-3-(4-methylphenyl)-3H-imidazo[4,5-b]pyridine-2-carboxamide |
| 30 | 5.77 | 0.333 | N-Cyclopropyl-3-(3,4,5-trifluorophenyl)-3H-imidazo[4,5-b]pyridine-2-carboxamide, trifluoroacetate salt |
| 31 | 87.5 | 2.55 | 3-(3-Cyano-4-fluorophenyl)-N-cyclopropyl-3H-imidazo[4,5-b]pyridine-2-carboxamide |
| 32 | 15.7 | 0.886 | 3-(3-Chloro-4-fluorophenyl)-N-cyclopropyl-3H-imidazo[4,5-b]pyridine-2-carboxamide |
| 33 | 15.9 | 1.23[b] | 3-(3-Chloro-4-methylphenyl)-N-cyclopropyl-3H-imidazo[4,5-b]pyridine-2-carboxamide |
| 34 | 399 | 10.2 | Azetidin-1-yl[3-(4-chloro-2-methylphenyl)-3H-imidazo[4,5-b]pyridin-2-yl]methanone |
| 35 | 1130 | 8.28 | [3-(4-Chloro-2-methylphenyl)-3H-imidazo[4,5-b]pyridin-2-yl](3-fluoroazetidin-1-yl)methanone |
| 36 | 5.65 | 0.255 | 3-(4-Chloro-3,5-difluorophenyl)-N-cyclopropyl-3H-imidazo[4,5-b]pyridine-2-carboxamide |
| 37 | 409 | 10.7 | 3-(5-Chloropyridin-3-yl)-N-cyclopropyl-3H-imidazo[4,5-b]pyridine-2-carboxamide |
| 38 | 466 | 6.67 | Azetidin-1-yl[3-(5-chloropyridin-3-yl)-3H-imidazo[4,5-b]pyridin-2-yl]methanone |
| 39 | 363 | 10.2 | 3-(6-Cyanopyridin-3-yl)-N-cyclopropyl-3H-imidazo[4,5-b]pyridine-2-carboxamide |
| 40 | 1710 | 15.2 | 3-(5-Cyano-2-fluorophenyl)-N-cyclopropyl-3H-imidazo[4,5-b]pyridine-2-carboxamide |
| 41 | 100 | 1.17 | 3-(4-Chloro-2,5-difluorophenyl)-N-cyclopropyl-3H-imidazo[4,5-b]pyridine-2-carboxamide |
| 42 | 276[b] | >22.4[b] | 3-(4-Cyanophenyl)-N-cyclopropyl-3H-imidazo[4,5-b]pyridine-2-carboxamide |
| 43 | 927 | >26.6 | N-Cyclopropyl-3-(2,4-difluorophenyl)-3H-imidazo[4,5-b]pyridine-2-carboxamide |
| 44 | 1660 | >29.0 | N-Cyclopropyl-3-(5-fluoro-2-methylphenyl)-3H-imidazo[4,5-b]pyridine-2-carboxamide |
| 45 | 205 | 14.8 | N-Cyclopropyl-3-(3-fluoro-4-methoxyphenyl)-3H-imidazo[4,5-b]pyridine-2-carboxamide |
| 46 | 329 | 13.8 | N-Cyclopropyl-3-(3-methoxyphenyl)-3H-imidazo[4,5-b]pyridine-2-carboxamide |
| 47 | 1260 | 6.39 | N-Cyclopropyl-3-(2,3-dihydro-1H-inden-2-yl)-3H-imidazo[4,5-b]pyridine-2-carboxamide |
| 48 | 88.9 | 4.82 | N-Cyclopropyl-3-(3,5-difluorophenyl)-3H-imidazo[4,5-b]pyridine-2-carboxamide |
| 49 | 629 | 12.3 | 3-(3-Chloro-4-methoxyphenyl)-N-cyclopropyl-3H-imidazo[4,5-b]pyridine-2-carboxamide |
| 50 | 339 | >30.0 | N-Cyclopropyl-3-(3-methoxy-4-methylphenyl)-3H-imidazo[4,5-b]pyridine-2-carboxamide |
| 51 | 207 | 13.2 | N-Cyclopropyl-3-(4-methoxy-3-methylphenyl)-3H-imidazo[4,5-b]pyridine-2-carboxamide |
| 52 | 271 | 25.8 | N-Cyclopropyl-3-(3,4-dimethylphenyl)-3H-imidazo[4,5-b]pyridine-2-carboxamide |

TABLE 3-continued

| Example Number | Human PDE4B FL; IC$_{50}$ (nM)$^a$ | Human PDE4D FL; IC$_{50}$ (μM)$^a$ | IUPAC Name |
|---|---|---|---|
| 53 | 287 | 3.40 | 3-(3-Cyanophenyl)-N-cyclopropyl-3H-imidazo[4,5-b]pyridine-2-carboxamide |
| 54 | 329 | 19.2 | 3-(5-Chloro-2-methylphenyl)-N-cyclopropyl-3H-imidazo[4,5-b]pyridine-2-carboxamide |
| 55 | 304 | >23.7 | N-Cyclopropyl-3-(4-fluoro-3-methoxyphenyl)-3H-imidazo[4,5-b]pyridine-2-carboxamide |
| 56 | 167 | 4.85 | 3-(3-Cyano-4-methylphenyl)-N-cyclopropyl-3H-imidazo[4,5-b]pyridine-2-carboxamide |
| 57 | 1160 | >19.7 | N-Cyclopropyl-3-phenyl-3H-imidazo[4,5-b]pyridine-2-carboxamide |
| 58 | 506 | >30.0 | N-Cyclopropyl-3-(4-methoxyphenyl)-3H-imidazo[4,5-b]pyridine-2-carboxamide |
| 59 | 1020 | >30.0 | N-Cyclopropyl-3-(2,4-dimethylphenyl)-3H-imidazo[4,5-b]pyridine-2-carboxamide |
| 60 | 1200 | >30.0 | N-Cyclopropyl-3-(4-fluoro-2-methylphenyl)-3H-imidazo[4,5-b]pyridine-2-carboxamide |
| 61 | 1580 | >30.0 | N-Cyclopropyl-3-(1,3-dihydro-2-benzofuran-5-yl)-3H-imidazo[4,5-b]pyridine-2-carboxamide |
| 62 | 34.9 | 1.49$^b$ | N-Cyclopropyl-3-(3,4-difluorophenyl)-3H-imidazo[4,5-b]pyridine-2-carboxamide |
| 63 | 68.0 | 2.55 | N-Cyclopropyl-3-(3,5-dichlorophenyl)-3H-imidazo[4,5-b]pyridine-2-carboxamide |
| 64 | 206 | 15.7 | N-Cyclopropyl-3-(2,3-dihydro-1H-inden-5-yl)-3H-imidazo[4,5-b]pyridine-2-carboxamide |
| 65 | 188 | 10.9 | N-Cyclopropyl-3-(3-fluorophenyl)-3H-imidazo[4,5-b]pyridine-2-carboxamide |
| 66 | 759 | 19.4 | N-Cyclopropyl-3-(3,5-dimethoxyphenyl)-3H-imidazo[4,5-b]pyridine-2-carboxamide |
| 67 | 619 | >30.0 | N-Cyclopropyl-3-(2-fluoro-4-methylphenyl)-3H-imidazo[4,5-b]pyridine-2-carboxamide |
| 68 | 219 | 11.9 | N-Cyclopropyl-3-(4-fluorophenyl)-3H-imidazo[4,5-b]pyridine-2-carboxamide |
| 69 | 70.9$^b$ | 1.91$^b$ | 3-(3-Chlorophenyl)-N-cyclopropyl-3H-imidazo[4,5-b]pyridine-2-carboxamide |
| 70 | 421 | 14.9 | N-Cyclopropyl-3-(3-methylphenyl)-3H-imidazo[4,5-b]pyridine-2-carboxamide |
| 71 | 155 | 6.34 | 3-(1,3-Benzothiazol-6-yl)-N-cyclopropyl-3H-imidazo[4,5-b]pyridine-2-carboxamide |
| 72 | 40.9 | 0.753 | N-Cyclopropyl-3-[3-(methylsulfanyl)phenyl]-3H-imidazo[4,5-b]pyridine-2-carboxamide |
| 73 | 516 | 12.6 | N-Cyclopropyl-3-(2-methyl-1,3-benzothiazol-6-yl)-3H-imidazo[4,5-b]pyridine-2-carboxamide |
| 74 | 58.8 | 1.99 | 3-(4-Chloro-3-methylphenyl)-N-cyclopropyl-3H-imidazo[4,5-b]pyridine-2-carboxamide |
| 75 | 389 | 3.98 | N-Cyclopropyl-3-[3-(trifluoromethoxy)phenyl]-3H-imidazo[4,5-b]pyridine-2-carboxamide |
| 76 | 374 | >18.8 | N-Cyclopropyl-3-(3,5-dimethylphenyl)-3H-imidazo[4,5-b]pyridine-2-carboxamide |
| 77 | 1150 | 8.64 | N-Cyclopropyl-3-[3-(trifluoromethyl)phenyl]-3H-imidazo[4,5-b]pyridine-2-carboxamide |
| 78 | 387 | 11.4 | 3-(3-Chloro-2-fluorophenyl)-N-cyclopropyl-3H-imidazo[4,5-b]pyridine-2-carboxamide, trifluoroacetate salt |
| 79 | 106 | 1.76 | 3-(5-Chloro-2-fluorophenyl)-N-cyclopropyl-3H-imidazo[4,5-b]pyridine-2-carboxamide, trifluoroacetate salt |
| 80 | 1470 | >30.0 | N-Cyclopropyl-3-(quinolin-6-yl)-3H-imidazo[4,5-b]pyridine-2-carboxamide, trifluoroacetate salt |
| 81 | 8270 | >30.0 | 3-(5-Chloropyridin-3-yl)-N-ethyl-3H-imidazo[4,5-b]pyridine-2-carboxamide |
| 82 | 6070 | 17.5 | N-Cyclopropyl-3-[2-(trifluoromethyl)pyridin-4-yl]-3H-imidazo[4,5-b]pyridine-2-carboxamide |
| 83 | 13600 | >29.3 | N-Cyclopropyl-3-(5-methoxypyridin-3-yl)-3H-imidazo[4,5-b]pyridine-2-carboxamide |
| 84 | 16600 | >30.0 | 3-(2-Chloro-4-fluoro-5-methylphenyl)-N-cyclopropyl-3H-imidazo[4,5-b]pyridine-2-carboxamide |
| 85 | 7730 | >30.0 | N-Cyclopropyl-3-(6-methylpyridin-3-yl)-3H-imidazo[4,5-b]pyridine-2-carboxamide |
| 86 | 24500 | >30.0 | N-Cyclopropyl-3-(1-methyl-1H-indazol-6-yl)-3H-imidazo[4,5-b]pyridine-2-carboxamide |
| 87 | 2720 | >30.0 | N-Cyclopropyl-3-(3,4-dimethoxyphenyl)-3H-imidazo[4,5-b]pyridine-2-carboxamide |

TABLE 3-continued

| Example Number | Human PDE4B FL; IC$_{50}$ (nM)$^a$ | Human PDE4D FL; IC$_{50}$ (μM)$^a$ | IUPAC Name |
|---|---|---|---|
| 88 | 3700 | >30.0 | 3-(2-Chloro-4-methylphenyl)-N-cyclopropyl-3H-imidazo[4,5-b]pyridine-2-carboxamide |
| 89 | 3520 | >30.0 | N-Cyclopropyl-3-(4-methoxy-2-methylphenyl)-3H-imidazo[4,5-b]pyridine-2-carboxamide |
| 90 | 9230 | >30.0 | 3-(2-Chloro-5-fluorophenyl)-N-cyclopropyl-3H-imidazo[4,5-b]pyridine-2-carboxamide |
| 91 | 9420 | >30.0 | 3-(2-Chloro-5-methylphenyl)-N-cyclopropyl-3H-imidazo[4,5-b]pyridine-2-carboxamide |
| 92 | 3110 | >30.0 | N-Cyclopropyl-3-[4-(trifluoromethyl)phenyl]-3H-imidazo[4,5-b]pyridine-2-carboxamide |

$^a$Values represent the geometric mean of 2-6 determinations.
$^b$Value represents the geometric mean of ≥7 determinations.

What is claimed:
1. A compound of formula I:

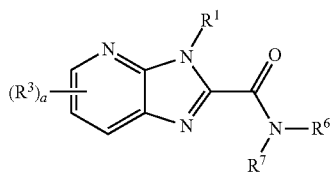

or a pharmaceutically acceptable salt thereof, wherein:
  $R^1$ is represented by a substituent selected from the group consisting of ($C_3$-$C_{10}$)cycloalkyl, a (4- to 10-membered)heterocycloalkyl, ($C_6$-$C_{10}$)aryl, and a (5- to 10-membered) heteroaryl; wherein said ($C_3$-$C_{10}$)cycloalkyl, ($C_6$-$C_{10}$)aryl and (5- to 10-membered)heteroaryl are substituted with $(R^2)_b$; and said (4- to 10-membered)heterocycloalkyl is optionally substituted at one to five carbon atoms with a substituent independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy, and cyano, and optionally substituted at each available nitrogen with ($C_1$-$C_6$)alkyl;
  $R^2$ is represented by a substituent independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio; —C(O)NR$^4$R$^5$, hydroxy, and cyano;
  $R^3$, if present, at each occurrence is represented by a substituent independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy, and cyano;
  $R^4$ and $R^5$ are each represented by a substituent independently selected from the group consisting of hydrogen, ($C_1$-$C_6$)alkyl, and ($C_3$-$C_6$)cycloalkyl;
  one of $R^6$ and $R^7$ is represented by a substituent selected from the group consisting of hydrogen, ($C_1$-$C_6$)alkyl, —(CH$_2$)$_m$—($C_3$-$C_{10}$)cycloalkyl, —(CH$_2$)$_m$-(4- to 10-membered)-heterocycloalkyl, —(CH$_2$)$_m$—($C_6$-$C_{10}$)aryl, and —(CH$_2$)$_m$-(5- to 10-membered)heteroaryl and the other is represented by a substituent selected from the group consisting of ($C_1$-$C_6$)alkyl, —(CH$_2$)$_m$—($C_3$-$C_{10}$)cycloalkyl, —(CH$_2$)$_m$-(4- to 10-membered)-heterocycloalkyl, —(CH$_2$)$_m$—($C_6$-$C_{10}$)aryl, and —(CH$_2$)$_m$-(5- to 10-membered)heteroaryl; wherein:
  i) said $R^6$ and $R^7$ ($C_1$-$C_6$)alkyl substituent is optionally substituted with one to five substituents independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, and cyano;
  ii) said $R^6$ and $R^7$ ($C_3$-$C_{10}$)cycloalkyl substituent is optionally substituted with one to five substituents independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy and cyano;
  iii) said $R^6$ and $R^7$ ($C_6$-$C_{10}$)aryl substituent is optionally substituted with one to five substituents independently selected from the group consisting of halogen, ($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy and cyano;
  iv) said $R^6$ and $R^7$ (5- to 10-membered)heteroaryl substituent is optionally substituted with one to five substituents independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy, and cyano; and
  v) said $R^6$ and $R^7$ (4- to 10-membered)heterocycloalkyl substituent is optionally substituted at one to five carbon atoms with a substituent independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$^5$, hydroxy, and cyano, and optionally substituted at each available nitrogen with ($C_1$-$C_6$)alkyl; or $R^6$ and $R^7$ taken together with the nitrogen to which they are attached form a (4- to 10-membered)heterocycloalkyl, wherein said (4- to 10-membered) heterocycloalkyl is optionally substituted at one to five carbon atoms with a substituent independently selected from the group consisting of halogen, ($C_1$-$C_6$)alkyl, halo($C_1$-$C_6$)alkyl, ($C_1$-$C_6$)alkoxy, halo($C_1$-$C_6$)alkoxy, ($C_1$-$C_6$)alkylthio, —C(O)NR$^4$R$_5$, hydroxy, and cyano;

a is represented by an integer selected from 0, 1, 2 or 3;

b is represented by an integer selected from 0, 1, 2, 3, 4 or 5; and m is represented by an integer selected from 0, 1, 2 or 3.

2. The compound according to claim 1, or a pharmaceutically acceptable salt thereof, wherein a is represented by the integer 0.

3. The compound according to claim 1, or a pharmaceutically acceptable salt thereof, wherein $R^1$ is represented by a (5 to 10-membered)heteroaryl and b is an integer selected from 0, 1, 2 or 3.

4. The compound according to claim 3, or a pharmaceutically acceptable salt thereof, wherein $R^1$ is represented by pyridinyl; b is an integer selected from 1, 2, or 3; and each $R^2$ is independently selected from the group consisting of chloro, fluoro, methyl, methoxy, trifluoromethyl, trifluoromethoxy, cyano, and methylthio.

5. The compound according to claim 4, or a pharmaceutically acceptable salt thereof, wherein $R^1$ is represented by the group consisting of 5-chloropyridin-3-yl, 6-methylpyridin-3-yl, 5-methoxypyridin-3-yl, 2-trifluoromethylpyridin-4-yl, and 6-cyanopyridin-3-yl.

6. The compound according to claim 3, or a pharmaceutically acceptable salt thereof, wherein $R^1$ is represented by 1-methyl-1H-indazol-5-yl, quinolin-6-yl, 1,3-benzothiazol-6-yl, and 2-methyl-1,3-benzothiazol-6-yl.

7. The compound according to claim 1, or a pharmaceutically acceptable salt thereof, wherein $R^1$ is represented by $(C_3-C_{10})$cycloalkyl, and b is and integer selected from 0, 1, 2, or 3.

8. The compound according to claim 7, or a pharmaceutically acceptable salt thereof, wherein $R^1$ is represented by cyclopentyl; b is an integer selected from 1, 2 or 3; and each $R^2$ is independently selected from the group consisting of chloro, fluoro, methyl, methoxy, trifluoromethyl, trifluoromethoxy, cyano, and methylthio.

9. The compound according to claim 1, or a pharmaceutically acceptable salt thereof, wherein $R^1$ is represented by a (4 to 10-membered)heterocycloalkyl optionally substituted at one to three carbon atoms with a substituent independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, —C(O)NR$^4$R$^5$, hydroxy, and cyano, and optionally substituted at each available nitrogen with a $(C_1-C_6)$alkyl.

10. The compound according to claim 9, or a pharmaceutically acceptable salt thereof, wherein $R^1$ is represented by tetrahydropyranyl optionally substituted at one to three carbon atoms with a substituent independently selected from the group consisting of chloro, fluoro, methyl, methoxy, trifluoromethyl, trifluoromethoxy, cyano, and methylthio.

11. The compound according to claim 1, or a pharmaceutically acceptable salt thereof, wherein $R^1$ is represented by $(C_6-C_{10})$aryl; b is an integer selected from 0, 1, 2 or 3; and when present each $R^2$ is independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, —C(O)NR$^4$R$^5$, hydroxy, and cyano.

12. The compound of claim 11, or a pharmaceutically acceptable salt thereof, wherein said $(C_6-C_{10})$aryl is selected from the group consisting of 2,3-dihydro-1H-inden-5-yl and 1,3-dihydro-2-benzofuran-5-yl.

13. A compound of formula Ia:

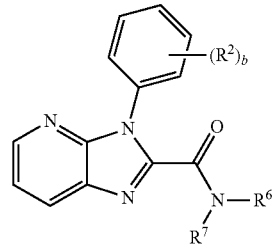

or a pharmaceutically acceptable salt thereof, wherein:
b is represented by an integer selected from 0, 1, 2, or 3;
each $R^2$, if present, is represented by a substituent independently selected from the group consisting of fluoro, chloro, cyano, methyl, trifluoromethyl, methylthio, methoxy, and trifluoromethoxy;
one of $R^6$ and $R^7$ is selected from the group consisting of hydrogen, $(C_1-C_6)$alkyl, —$(CH_2)_m$—$(C_3-C_{10})$cycloalkyl, and —$(CH_2)_m$-(5- to 10-membered)heteroaryl and the other is selected from the group consisting of $(C_1-C_6)$alkyl, —$(CH_2)_m$—$(C_3-C_{10})$cycloalkyl, and —$(CH_2)_m$-(5- to 10-membered)heteroaryl; wherein:
i) said $R^6$ and $R^7$ $(C_1-C_6)$alkyl substituent is optionally substituted with one to three substituents independently selected from the group consisting of halogen, $(C_1-C_6)$alkyl, halo$(C_1-C_6)$alkyl, $(C_1-C_6)$alkoxy, halo $(C_1-C_6)$alkoxy, $(C_1-C_6)$alkylthio, and cyano;
ii) said $R^6$ and $R^7$ $(C_3-C_{10})$cycloalkyl substituent is optionally substituted with one to three substituents independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, hydroxy, and cyano;
iii) said $R^6$ and $R^7$ (5- to 10-membered)heteroaryl substituent is optionally substituted with one to three substituents independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, hydroxy, and cyano; or $R^6$ and $R^7$ taken together with the nitrogen to which they are attached form a (4 to 6-membered)heterocycloalkyl, in which up to three carbon atoms of said heterocycloalkyl are optionally substituted with a substituent independently selected from the group consisting of halogen, $(C_1-C_6)$alkyl, halo$(C_1-C_6)$alkyl, $(C_1-C_6)$alkoxy, halo $(C_1-C_6)$alkoxy, $(C_1-C_6)$alkylthio, —C(O)NR$^4$R$^5$, hydroxy, and cyano;
wherein $R^4$ and $R^5$ are each independently selected from the group consisting of hydrogen and $(C_1-C_6)$alkyl;
and m is represented by an integer selected from 0, 1, or 2.

14. The compound according to claim 13, or a pharmaceutically acceptable salt thereof, wherein $R^6$ and $R^7$ taken together with the nitrogen to which they are attached form a (4- to 6-membered)heterocycloalkyl optionally substituted at one to three carbon atoms with halogen.

15. The compound of claim 14, or a pharmaceutically acceptable salt thereof, wherein $R^6$ and $R^7$ taken together with the nitrogen to which they are attached form azetidinyl, optionally substituted with one to three halogen.

16. The compound according to claim 15, or a pharmaceutically acceptable salt thereof, wherein said azetidinyl is selected from azetidin-1-yl or 3-fluoroazetidin-1-yl.

17. The compound according to claim 13, or a pharmaceutically acceptable salt thereof, wherein b is represented by an integer selected from 0, 1, 2, or 3; each $R^2$, if present, is represented by a substituent independently selected from the group consisting of fluoro, chloro, cyano, methyl, trifluoromethyl, methylthio, methoxy, and trifluoromethoxy; one of $R^6$ and $R^7$ is represented by hydrogen and the other represented by a substituent selected from the group consisting of $(C_1-C_6)$alkyl, $-(CH_2)_m-(C_3-C_6)$cycloalkyl, and $-(CH_2)_m$-(5- to 10-membered)heteroaryl; wherein:
  i) said $(C_1-C_6)$alkyl is optionally substituted with one to three substituents independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, and cyano;
  ii) said $(C_3-C_{10})$cycloalkyl is optionally substituted with one to three substituents independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, hydroxy, and cyano; and
  iii) said (5- to 10-membered)heteroaryl is optionally substituted with one to three substituents independently selected from the group consisting of halogen, $(C_1-C_6)$alkyl, halo$(C_1-C_6)$alkyl, $(C_1-C_6)$alkoxy, halo$(C_1-C_6)$alkoxy, $(C_1-C_6)$alkylthio, hydroxy, and cyano; and m is represented by an integer selected from 0, 1 or 2.

18. The compound according to claim 17, or a pharmaceutically acceptable salt thereof, wherein b is represented by an integer selected from 0, 1, 2, or 3; and each $R^2$, if present, is represented by a substituent independently selected from the group consisting of chloro, fluoro, methyl, and cyano; and one of $R^6$ and $R^7$ is represented by hydrogen and the other is represented by $(C_1-C_6)$alkyl.

19. The compound according to claim 18, or a pharmaceutically acceptable salt thereof, wherein one of $R^6$ and $R^7$ is represented by hydrogen and the other is represented by the group consisting of ethyl or propyl.

20. The compound according to claim 17, or a pharmaceutically acceptable salt thereof, wherein b is represented by an integer selected from 0, 1, 2, or 3; and each $R^2$, if present, is represented by a substituent independently selected from the group consisting of chloro, fluoro, methyl, and cyano; and one of $R^6$ and $R^7$ is represented by hydrogen and the other is represented by $-(CH_2)_m-(C_3-C_6)$cycloalkyl.

21. The compound according to claim 20, or a pharmaceutically acceptable salt thereof, wherein one of $R^6$ and $R^7$ is represented by hydrogen and the other is represented by cyclopropyl.

22. The compound according to claim 17, or a pharmaceutically acceptable salt thereof, wherein b is represented by an integer selected from 0, 1, 2, or 3; and each $R^2$, if present, is represented by a substituent independently selected from the group consisting of chloro, fluoro, methyl, and cyano; and one of $R^6$ and $R^7$ is represented by hydrogen and the other is represented by $-(CH_2)_m$-(5- to 10-membered)heteroaryl optionally substituted by a $(C_1-C_6)$alkyl.

23. The compound according to claim 22, or a pharmaceutically acceptable salt thereof, wherein one of $R^6$ and $R^7$ is represented by hydrogen and the other is represented by pyrazolyl optionally substituted by methyl.

24. The compound according to claim 23, or a pharmaceutically acceptable salt thereof, wherein one of $R^6$ and $R^7$ is represented by hydrogen and the other is represented by N-1-methyl-1H-pyrazol-3-yl.

25. A method of treating a patient suffering from a disease or condition mediated by the PDE4B isoform, comprising administering to said patient in need of said treatment a therapeutically effective amount of a compound of formula I according to claim 1, or a pharmaceutically acceptable salt thereof, wherein said disease or condition is selected from the group consisting of schizophrenia, depression, anxiety, and Alzheimer's disease.

26. A pharmaceutical composition comprising a compound according to claim 1, or a pharmaceutically acceptable salt thereof, and a pharmaceutically acceptable excipient.

27. A compound selected from the group consisting of:
  N-Cyclopropyl-3-(3-fluoro-4-methylphenyl)-3H-imidazo[4,5-b]pyridine-2-carboxamide;
  3-Cyclopentyl-N-cyclopropyl-3H-imidazo[4,5-b]pyridine-2-carboxamide;
  3-(4-Chlorophenyl)-N-cyclopropyl-3H-imidazo[4,5-b]pyridine-2-carboxamide;
  3-(4-Chloro-3-fluorophenyl)-N-cyclopropyl-3H-imidazo[4,5-b]pyridine-2-carboxamide;
  3-(4-Chloro-3-fluorophenyl)-N-(1-methyl-1H-pyrazol-3-yl)-3H-imidazo[4,5-b]pyridine-2-carboxamide;
  3-(4-Chloro-3-fluorophenyl)-N-propyl-3H-imidazo[4,5-b]pyridine-2-carboxamide;
  3-(4-Cyano-3-fluorophenyl)-N-cyclopropyl-3H-imidazo[4,5-b]pyridine-2-carboxamide;
  4-[2-(Azetidin-1-ylcarbonyl)-3H-imidazo[4,5-b]pyridin-3-yl]-2-fluorobenzonitrile;
  azetidin-1-yl[3-(4-chloro-3,5-difluorophenyl)-3H-imidazo[4,5-b]pyridin-2-yl]methanone; and
  azetidin-1-yl[3-(4-chloro-3-fluorophenyl)-3H-imidazo[4,5-b]pyridin-2-yl]methanone;
  or a pharmaceutically acceptable salt thereof.

28. A pharmaceutical composition comprising a compound of claim 27, or a pharmaceutically acceptable salt thereof, and at least one pharmaceutically acceptable excipient.

29. N-Cyclopropyl-3-(3-fluoro-4-methylphenyl)-3H-imidazo[4,5-b]pyridine-2-carboxamide, or a pharmaceutically acceptable salt thereof.

30. 3-Cyclopentyl-N-cyclopropyl-3H-imidazo[4,5-b]pyridine-2-carboxamide, or a pharmaceutically acceptable salt thereof.

31. 3-(4-Chloro-3-fluorophenyl)-N-cyclopropyl-3H-imidazo[4,5-b]pyridine-2-carboxamide, or a pharmaceutically acceptable salt thereof.

32. 3-(4-Chloro-3-fluorophenyl)-N-(1-methyl-1H-pyrazol-3-yl)-3H-imidazo[4,5-b]pyridine-2-carboxamide, or a pharmaceutically acceptable salt thereof.

33. 4-[2-(Azetidin-1-ylcarbonyl)-3H-imidazo[4,5-b]pyridin-3-yl]-2-fluorobenzonitrile, or a pharmaceutically acceptable salt thereof.

* * * * *